United States Patent

Moormann et al.

[11] Patent Number: 5,945,425
[45] Date of Patent: Aug. 31, 1999

[54] METHOD OF USING (H+/K+)ATPASE INHIBITORS AS ANTIVIRAL AGENTS

[75] Inventors: Alan E. Moormann, Skokie; Daniel P. Becker, Glenview; Daniel L. Flynn, Mundelein; Hui Li, Skokie; Clara I. Villamil, Glenview, all of Ill.

[73] Assignee: G.D. Searle & Co., Skokie, Ill.

[21] Appl. No.: 08/737,251

[22] PCT Filed: May 1, 1995

[86] PCT No.: PCT/US95/05021

§ 371 Date: Oct. 24, 1996

§ 102(e) Date: Oct. 24, 1996

[87] PCT Pub. No.: WO95/29897

PCT Pub. Date: Nov. 9, 1995

Related U.S. Application Data

[63] Continuation-in-part of application No. 08/235,619, Apr. 29, 1994, abandoned.

[51] Int. Cl.[6] .................. A61K 31/42; A61K 31/415; A61K 31/425

[52] U.S. Cl. .................. 514/269; 514/345; 514/394; 514/385; 514/397; 514/398; 514/417; 514/336; 514/337; 514/339; 514/341; 514/342; 514/322; 514/307

[58] Field of Search .................. 546/274.4, 339, 546/361; 548/307.1, 314.7, 325.1, 306.1, 486; 514/345, 394, 385, 397, 398, 417; 544/267, 336, 337, 338, 339, 341, 342, 322, 307; 541/342, 322, 307

[56] References Cited

U.S. PATENT DOCUMENTS

| | | | |
|---|---|---|---|
| 4,045,563 | 8/1977 | Berntsson et al. | 424/263 |
| 4,045,564 | 8/1977 | Berntsson et al. | 424/263 |
| 4,182,766 | 1/1980 | Krasso et al. | 424/263 |
| 4,248,880 | 2/1981 | Krasso et al. | 424/270 |
| 4,255,431 | 3/1981 | Junggren et al. | 424/263 |
| 4,327,102 | 4/1982 | Crossley | 424/263 |
| 4,337,257 | 6/1982 | Junggren et al. | 424/263 |
| 4,359,465 | 11/1982 | Ruwart | 424/263 |
| 4,371,537 | 2/1983 | Markley et al. | 546/274.4 |
| 4,394,509 | 7/1983 | Crossley | 546/339 |
| 4,472,409 | 9/1984 | Senn-Bilfinger | 424/263 |
| 4,772,619 | 9/1988 | Adelstein et al. | 514/338 |

FOREIGN PATENT DOCUMENTS

| | | |
|---|---|---|
| 130729 | 1/1985 | European Pat. Off. . |
| 0167943 | 1/1986 | European Pat. Off. . |
| 167943 | 1/1986 | European Pat. Off. . |
| 0178438 | 4/1986 | European Pat. Off. . |
| 178438 | 4/1986 | European Pat. Off. . |
| 0194458 | 9/1986 | European Pat. Off. . |
| 194458 | 9/1986 | European Pat. Off. . |
| 0234690 | 9/1987 | European Pat. Off. . |
| 234690 | 9/1987 | European Pat. Off. . |
| 335646 | 10/1989 | European Pat. Off. . |
| 0354788 | 2/1990 | European Pat. Off. . |
| 354788 | 2/1990 | European Pat. Off. . |
| 407217 | 1/1991 | European Pat. Off. . |
| 127763 | 11/1992 | European Pat. Off. . |
| 514830 | 11/1992 | European Pat. Off. . |
| 3415971 | 11/1984 | Germany . |
| 3891468 | 2/1994 | Germany . |
| 230560 | 9/1989 | Japan . |
| 2134523 | 8/1984 | United Kingdom . |
| 2161160 | 1/1986 | United Kingdom . |
| 92/07867 | 5/1992 | WIPO . |

OTHER PUBLICATIONS

BO Moorman et al, Method of Using (H+/D+) ATPase Inhibitors as Antiviral Agents, US Ser. No. 08/659,098, Jun. 4, 1996 (filing date).

Okabe et al III Patent Abstracts of Japan, vol. 13, 556 (C–664) 1989.

Lindberg et al, *Trends in Pharmaceutical Sciences*, 399 (1987).

A.A. Altamirano et al, *Virology*, 199, 151 (1994).

T. Hayashi et al, *Chem. Pharm. Bull.*, 38, 2740 (1990).

T. Hayashi et al, *Chem. Pharm. Bull.*, 38, 239 (1990).

T. Hayashi et al, *Antiviral Res.*, 9, 345 (1988).

(List continued on next page.)

*Primary Examiner*—Floyd D. Higel
*Attorney, Agent, or Firm*—Joseph W. Bulock

[57] ABSTRACT

A class of compounds which are (H+/K+)ATPase inhibitors can be used for the treatment of viral infections. Compounds of particular interest are defined by Formula III:

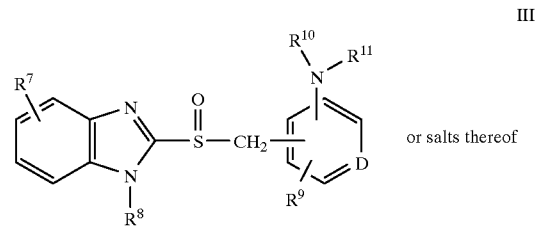

wherein D is N or CH; wherein $R^7$ is one or more radicals selected from hydrido, alkoxy, amino, cyano, nitro, hydroxyl, alkyl, halo, haloalkyl, carboxyl, alkanoyl, nitro, amino, alkylamino, aminocarbonyl, aminosulfonyl, alkylaminocarbonyl, alkylcarbonylamino, alkoxycarbonyl, alkylaminosulfonyl, alkylsulfonylamino, alkylthio, alkylsulfinyl and alkylsulfonyl; wherein $R^8$ is selected from hydrido, alkyl and cycloalkyl; wherein $R^9$ is one or more radicals selected from hydrido, alkoxy, amino, alkyl, halo, cyano, nitro, hydroxyl, haloalkyl, nitro, carboxyl, alkanoyl, amino, alkylamino, dialkylamino, aminocarbonyl, alkylaminocarbonyl, alkylcarbonylamino, aminosulfonyl, alkylaminosulfonyl, alkylsulfonylamino, alkoxycarbonyl, alkylthio, alkylsulfinyl and alkylsulfonyl; and wherein $R^{10}$ and $R^{11}$ are independently selected from hydrido, alkyl, aryl, alkylcarbonyl and arylcarbonyl wherein the aryl ring may be further substituted with one or more radicals selected from alkyl, halo, hydrazidylcarbonyl, aminocarbonyl and alkoxy; or wherein $R^{10}$ and $R^{11}$ together with the nitrogen atom form a heterocyclic ring.

17 Claims, No Drawings

OTHER PUBLICATIONS

N. Naruse et al., *J. Antibiotics,* 43, 267 (1990).
Ljungman et al., *J. Infect. Dis.,* 162, 244 (1990).
Gately et al, *J. Infect. Dis.,* 161, 711 (1990).
F. Liu and B. Roizman, *J. Virol.,* 65, 5149 (1991).

A.R. Welch et al., *Proc. Natl. Acad. Sci. USA,* 88, 10792 (1991).

R.W. Sidwell and J.T. Witkowski, *Antiviral Agents,* in Burger's Medicinal Chemistry, Part II (M. Wolff, 4th Ed. 1979).

METHOD OF USING (H⁺/K⁺)ATPASE INHIBITORS AS ANTIVIRAL AGENTS

This is an application under 35 USC 371 of International Application PCT/US95/05021, with an international filing date of May 1, 1995, which is a continuation in part of U.S. application Ser. No. 08/235,619, filed Apr. 29, 1994, now abandoned.

FIELD OF THE INVENTION

This invention relates to methods of treating subjects having viral infections. More particularly, this invention relates to the use of (H⁺/K⁺)ATPase inhibitors for treating viral infections.

BACKGROUND OF THE INVENTION

Inhibition of the (H⁺/K⁺)ATPase proton pump, located in the gastric secretory membranes, has been a target for controlling gastric acid secretion in the treatment of ulcers.

Several families of compounds have been described as gastric acid secretion inhibitors, including heterocyclylalkylsulfinylbenzimidazoles (see U.S. Pat. Nos. 4,472,409, 4,394,509, 4,337,257, 4,327,102, 4,255,431, 4,045,564, 4,045,563 and 4,772,619; British Patent No. 2,134,523; and German Offenlegungsschrift No. 3,415,971) and heterocyclylalkylsulfinylnaphth[2,3-d]imidazoles (see U.S. Pat. Nos. 4,248,880 and 4,182,766). Similarly, other substituted benzimidazoles having a ring fused to the benzimidazole group have been described as gastric acid secretion inhibitors and cytoprotective agents. See EP Nos. 130,729 and 127,763.

Some heterocyclylalkylsulfinylbenzimidazoles have also been described as cytoprotective agents. See U.S. Pat. No. 4,359,465 and Great Britain Application 2,161,160, published Jan. 8, 1986. Omeprazole is an example of a class of benzimidazoles which inhibit the proton pump [Lindberg et al, *Trends in Pharmaceutical Sciences,* 399 (1987)].

It has been described that inhibitors of sodium transport reduce virus yields [A. A. Altamirano et al, *Virology,* 199, 151 (1994)]. There have been reports of isolated natural products which have been independently described as having (H⁺/K⁺) ATPase inhibitors and antiviral activity. T. Hayashi et al describe the isolation of scopadulcic acid B and its activity against (H⁺/K⁺)ATPase [*Chem. Pharm. Bull.,* 38, 2740 (1990)] and HSV-1 [*Chem. Pharm. Bull.,* 38, 239 (1990) and *Antiviral Res.,* 9, 345 (1988)]. Pumilacidins are a class of heptapeptide antibiotics that have been isolated and described as being inhibitory to HSV-1 as well as (H⁺/K⁺)ATPase [N. Naruse et al, *J. Antibiotics,* 43, 267 (1990)].

There is a great need for new therapies active in the treatment of viral diseases. Whereas there has been great progress in developing a variety of therapies for the treatment of bacterial infections, there are few viable therapies for the treatment of viruses. Zidovudine is the primary approved treatment for human immunodeficiency virus. Ganciclovir, acyclovir and foscarnet are currently utilized for the treatment of herpesvirus infections. However, these therapies can have substantial side effects based on their deleterious effects on host cell DNA replication or effect of a limited number of viral infections. In addition, viruses are known to develop resistance to therapies which causes a progressive decline in efficacy [Ljungman et al., *J. Infect. Dis.,* 162, 244 (1990) and Gately et al, *J. Infect. Dis.,* 161, 711 (1990)].

Herpesviridae is a family of DNA viruses which include herpes simplex virus type-1 (HSV-1), herpes simplex virus type-2 (HSV-2), cytomegalovirus (CMV), varicella-zoster virus (VZV), Epstein-Barr virus (EBV), human herpesvirus-6 (HHV6), human herpesvirus-7 (HHV7), pseudorabies and rhinotracheitis, among others.

It is known that herpesviruses express their genetic content by directing the synthesis of a number of proteins encoded by the herpesvirus DNA in the host cell. One of the important virus-encoded proteins is made as a precursor consisting of an amino terminal-located protease and carboxyl terminal-located assembly protein. This precursor is proteolytically processed in an autocatalytic manner at a specific amino acid sequence known as the "release" site yielding separate protease and assembly protein. The assembly protein is cleaved further by the protease at another specific amino acid sequence known as the "maturation" cleavage site. Recently, EP No. 514,830, published Nov. 25, 1992, describes a virus-specific serine protease which has a role in herpesvirus replication. Additionally, Lui and Roizman (*J. Virol,* 65, 5149 (1991)) describe the sequence and activity of a protease and the associated assembly protein encoded by $U_L26$ of HSV-1. A. R. Welch et al (*Proc. Natl. Acad. Sci. USA,* 88, 10792 (1991)) describe the related protease (also known as assemblin) and assembly protein encoded by $U_L80$ of CMV. An approach currently being investigated for potential use in the treatment of herpesvirus infections is the development of inhibitors of herpesvirus proteases.

U.S. Pat. No. 4,371,537 describes sulfur substituted phenoxypyridines as having activity against RNA viruses, and specifically describes 2,5-bis(benzylthio)pyridine.

Benzimidazoles have been investigated for antiviral activity [R. W. Sidwell and J. T. Witkowski, *Antiviral Agents,* in BURGER'S MEDICINAL CHEMISTRY, PART II (M. Wolff, 4th ed. 1979)]. Specifically, 2-(α-hydroxybenzyl benzimidazole is described as a selective inhibitor of RNA enteroviruses.

EP No. 335,646, published Oct. 4, 1989, describes sulfur-containing compounds as having activity against rhinoviruses and coxsaki virus. Specifically, 5-[7-(benzimidazol-2-yl)sulfoxyheptyl]-3-methylisoxazole is described.

EP 407,217, published Jan., 9, 1991, describes compounds as having activity against RNA viruses. 2-[6-(2-chloro-4-methoxyphenoxy)-1-hexylthio]-benzimidazole is specifically described.

DE 3891468, published Feb. 24, 1994, describes prophylactic anti-herpesvirus activity of 6-bromo-5-hydroxy-4-dimethylaminomethyl-1-methyl-2-phenylthiomethylindol-3-carboxylic acid ethyl ester.

Polysubstituted benzimidazoles with activity against viruses of the herpes family are described in WO 92/07867. 2-Benzylthio-5,6-dichloro-1-(β-D-ribofuranosyl) benzimidazole is specifically described.

DESCRIPTION OF THE INVENTION

The invention involves a method of treating a subject having a viral infection with an (H⁺/K⁺)ATPase inhibitor. Preferably, the (H⁺/K⁺)ATPase inhibitor contains a sulfur radical, such as an alkylthio radical, a sulfoxide radical, a sulfone, or the like. More preferably, the (H⁺/K⁺)ATPase inhibitor contains a sulfoxide radical.

Viruses are classified into broad categories based on whether they incorporate RNA or DNA. Important virus families classified of RNA type include orthomyxoviridae, paramyxoviridae, picornaviridae, rhabdoviridae, coronaviridae, togaviridae, bunyaviridae, arenaviridae and retroviridae. Important virus families classified of DNA type include adenoviridae, poxviridae, papovaviridae and herpesviridae.

The compounds of this invention have been shown to be particularly effective against herpetoviridae. Thus they are particularly useful for the treatment of herpes simplex viruses (HSV-1, HSV-2), cytomegalovirus (CMV), herpes varicella-zoster (VZV), Epstein-Barr (EBV), HHV6, HHV7, pseudorabies and rhinotracheitis, among others.

The invention further involves a method of treating a subject having a viral infection with a effective amount of a compound which can inhibit both a $(H^+/K^+)$ATPase and a virus-specific serine protease.

In addition, the invention involves a method of treating viral infection in a subject, the method comprising treating the subject with an effective amount of a compound of Formula I

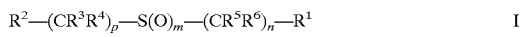

$$R^2-(CR^3R^4)_p-S(O)_m-(CR^5R^6)_n-R^1 \quad\quad I$$

wherein $R^1$ is selected from alkoxy, alkoxycarbonyl, dialkylamino, aryl and heteroaryl, wherein $R^1$ is optionally substituted at a substitutable position with one or more radicals selected from alkoxy, aminoalkoxy optionally substituted on the nitrogen atom with alkyl, cycloalkyl, and aralkyl, hydroxyl, cyano, nitro, alkyl, halo, haloalkyl, haloalkoxy, alkanoyl, cycloalkylalkoxy, carboxyl, acyl, aminocarbonyl, alkylaminocarbonyl, aralkoxy, alkenyloxy, alkynyloxy, aminosulfonyl, dialkylaminosulfonyl, alkylsulfonylamino, heterocyclo, aralkyl, heteroaralkyl, alkoxycarbonyl, heteroaryl, alkylthio, alkylsulfinyl, alkylsulfonyl, alkenylthio, arylthio, aralkylthio, cycloalkylthio, and amino optionally substituted with a radical selected from alkyl, aralkyl, aryl, alkenyl, alkynyl, cycloalkyl, cycloalkenyl, hydroxyalkyl, alkylcarbonyl, alkoxycarbonyl, alkoxyalkyl and arylcarbonyl wherein the aryl ring may be further substituted with one or more radicals selected from alkyl, halo, alkoxy, aminocarbonyl and hydrazidylcarbonyl;

wherein $R^2$ is heteroaryl, wherein $R^2$ is optionally substituted at a substitutable position with one or more radicals selected from alkoxy, amino, cyano, nitro, hydroxyl, alkyl, cycloalkyl, halo, haloalkyl, haloalkoxy, carboxyl, alkanoyl, acyl, alkylamino, arylamino, aralkylamino, alkanoylamino, alkylaminoalkyl, aminocarbonyl, aminocarbonyloxy, alkylaminocarbonyl, alkoxycarbonyl, aryloxycarbonyl, aralkoxycarbonyl, alkylcarbonyl, cycloalkylcarbonyl, alkylcarbonylalkyl, alkoxycarbonylalkyl, alkylcarbonylamino, aryloxy, aralkoxy, alkenyloxy, alkynyloxy, acyloxy, cycloalkylalkoxy, aralkyl, aryl, aroyl, alkoxyalkyl, hydroxyalkyl, heterocyclo, heteroaralkyl, alkylthio, alkylsulfinyl, alkylsulfonyl, arylthio, arylsulfinyl, alkylsulfonyl, aminosulfonyl, alkylsulfonylamino, and alkylaminosulfonyl;

wherein each of $R^3$, $R^4$, $R^5$ and $R^6$ is independently selected from hydrido, alkyl, aryl and aralkyl; or wherein $R^3$ and $R^4$, or $R^5$ and $R^6$ together form cycloalkyl; and wherein each of m, n and p is a number independently selected from 0, 1 and 2;

provided that when $R^1$ is phenyl, $R^2$ is not pyridyl or 1-(β-D-ribofuranosyl)benzimidazole when m is 0 or 2;

or a pharmaceutically acceptable salt or prodrug thereof.

A preferred class of compounds consists of those compounds of Formula I wherein $R^1$ is selected from lower alkoxy, lower alkoxycarbonyl, lower dialkylamino, phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidinyl, thienopyridinyl, dihydrothienopyridinyl, carbostyryl, pyrimidyl and pyrazinyl, wherein $R^1$ is optionally substituted at a substitutable position with one or more radicals selected from lower alkoxy, lower aminoalkoxy optionally substituted on the nitrogen atom with lower alkyl, lower cycloalkyl and lower aralkyl, cyano, nitro, hydroxyl, lower alkyl, halo, lower haloalkyl, lower haloalkoxy, lower cycloalkylalkoxy, carboxyl, acyl, lower alkanoyl, aminocarbonyl, lower alkylaminocarbonyl, lower aralkoxy, lower alkenyloxy, lower alkynyloxy, aminosulfonyl, lower alkylsulfonylamino, lower alkylaminosulfonyl, 5 to 20 membered heterocyclo, lower aralkyl, lower heteroaralkyl, lower alkoxycarbonyl, 5 to 8 membered heteroaryl, lower alkylthio, lower alkylsulfinyl, lower alkylsulfonyl, lower alkenylthio, lower arylthio, lower aralkylthio, lower cycloalkylthio, and amino optionally substituted with a radical selected from lower alkyl, lower aralkyl, phenyl, lower alkenyl, lower alkynyl, lower cycloalkyl, acyl, lower cycloalkenyl, lower hydroxyalkyl, lower alkylcarbonyl, lower alkoxycarbonyl, lower alkoxyalkyl and phenylcarbonyl wherein the phenyl ring may be further substituted with one or more radicals selected from lower alkyl, halo, lower alkoxy, aminocarbonyl and hydrazidylcarbonyl; wherein $R^2$ is selected from nitrogen-containing heteroaryl, wherein $R^2$ is optionally substituted at a substitutable position with one or more radicals selected from lower alkoxy, amino, cyano, nitro, hydroxyl, lower alkyl, lower cycloalkyl, halo, lower haloalkyl, lower haloalkoxy, carboxyl, lower alkanoyl, acyl, lower alkylamino, lower arylamino, lower alkylarylamino, lower alkanoylamino, lower alkylaminoalkyl, aminocarbonyl, lower alkylaminocarbonyl, lower alkoxycarbonyl, lower aryloxycarbonyl, aralkoxycarbonyl, lower alkylcarbonyl, lower cycloalkylcarbonyl, lower alkylcarbonylalkyl, lower alkoxycarbonylalkyl, lower alkylcarbonylamino, aminocarbonyloxy, lower aryloxy, lower aralkoxy, lower alkenyloxy, lower alkynyloxy, acyloxy, lower cycloalkylalkoxy, lower aralkyl, optionally substituted lower aryl, lower aroyl, lower alkoxyalkyl, lower hydroxyalkyl, 5 to 20 membered heterocyclo, lower heteroaralkyl, lower alkylthio, lower alkylsulfinyl, lower alkylsulfonyl, lower arylthio, lower arylsulfinyl, lower arylsulfonyl, lower alkylsulfonylamino, aminosulfonyl and lower alkylaminosulfonyl; and wherein each of $R^3$, $R^4$, $R^5$ and $R^6$ is independently selected from hydrido, lower alkyl, phenyl, naphthyl and lower aralkyl; or wherein $R^3$ and $R^4$, or $R^5$ and $R^6$ together form lower cycloalkyl; or a pharmaceutically acceptable salt thereof.

A class of compounds of particular interest consists of those compounds of Formula I wherein $R^1$ is selected from phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidinyl, thienopyridinyl, dihydrothienopyridinyl, carbostyryl, pyrimidyl and pyrazinyl, wherein $R^1$ is optionally substituted at a substitutable position with one or more radicals selected from methoxy, ethoxy, propoxy, butoxy, isopropoxy, tert-butoxy, aminoethoxy optionally substituted on the nitrogen atom with methyl, ethyl, propyl, butyl, pentyl, isopropyl, isobutyl, tert-butyl, cyclohexyl, cyclopropyl and benzyl, hydroxyl, amino optionally substituted with a radical selected from methyl, ethyl, propyl, butyl, pentyl, isopropyl, isobutyl, tert-butyl, benzyl, phenethyl, phenyl, butene, pentene, isopropylene, isobutylene, propargyl, cyclopropyl, cyclobutyl, cyclopentyl, cyclohexyl, formyl, acetyl, cyclobutenyl, cyclopentenyl, cyclohexenyl, hydroxymethyl, methylcarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methoxymethyl, and phenylcarbonyl wherein the phenyl ring may be further substituted with one or more radicals selected from methyl, chloro, methoxy, aminocarbonyl and hydrazidylcarbonyl, cyano, nitro, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichioropropyl, trifluoromethoxy, cyclohexylmethoxy, carboxyl, formyl, acetyl, propionyl, aminocarbonyl, methylaminocarbonyl, dimethylaminocarbonyl, benzyloxy, aminosulfonyl, dimethylaminosulfonyl, methylsulfonylamino, morpholinyl, pyrrolidinyl, phthalimidyl, piperazinyl, piperidyl, benzyl, methoxycarbonyl, ethoxycarbonyl, pyridyl, methylthio, methylsulfinyl, methylsulfonyl, phenylthio, benzylthio, and cyclohexylthio; wherein $R^2$ is selected from pyridyl, indolyl, imidazolyl, benzimidazolyl, napthoimidazolyl, 1,3-dioxolobenximidazolyl, imidazopyridyl, imidazoquinolinyl, dihydroimidazoquinolinyl, cycloheptoimidazolyl, cyclooxaundecanobenzimidazolyl, benzoxazolyl, benzothiazolyl, indolyl, thienoimidazolyl, pyridopyrazinyl, quinolinyl, quinoxalinyl, quinazolinyl, quinazolinonyl, triazolyl, tetrazolyl, oxazolyl, purinyl, indenoimidazolyl, thiadiazolyl, thiazolylpyridyl, pyridyl, pyrimidinyl, pyranobenzimidazolyl, thiopyranbenzimidazolyl, indolbenzimidazole, tetrahydroimidazoquinolinyl, wherein $R^2$ is optionally substituted at a substitutable position with one or more radicals selected from methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, cyclohexyl, cyclopropyl, cyclobutyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, trifluoroethoxy, carboxyl, formyl, acetyl, propionyl, butyryl, N-methylamino, N-ethylamino, N-propylamino, N-butylamino, N-tert-butylamino, N-pentylamino, N-hexylamino, N,N-dimethylamino, phenylamino, N-methyl-N-phenylamino, methylaminomethyl, aminocarbonyl, N-methylaminocarbonyl, N,N-dimethylaminocarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, phenoxycarbonyl, benzyloxycarbonyl, methylcarbonyl, cyclohexylcarbonyl, methylcarbonylmethyl, methoxycarbonylmethyl, methylcarbonylamino, aminocarbonyloxy, phenoxy, benzoxy, benzyl, phenethyl, phenyl, benzoyl, methoxymethyl, hydroxymethyl, morpholinyl, pyrrolidinyl, piperazinyl, piperidyl, methylthio, ethylthio, methylsulfinyl, ethylsulfinyl, methylsulfonyl, phenylthio, phenylsulfinyl, phenylsulfonyl, aminosulfonyl, methylsulfonylamino, methylaminosulfonyl and N,N-dimethylaminosulfonyl; wherein each of $R^3$, $R^4$, $R^5$ and $R^6$ is independently selected from hydrido, methyl, ethyl, propyl, butyl, pentyl, isopropyl, isobutyl, tert-butyl, phenyl and benzyl; or wherein $R^3$ and $R^4$, or $R^5$ and $R^6$ together form cyclopropyl, cyclobutyl or cyclopentyl; wherein m and n are 1; and wherein p is 0; or a pharmaceutically acceptable salt thereof.

A family of specific compounds of particular interest within Formula I consists of compounds, and their pharmaceutically acceptable salts, of the group selected from:

2-[(4,6-dimethyl-5-methoxy-2-phthalimidylphenyl)methylsulfonyl]-5-methoxy-1H-benzimidazole;

2-[[(5-chloro-1H-benzimidazol-2-yl)sulfinyl]methyl]-3,5-dimethyl-4-methoxybenzenamine;

(+)-2-[[(5-methoxy-1H-benzimidazol-2-yl)sulfinyl]methyl]-3,5-dimethyl-4-methoxybenzenamine;

(−)-2-[[(5-methoxy-1H-benzimidazol-2-yl)sulfinyl]methyl]-3,5-dimethyl-4-methoxybenzenamine;

N-[2-[[(6-methoxy-1H-benzimidazol-2-yl)sulfinyl]methyl]-3,5-dimethyl-4-methoxyphenyl]acetamide;

2-[(4,6-dimethyl-5-methoxy-2-phthalimidylphenyl)methylsulfinyl]-6-chloro-1-isopropyl-1H-benzimidazole;

2-[(4,6-dimethyl-5-methoxy-2-phthalimidylphenyl)methylsulfinyl]-5-chloro-1-isopropyl-1H-benzimidazole;

2-[[(1-methyl-1H-imidazol-2-yl)sulfinyl]methyl]-3,5-dimethyl-4-methoxybenzenamine;

2-[[(1H-imidazol-2-yl)sulfinyl]methyl]-3,5-dimethyl-4-methoxybenzenamine;

2-[(4,6-dimethyl-5-methoxy-2-phthalimidylphenyl)methylsulfinyl]-5-chloro-1-ethyl-1H-benzimidazole;

2-[(4,6-dimethyl-5-methoxy-2-phthalimidylphenyl)methylsulfinyl]-6-chloro-1-ethyl-1H-benzimidazole;

2-[[[2-[[(6-chloro-1-ethyl-1H-benzimidazol-2-yl)sulfinyl]methyl]-3,5-dimethyl-4-methoxyphenyl]amino]carbonyl]benzenecarboxylic acid hydrazide;

2-[[[2-[[(5-chloro-1-ethyl-1H-benzimidazol-2-yl)sulfinyl]methyl]-3,5-dimethyl-4-methoxyphenyl]amino]carbonyl]benzenecarboxylic acid hydrazide;

3-[[(1H-benzimidazol-2-yl)sulfinyl]methyl]-benzenamine;

4-methoxy-3,5-dimethyl-2-[(2-pyridinyl)sulfinylmethyl]benzenamine;

[2-[(2-N-isobutyl-N-methylamino)-benzyl]sulfinyl]-1H-benzimidazole;

2-[[3-methylpyridin-2-ylmethyl]sulfinyl]-1H-benzimidazole;

2-[(imidazo[1,2-a]pyridin-3-yl)methylsulfinyl]-1H-benzimidazole;

2-[(imidazo[1,2-a]pyridin-3-yl)methylsulfinyl]-1H-benzimidazole;

2-[(imidazo[1,2-a]pyridin-3-yl)methylsulfinyl]-5-methyl-1H-benzimidazole;

2-[(imidazo[1,2-a]pyridin-3-yl)methylsulfinyl]-5-methoxy-1H-benzimidazole;

5-chloro-2-[(imidazo[1,2-a]pyridin-3-yl-methyl)sulfinyl]-1H-benzimidazole;

2-[(imidazo[1,2-a]pyridin-3-yl)methylsulfinyl]-5-trifluoromethyl-1H-benzimidazole;

2-[(imidazo[1,2-a]pyridin-8-yl)methylsulfinyl]-1H-benzimidazole;

2-[(imidazo[1,2-a]pyridin-8-yl)methylsulfinyl]-1H-benzimidazole;

2-[(imidazo[1,2-a]pyridin-8-yl)methylsulfinyl]-5-methoxy-1H-benzimidazole;

5-ethoxy-2-[(imidazo[1,2-a]pyridin-8-yl-methyl)sulfinyl]-1H-benzimidazole;

2-[(imidazo[1,2-a]pyridin-8-yl)methylsulfinyl]-4-methyl-1H-benzimidazole;
2-[(imidazo[1,2-a]pyridin-8-yl)methylsulfinyl]-5-methyl-1H-benzimidazole;
2-[(imidazo[1,2-a]pyridin-8-yl)methylsulfinyl]-5,6-dimethyl-1H-benzimidazole;
2-[(imidazo[1,2-a]pyridin-8-yl)methylsulfinyl]-5,6-dimethoxy-1H-benzimidazole;
5-chloro-2-[(imidazo[1,2-a]pyridin-8-yl-methyl)sulfinyl]-1H-benzimidazole;
2-[(imidazo[1,2-a]pyridin-8-yl)methylsulfinyl]-5-trifluoromethyl-1H-benzimidazole;
2-[[(2,3-dimethylimidazo[1,2-a]pyridin-8-yl)methyl]sulfinyl]-1H-benzimidazole;
2-[[(3-methylimidazo[1,2-a]pyridin-8-yl)methyl]sulfinyl]-1H-benzimidazole;
2-[[(2-phenylimidazo[1,2-a]pyridin-8-yl)methyl]sulfinyl]-1H-benzimidazole;
2-[[(3-phenylimidazo[1,2-a]pyridin-8-yl)methyl]sulfinyl]-1H-benzimidazole;
2-[[(3-(4-nitrophenyl)imidazo[1,2-a]pyridin-8-yl)methyl]sulfinyl]-1H-benzimidazole;
2-[[[3-[3-(trifluoromethyl)phenyl]imidazo[1,2-a]pyridin-8-yl]methyl]sulfinyl]-1H-benzimidazole;
5-methyl-2-[[[3-[3-(trifluoromethyl)phenyl]imidazo[1,2-a]pyridin-8-yl]methyl]sulfinyl]-1H-benzimidazole;
5-chloro-2-[[[3-[3-(trifluoromethyl)phenyl]imidazo[1,2-a]pyridin-8-yl]methyl]sulfinyl]-1H-benzimidazole;
2-[[[3-[4-(trifluoromethyl)phenyl]imidazo[1,2-a]pyridin-8-yl]methyl]sulfinyl]-1H-benzimidazole;
5-chloro-2-[[[3-[4-(trifluoromethyl)phenyl]imidazo[1,2-a]pyridin-8-yl]methyl]sulfinyl]-1H-benzimidazole;
4-[8-[(1H-benzimidazol-2-yl)sulfinyl]methyl]imidazo[1,2-a]pyridin-3-yl]benzoate;
2-[[[3-(4-chlorophenyl)imidazo[1,2-a]pyridin-8-yl]methyl]sulfinyl]-1H-benzimidazole;
2-[[[3-(4-methylphenyl)imidazo[1,2-a]pyridin-8-yl]methyl]sulfinyl]-1H-benzimidazole;
2-[(imidazo[1,2-a]pyridin-5-yl)methylsulfinyl]-1H-benzimidazole;
2-((n-butoxycarbonylmethyl)sulfinyl)thiazolo (5,4-b)pyridine;
5-chloro-2-((2-ethoxyethyl)sulfinyl)benzothiazole;
4,6-dimethyl-2-(((imidazo(1,2-a)pyridin-2-yl)methyl)thio)-1H-benzimidazole;
2-[3-methyl-4-(2-(N-benzyl-N-cyclohexylamino)-ethoxy)pyridyl]methylthio-1H-benzimidazole;
ethyl 2-[(1H-benzimidazol-2-yl)thiomethyl]-4-methyl-amino-5-pyrimidine carboxylate;
9-(benzimidazol-2-yl)sulfinyl-4-methoxy-2,3-cycloheptenopyridine;
2-(5-fluoro-2-(4-methoxy-2-pyridyl)-phenylsulfinyl)-1H-benzimidazole;
5-difluoromethoxy-2-(((3,4-dimethoxy-2-pyridinyl)methyl)sulfinyl)-1H-benzimidazole;
2-(((4-difluoromethoxy-3-methyl-2-pyridyl)methylsulfinyl)benzimidazole;
2-[4(3-methoxypropoxy)-3-methylpyridine-2-yl]methylsulfinyl-1H-imidazole;
2-((6-azachroman-5-yl)methylsulfinyl)-benzimidazole;
5-carbomethoxy-6-methyl-2-(((3,4-dimethoxy-2-pyridinyl)-methyl)sulfinyl-1H-benzimidazole;
5-carbomethoxy-6-methyl-2-(((3,4-dimethoxy-2-pyridinyl)-methyl)sulfinyl)-1H-benzimidazol-1-yl-methyl ethylcarbonate;
2-((3-methyl-4-(2,2,2-trifluoroethoxy)-2-pyridyl)methylsulfinyl)benzimidazole;
4-fluoro-2-(((4-methoxy-2-pyridinyl)methyl)sulfinyl-1H-benzimidazol-1-yl-methyl-ethylcarbonate;
2-[3-methyl-4-(1-benzyl-4-piperidyl)oxy-2-pyridyl]methylthio-1H-benzimidazole;
2-(3-methyl-4-(2-(N-methyl-N-(4-methyl-benzyl)amino)ethoxy)-2-pyridyl)methylsulfonyl-1H-benzimidazole;
2-(4-methoxy-6-methyl-2-pyrimidinyl)methylthio-1H-benzimidazole;
2-[2-[N-4-(3-fluorophenyl)-butyl-N-methyl]aminoethyl]thio-(1H)-benzimidazole;
5-chloro-2-(3,4-dimethoxy-2-pyridylmethylsulfinyl)-1H-benzimidazole;
5-fluoro-2-(4-cyclopropylmethoxy-2-pyridylmethyl-sulfinyl)-1H-benzimidazole;
4-fluoro-2-(4-methoxy-2-pyridylmethylsulfinyl)-1H-benzimidazole;
2-(((4-methoxy-3,5-dimethyl-2-pyridinyl)-methyl)-sulfinyl)-5-methoxy-1H-benzimidazole;
5-hydroxymethyl-2-(((3,5-dimethyl-4-methoxy-2-pyridyl)methylthio-1H-benzimidazole;
2-(4-ethylthio-3-methylpyridin-2-yl-methyl)sulfinyl-benzimidazole;
2-(((4-(2-benzyloxyethoxy)-3-methyl-2-pyridyl)methylthio)benzimidazole;
2-[[2-[N-(2-hydroxyethyl)-N-methylamino]-5-methoxy]benzylsulfinyl]benzimidazole;
2-[2-(3,5-dimethyl-4-ethoxy)pyridylmethylsulfinyl]-5-methoxy-imidazo(4,5-b)pyridine;
2-(5-benzyl-4-chloro-6-methyl-2-pyrimidinyl)methylthio-1H-benzimidazole;
2,2-difluoro-6-((5-benzyloxy-4-methoxy-2-pyridyl)methylthio)-5H-(1,3)-dioxolo(4,5-f)benzimidazole;
5-carboethoxy-6-methyl-2-(((3-methyl-2-pyridyl)methyl)sulfinyl)-1H-benzimidazole;
5-(2-benzimidazolylsulfinylmethyl)-3,4-dihydro-4-methyl-2H-1,4-benzoxazine;
2-(3-methyl-4-(2-(N-benzyl-N-methylamino)ethoxy-2-pyridyl)methylsulfinyl-1H-benzimidazole;
2-(3-methyl-4-(2-(1,2,3,4-tetrahydroisoquinolin-2-yl)-ethoxy)-2-pyridyl)methylsulfinyl-1H-benzimidazole;
2-[1-(3,5-dimethylpyrazolyl)]methylthiobenzimidazole;
2-(3-chloro-4-methoxy-2-picolylthio)-5-methoxy-1H-benzimidazole;
2-(4-(2-ethoxyethoxy)-3-methyl-2-pyridyl)methylsulfinyl-1H-benzimidazole;
2-(3-methylthieno(2,3-c)pyridin-7-yl)methylsulfinyl)-benzimidazole;
2-(2-dimethylamino-5-methoxybenzylsulfinyl)-5-methoxy-benzimidazole;
2-(2-dimethylamino-5-methylbenzylsulfinyl)-5-methoxybenzimidazole;
2-[4-(2,3,5-trimethyl)pyridylthio]-5-methoxybenzimidazole;
2[(2-(4-chlorophenyl)-5-methylimidazol-4-yl) methylthio]-benzimidazole;
2-(5-hydroxy-1H-benzimidazol-2-ylsulfinylmethyl)-N,N-dimethylbenzenamine;
2-((6-methoxyisoquinolin-1-yl)methylsulfinyl)benzimidazole;
3-(5-methoxy-1H-benzimidazol-2-yl)thiomethylcarbostyril;
5-methoxy-2-(4-dimethylamino-5-fluoro-2-pyridylmethylsulfinyl)-1H-benzimidazole;
2-(2-dimethylaminobenzyl-sulfinyl)-5-cyclopropyl-methoxy)-benzimidazole;
2-(3,5-dimethyl-2-pyridylmethylsulfinyl)-5-cyclopropylmethoxy-benzimidazole;
2-[2-(N-cyclohexyl-N-methylamino)benzylsulfonyl]benzimidazole;

8-(5-fluoro-6-methoxy-2-benzimidazolyl)sulfinylmethyl-1-ethyl-4-(N-methyl-N-allyl)amino-1,2,3,4-tetrahydroquinoline;
2-(2-benzyloxycarbonylaminobenzylthio)benzimidazole;
2-(2-benzimidazolylmethylthio)pyrimidine;
2-(2-dimethylaminobenzylsulfinyl)imidazo[4,5-b]-pyridine;
2-(2-pyridylmethylsulfinyl)quinoxaline;
2-methyl-3-(2-pyridylmethylsulfinyl)pyrido[2,3-b]pyrazine;
5-acetyl-2-((2-dimethylaminobenzyl)sulfinyl)benzimidazole;
2-((3,5-dimethyl-4-methoxy-2-pyridyl)methylsulfinyl)-5-fluoro-1H-benzimidazole;
2-(3-pyridylmethylthio)-5-methoxybenzimidazole;
2-(2-methylaminobenzylsulfinyl)benzimidazole;
5-methoxy-2-(2-dimethylaminobenzylsulfinyl)-1H-benzimidazole;
2-(3,4-dimethoxypyrid-2-ylmethylsulfinyl)-5-trifluoromethyl-benzimidazole;
5-methoxy-2-(4-piperidino-2-pyrimidinylmethylsulfinyl)-(1H)-benzimidazole;
2-[2-(4-benzyloxy)-pyridylmethylsulfinyl]benzimidazole;
4-allyloxy-8-(2-benzimidazolyl)thio-3-methyl-5,6,7,8-tetrahydroquinoline;
2-[2-(4-methoxy-5-n-pentyl)-pyridylmethylthio]benzimidazole;
2-(5-bromo-4-piperidino-2-pyridylmethylsulfinyl)-5-methoxy-(1H)-benzimidazole;
2-((3,5-dimethyl-4-morpholinopyrid-2-yl)methylsulfinyl)benzimidazole;
2-((2-pyridinylmethyl)sulfinyl)-1H-benzimidazole-1-methanol;
2-((3,4-dihydro-2H-thieno(3,2-c)pyridinylmethyl)thio)-1H-benzimidazole-1-methanol;
2-(4-isopropoxy-2-pyridyl)methylsulfinylbenzimidazole;
2-((4-fluorobenzyloxy-3-methyl-2-pyridyl)methylsulfinyl)benzimidazole;
2-(2-aminobenzylsulfinyl)-benzimidazole;
N,N-dimethyl-2-(1H-benzimidazol-2-yl-sulfinylmethyl)benzenamine;
2-[(4,5-dimethoxy-2-pyridyl)methylsulfinyl]-5-trifluoromethoxy-1H-benzimidazole;
2,2-difluoro-6-[(4,5-dimethoxy-2-pyridyl)methylthio]-5H-1,3-dioxolo-(4,5-f)benzimidazole;
2-((4-morpholinyl-3-ethylpyridin-2-yl)methylsulfinyl)-5-trifluoromethylbenzimidazole;
2-((4-methoxy-2-pyridyl)methylsulfinyl)-5-trifluoromethoxy-1H-benzimidazole;
5-cyclopropylcarbonyl-2-((4-methoxy-2-pyridyl)methyl-sulfinyl)-1H-benzimidazole;
2-[2-(3,5-dimethyl-4-methoxy)-pyridylmethylsulfinyl]-(5-chloro)-benzimidazole;
2-[2-(4,5-dimethyl)-pyridylmethylsulfinyl]-(5-acetyl-6-methyl)-benzimidazole;
1-(p-chlorobenzoyl)-2-(β-morpholinylmethyl-sulfinyl)benzimidazole;
2,3-dihydro-2-(2-pyridyl)thiazolo[3,2-a]benzimidazole-1-oxide;
2-[(2-pyridylmethyl)thio]-1H-naphth[2,3-d]imidazole;
1,5,6,7-tetrahydro-2-(5-methyl-2-pyridyl-methyl)-thio)indeno(5,6-d)imidazole;
4-methyl-2-(5-methyl-2-pyridyl-methylthio)-1H-naphtho(2,3-d)imidazole;
2,2-difluoro-6-(4-methoxy-2-pyridylmethylsulfinyl)-5H-1,3-dioxolo[4,5-f]benzimidazole;
2-benzylthio-(4H)-imidazo(4,5,1-ij)quinoline;
2-(2-chlorophenylmethylthio)-5,6-dihydro-(4H)-imidazo(4,5,1-ij)quinoline;
5,6-dihydro-2-(2-pyridylmethylthio)-4H-imidazo(4,5,1-ij)quinoline;
5,6-dihydro-2-(2-(3,5-dimethylpyridyl)methylsulfinyl)-4H-imidazo;
5,7-dihydro-2-(((4-methoxy-3-methyl-2-pyridyl)methyl)sulfinyl)-5,5,7,7-tetramethylindeno(5,6-d)imidazol-6(1H)-one;
2-(2-pyridylmethylthio)-6-isopropyl-cycloheptoimidazole;
2-[2-(3,5-dimethyl)pyridylmethylsulfinyl]5-fluoro-benzoxazole;
3-[(4-dimethylamino-2-pyridyl)methylthio]indole;
5-methyl-2-(2-pyridylmethylthio-3H-thieno(2,3-d)imidazole;
2-(2-(3,5-dimethyl-4-methoxy)pyridylmethylsulfinyl)-7-imidazo(4,5-b)pyridine;
2-(2-pyridylmethylsulfinyl)quinoxaline;
2-[(2-pyridyl)methylsulfinyl]thieno[3,4-d]-imidazole;
2-(((3,5-dimethyl-4-methoxy-2-pyridyl)methyl)thio)-4,5-diphenyloxazole;
3,5-dimethyl-4-methoxy-6-(((5-phenyl-1,2,4-triazol-3-yl)-thio)methyl)pyridine;
2-(((3,5-dimethyl-4-methoxy-2-pyridyl)methyl)sulfinyl)-4,5-diphenylimidazole;
5-(((4,5-diphenyl-2-oxazolyl)sulfinyl)methyl)-2,2-dimethyl-8-methyl-4H-1,3-dioxino(4,5-c)pyridine;
5-(((3,5-dimethyl-4-methoxy-2-pyridyl)methyl)sulfinyl)-1-methyltetrazole;
6-benzoylamino-7-chloro-2-(((3,5-dimethyl-4-methoxy-2-pyridyl)-methyl)thio)benzothiazole;
2-[[(3,5-dimethyl-4-methoxy-2-pyridyl)-methyl]thiol]quinoline;
2-[2-(3,5-dimethyl)pyridylmethylsulfinyl]-5-methoxy-imidazo[4,5-b]pyridine;
5-(4,5-dihydro-2-oxazolyl)-2-((3,5-dimethyl-4-methoxy-2-pyridyl)methylthio)-1H-benzimidazole;
2-(2-dimethylaminobenzylsulfinyl)-5-methoxyimidazo[4,5-b]-pyridine;
3-phenyl-2-(2-pyridylmethylsulfinyl)-4(3H)-quinazolinone;
4-amino-2-(2-pyridylmethylthio)quinazoline;
2-(4-morpholinyl-2-pyrimidinylmethylthio)thieno(3,4-d)imidazole;
8-[2'-(N,N-dimethylanily)methylthio]purine;
2-[2'-(N,N-dimethylanily)methylthio]thieno-(3,4-d)-imidazole;
2-(4-methoxy-2-picolinylthio)-1H-thieno[3,4-d]imidazole;
2-(2-pyridylmethyl)thio-8H-indeno(1,2-d)imidazole;
2-(4-methoxy-5-chloro-2-picolythio)-1H-thieno(3,4-d)imidazole;
2-[2-(1-pyrrolidinyl)benzylthio]cycloheptoimidazole;
2-(2-acetylaminophenyl)methylthiocycloheptoimidazole;
2-amino-5-(2-(2-pyridyl)ethylthio)-1,3,4-thiadiazole;
2-gernaylthio-benzimidazole;
2-(2-chlorobenzylthio)-8,8-dimethyl-6-oxo-5,6,7,8-tetrahydro-3H-imidazo[4,5-g]quinoline;
8-(2-pyrimidinyl-sulfinyl)quinoline;
2-((3-methyl-2-pyridyl)methylsulfinyl)pyrano(2,3-f)benzimidazole;
2-[(2-isobutylamino)benzylsufinyl]imidazole;
ethyl 2-((1H-benzimidazol-2-yl)-sulfinylmethyl)-4-dimethylamino-5-pyrimidinecarboxylate;
2-((2-ethoxyethyl)sulfinyl)-4-(3-pyridyl)thiazole;
2-[2-(2-propynylamino)benzylsulfinyl]imidazole;
2-(2-(2-methoxyethylamino)benzylsulfinyl)imidazole;
1-(2-pyridyl)-2-(3-dimethylamino)benzylsulfinyl)imidazole;
2-(2-methylaminobenzylthio)-4,5,6,7-tetrahydro-1H-benzimidazole;

4,5-diphenyl-2-(2-pyridylmethyl)-thioimidazole;
4-phenyl-2-(2-pyridylmethyl)thioimidazole;
4,5-bis(4-methoxyphenyl)-2-(2-thienylthio)imidazole;
2-(3-chloro-2-pyridinylthiomethyl)-4,5-dihydro-1H-imidazole;
1-methyl-2-(2-pyrimidinylthiomethyl)-5-nitro-imidazole;
1-methyl-2-(2-pyridylsulfonylmethyl)-5-nitroimidazole;
1-methyl-2-(5-bromo-2-pyridylthiomethyl)-5-nitro-imidazole;
2-[(1H-benzimidazol-2-yl)sulfinylmethyl]benzenamine;
2-[(1H-benzimidazol-2-yl)sulfinylmethyl]N,N-dimethylbenzenamine;
N-[2-[(1H-benzimidazol-2-yl)sulfinylmethyl]phenyl]acetamide;
2-[[(4-methyl-1H-benzimidazol-2-yl)sulfinyl]methyl]benzenamine;
2-[[(5,6-dimethyl-1H-benzimidazol-2-yl)sulfinyl]methyl]benzenamine;
2-[[(5-methoxy-1H-benzimidazol-2-yl)sulfinyl]methyl]benzenamine;
methyl 2-[[(2-aminophenyl)methyl]sulfinyl]-5-methoxy-1Hbenzimidazole-6-carboxylate;
2-[(1H-benzimidazol-2-yl)sulfinylmethyl]-4-chlorobenzenamine;
2-[(1H-benzimidazol-2-yl)sulfinylmethyl]-5-chlorobenzenamine;
2-[(1H-benzimidazol-2-yl)sulfinylmethyl]-4-methoxybenzenamine;
2-[(1H-benzimidazol-2-yl)sulfinylmethyl]-6-methoxybenzenamine;
2-[(1H-benzimidazol-2-yl)sulfinylmethyl]-3-methylbenzenamine;
2-[(1H-benzimidazol-2-yl)sulfinylmethyl]-4-methylbenzenamine;
2-[(1H-benzimidazol-2-yl)sulfinylmethyl]-6-methylbenzenamine;
2-[(1H-benzimidazol-2-yl)sulfinylmethyl]-4,6-dimethylbenzenamine;
2-[(1H-benzimidazol-2-yl)sulfinylmethyl]-N-methylbenzenamine;
2-[[(5-methoxy-1H-benzimidazol-2-yl)sulfinyl]methyl]-4-methylbenzenamine;
2-[[(5-methoxy-1H-benzimidazol-2-yl)sulfinyl]methyl]-6-methylbenzenamine;
2-[(1H-benzimidazol-2-yl)sulfinylmethyl]-4-ethylbenzenamine;
2-[(1H-benzimidazol-2-yl)sulfinylmethyl]-6-ethylbenzenamine;
2-[(1H-benzimidazol-2-yl)sulfinylmethyl]-4-methoxy-3,5-dimethylbenzenamine;
2-[[(5-methyl-1H-benzimidazol-2-yl)sulfinyl]-methyl]benzenamine;
2-[[(5-chloro-1H-benzimidazol-2-yl)sulfinyl]-methyl]benzenamine;
2-[[(5-ethoxy-1H-benzimidazol-2-yl)sulfinyl]-methyl]benzenamine;
2-[[[5-(trifluoromethyl)-1H-benzimidazol-2-yl]sulfinyl]methyl]benzenamine;
2-[(1H-benzimidazol-2-yl)sulfinylmethyl]-4-(trifluoromethyl)benzenamine;
2-[(1H-benzimidazol-2-yl)sulfinylmethyl]-4-butylbenzenamine;
2-[(1H-benzimidazol-2-yl)sulfinylmethyl]-5,6-dimethylbenzenamine;
2-[(1H-benzimidazol-2-yl)sulfinylmethyl]-3,6-dimethylbenzenamine;
2-[(1H-benzimidazol-2-yl)sulfinylmethyl]-4-chloro-6-methylbenzenamine;
2-[(1H-benzimidazol-2-ylsulfiny)methyl]-4-chloro-6-methoxy-3-methylbenzenamine;
2-[[(5-ethoxy-1H-benzimidazol-2-yl)sulfinyl]-methyl]-4-methylbenzenamine;
2-[[(5-methyl-1H-benzimidazol-2-yl)sulfinyl]-methyl]-5,6-dimethylbenzenamine;
2-[[[(5-(trifluoromethy)1-1H-benzimidazol-2-yl]sulfinyl]-3,6-dimethylbenzenamine;
2-[[[(5-(trifluoromethyl)1-1H-benzimidazol-2-yl]sulfinyl]methyl]-6-methoxybenzenamine;
methyl 2-amino-3-[(1H-benzimidazol-2-yl)sulfinyl)methyl]benzoate;
ethyl 4-amino-3-[(1H-benzimidazol-2-yl)sulfinyl)methyl]benzoate;
ethyl 4-amino-3-[[(5-methoxy-1H-benzimidazol-2-yl)sulfinyl]methyl]benzoate;
2-[[5,6-dimethoxy-1H-benzimidazol-2-yl)sulfinyl]methyl]-4-methylbenzenamine;
2-[(1H-benzimidazol-2-yl)sulfinylmethyl]-4-fluorobenzenamine;
2-[(1H-benzimidazol-2-yl)sulfinylmethyl]-3,4,5-trimethylbenzenamine;
2-[[(5-methoxy-1H-benzimidazol-2-yl)sulfinyl]methyl]-4-methoxy-3,5-dimethylbenzenamine;
3-[(1H-benzimidazol-2-yl)sulfinylmethyl]benzenamine;
3-[(1H-benzimidazol-2-yl)sulfinylmethyl]-2-pyridinamine;
3-[(1H-benzimidazol-2-yl)sulfinylmethyl]-N,N-dimethyl-2-pyridinamine;
6-[(1H-benzimidazol-2-yl)sulfinylmethyl]-2-pyridinamine;
6-[[(4-methyl-1H-benzimidazol-2-yl)-sulfinyl]methyl]-2-pyridinamine;
6-[[(5-methyl-1H-benzimidazol-2-yl)-sulfinyl]methyl]-2-pyridinamine;
6-[[(5-methoxy-1H-benzimidazol-2-yl)sulfinyl]-methyl]-2-pyridinamine;
6-[[(5-chloro-1H-benzimidazol-2-yl)-sulfinyl]methyl]-2-pyridinamine;
6-[[[5-(trifluoromethyl)-1H-benzimidazol-2-yl]sulfinyl]methyl]-2-pyridinamine;
6-[[(5-ethoxy-1H-benzimidazol-2-yl)-sulfinyl]methyl]-2-pyridinamine;
6-[[(5,6-dimethoxy-1H-benzimidazol-2-yl)-sulfinyl]methyl]-2-pyridinamine;
6-[[(5,6-dimethyl-1H-benzimidazol-2-yl)-sulfinyl]methyl]-2-pyridinamine;
6-[[(4,6-dimethyl-1H-benzimidazol-2-yl)-sulfinyl]methyl]-2-pyridinamine;
6-[[[5-(hydroxymethyl)-1H-benzimidazol-2-yl]sulfinyl]methyl]-2-pyridinamine;
6-[(1H-benzimidazol-2-yl)sulfinylmethyl]-N-(2,2-dimethylpropyl)-2-pyridinamine;
6-[(1H-benzimidazol-2-yl)sulfinylmethyl]-N-ethyl-2-pyridinamine; and
5-[(1H-benzimidazol-2-yl)sulfinylmethyl]-2-pyridinamine.

Within Formula I there is a subclass of compounds of high interest which can be used to treat a subject with a viral infection, represented by Formula II:

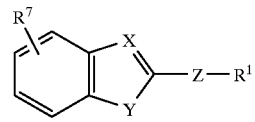

II wherein X is selected from CH or N;
wherein Y is selected from $CH_2$, $NR^8$, O and S;

wherein Z is selected from —S(O)$_m$—, —(CR$^3$R$^4$)$_p$S(O)$_m$— and —S(O)$_m$(CR$^5$R$^6$)$_n$—;

wherein each of m, n and p is a number independently selected from 0, 1 and 2;

wherein R$^1$ is selected from aryl and heteroaryl, wherein R$^1$ is optionally substituted at a substitutable position with one or more radicals selected from alkoxy, aminoalkoxy optionally substituted on the nitrogen atom with alkyl, cycloalkyl and aralkyl, cyano, nitro, hydroxyl, alkyl, halo, haloalkyl, haloalkoxy, cycloalkylalkoxy, carboxyl, acyl, alkanoyl, aminocarbonyl, alkylaminocarbonyl, aralkoxy, alkenyloxy, alkynyloxy, aminosulfonyl, alkylaminosulfonyl, alkylsulfonylamino, heterocyclo, aralkyl, heteroaralkyl, alkoxycarbonyl, heteroaryl, alkylthio, alkylsulfinyl, alkylsulfonyl, alkenylthio, arylthio, aralkylthio, cycloalkylthio, and amino optionally substituted with a radical selected from alkyl, aralkyl, aryl, alkenyl, alkynyl, cycloalkyl, acyl, cycloalkenyl, hydroxyalkyl, alkylcarbonyl, alkoxycarbonyl, alkoxyalkyl and arylcarbonyl wherein the aryl ring may be further substituted with one or more radicals selected from alkyl, halo, alkoxy, aminocarbonyl and hydrazidylcarbonyl;

wherein each of R$^3$, R$^4$, R$^5$ and R$^6$ is independently selected from hydrido, alkyl, aryl and aralkyl; or wherein R$^3$ and R$^4$, or R$^5$ and R$^6$ together form cycloalkyl;

wherein R$^7$ is one or more radicals selected from alkoxy, amino, cyano, nitro, hydroxyl, alkyl, cycloalkyl, halo, haloalkyl, haloalkoxy, carboxyl, alkanoyl, acyl, alkylamino, arylamino, alkylarylamino, alkanoylamino, alkylaminoalkyl, aminocarbonyl, alkylaminocarbonyl, alkoxycarbonyl, aryloxycarbonyl, aralkoxycarbonyl, alkylcarbonyl, cycloalkylcarbonyl, alkylcarbonylalkyl, alkoxycarbonylalkyl, alkylcarbonylamino, aminocarbonyloxy, aryloxy, aralkoxy, alkenyloxy, alkynyloxy, acyloxy, cycloalkylalkoxy, aralkyl, aryl, aroyl, alkoxyalkyl, hydroxyalkyl, heterocyclo, heteroaralkyl, alkylthio, alkylsulfinyl, alkylsulfonyl, arylthio, arylsulfinyl, alkylsulfonyl, alkylsulfonylamino, aminosulfonyl and alkylaminosulfonyl; or wherein R$^5$ and R$^8$ taken together form a ring; and wherein R$^8$ is selected from hydrido, alkyl, alkenyl, hydroxyalkyl, acyl, alkoxyalkyl, cycloalkyl, aryl, aryloxyalkyl, alkylthioalkyl, aralkyl, alkoxycarbonyl, aminocarbonyl, alkanoyl, alkylaminocarbonyl and alkylsulfonyl; provided that when m is 0, R$^8$ is not 1-(β-D-ribofuranosyl)benzimidazole;

or a pharmaceutically acceptable salt thereof.

A preferred class of compounds consists of those compounds of Formula II wherein R$^1$ is selected from phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidyl, thienopyridinyl, dihydrothienopyridinyl, carbostyryl, pyrimidyl and pyrazinyl, wherein R$^1$ is optionally substituted at a substitutable position with one or more radicals selected from lower alkoxy, lower aminoalkoxy optionally substituted on the nitrogen atom with lower alkyl, lower cycloalkyl and lower aralkyl, cyano, nitro, hydroxyl, lower alkyl, halo, lower haloalkyl, lower haloalkoxy, lower cycloalkylalkoxy, carboxyl, acyl, lower alkanoyl, aminocarbonyl, lower alkylaminocarbonyl, lower aralkoxy, lower alkenyloxy, lower alkynyloxy, aminosulfonyl, lower alkylaminosulfonyl, lower alkylsulfonylamino, 5 to 20 membered heterocyclo, lower aralkyl, lower heteroaralkyl, lower alkoxycarbonyl, 5 to 8 membered heteroaryl, lower alkylthio, lower alkylsulfinyl, lower alkylsulfonyl, lower alkenylthio, lower arylthio, lower aralkylthio, lower cycloalkylthio, and amino optionally substituted with a radical selected from lower alkyl, lower aralkyl, phenyl, lower alkenyl, lower alkynyl, lower cycloalkyl, acyl, lower cycloalkenyl, lower hydroxyalkyl, lower alkylcarbonyl, lower alkoxycarbonyl, lower alkoxyalkyl and phenylcarbonyl wherein the phenyl ring may be further substituted with one or more radicals selected from lower alkyl, halo, lower alkoxy, aminocarbonyl and hydrazidylcarbonyl; wherein each of R$^3$, R$^4$, R$^5$ and R$^6$ is independently selected from hydrido, lower alkyl, phenyl, naphthyl and lower aralkyl; or wherein R$^3$ and R$^4$, or R$^5$ and R$^6$ together form lower cycloalkyl; wherein R$^7$ is one or more radicals selected from lower alkoxy, amino, cyano, nitro, hydroxyl, lower alkyl, lower cycloalkyl, halo, lower haloalkyl, lower haloalkoxy, carboxyl, lower alkanoyl, acyl, lower alkylamino, lower arylamino, lower alkylarylamino, lower alkanoylamino, lower alkylaminoalkyl, aminocarbonyl, lower alkylaminocarbonyl, lower alkoxycarbonyl, lower aryloxycarbonyl, lower aralkoxycarbonyl, lower alkylcarbonyl, lower cycloalkylcarbonyl, lower alkylcarbonylalkyl, lower alkoxycarbonylalkyl, lower alkylaminocarbonyl, aminocarbonyloxy, lower aryloxy, lower aralkoxy, lower alkenyloxy, lower alkynyloxy, acyloxy, lower cycloalkylalkoxy, lower aralkyl, optionally substituted lower aryl, lower aroyl, lower alkoxyalkyl, hydroxyalkyl, 5 to 20 membered heterocyclo, lower heteroaralkyl, lower alkylthio, lower alkylsulfinyl, lower alkylsulfonyl, lower arylthio, lower arylsulfinyl, lower arylsulfonyl, lower alkylsulfonylamino, aminosulfonyl and lower alkylaminosulfonyl; or wherein R$^5$ and R$^8$ taken together form a ring; and wherein R$^8$ is selected from hydrido, lower alkyl, lower alkenyl, lower hydroxyalkyl, acyl, lower alkoxyalkyl, phenyl, naphthyl, lower aryloxyalkyl, lower alkylthioalkyl, lower aralkyl, lower alkoxycarbonyl, aminocarbonyl, lower alkanoyl, lower alkylaminocarbonyl and lower alkylsulfonyl; or a pharmaceutically acceptable salt thereof.

A class of compounds of particular interest consists of those compounds of Formula II wherein R$^1$ is optionally substituted at a substitutable position with one or more radicals selected from methoxy, ethoxy, propoxy, butoxy, isopropoxy, tert-butoxy, aminoethoxy optionally substituted on the nitrogen atom with methyl, ethyl, propyl, butyl, pentyl, isopropyl, isobutyl, tert-butyl, cyclohexyl, cyclopropyl and benzyl, amino optionally substituted with a radical selected from methyl, ethyl, propyl, butyl, pentyl, isopropyl, isobutyl, tert-butyl, benzyl, phenethyl, phenyl, butene, pentene, isopropylene, isobutylene, propargyl, cyclopropyl, cyclobutyl, cyclopentyl, cyclohexyl, formyl, acetyl, cyclobutenyl, cyclopentenyl, cyclohexenyl, hydroxymethyl, methylcarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methoxymethyl, and phenylcarbonyl wherein the phenyl ring may be further substituted with one or more radicals selected from methyl, chloro, methoxy, aminocarbonyl and hydrazidylcarbonyl, cyano, nitro, hydroxyl, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, cyclohexylmethoxy, carboxyl, formyl, acetyl, propionyl, aminocarbonyl, methylaminocarbonyl, dimethylaminocarbonyl, benzyloxy, aminosulfonyl, dimethylaminosulfonyl, methylsulfonylamino, morpholinyl, pyrrolidinyl, piperazinyl, piperidyl, phthalimidyl, benzyl, methoxycarbonyl, ethoxycarbonyl, pyridyl, methylthio, methylsulfinyl, methylsulfonyl, phenylthio, benzylthio, and cyclohexylthio; wherein each of $R^3$, $R^4$, $R^5$ and $R^6$ is independently selected from hydrido, methyl, ethyl, propyl, butyl, pentyl, isopropyl, isobutyl, tert-butyl, phenyl and benzyl; or wherein $R^3$ and $R^4$, or $R^5$ and $R^6$ together form cyclopropyl, cyclobutyl or cyclopentyl; wherein $R^7$ is one or more radicals selected from methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, cyclohexyl, cyclopropyl, cyclobutyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, trifluoroethoxy, carboxyl, formyl, acetyl, propionyl, butyryl, N-methylamino, N-ethylamino, N-propylamino, N-butylamino, N-tert-butylamino, N-pentylamino, N-hexylamino, N,N-dimethylamino, phenylamino, N-methy-N-phenylamino, methylaminomethyl, aminocarbonyl, N-methylaminocarbonyl, N,N-dimethylaminocarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, phenoxycarbonyl, benzyloxycarbonyl, methylcarbonyl, cyclohexylcarbonyl, methylcarbonylmethyl, methoxycarbonylmethyl, N,N-dimethylaminocarbonyl, aminocarbonyloxy, phenoxy, benzoxy, benzyl, phenethyl, phenyl, benzoyl, methoxymethyl, hydroxymethyl, morpholinyl, pyrrolidinyl, piperazinyl, piperidyl, methylthio, ethylthio, methylsulfinyl, ethylsulfinyl, methylsulfonyl, phenylthio, phenylsulfinyl, phenylsulfonyl, aminosulfonyl, methylsulfonylamino, methylaminosulfonyl and N,N-dimethylaminosulfonyl; or wherein $R^5$ and $R^8$ taken together form a ring; and wherein $R^8$ is selected from hydrido, methyl, ethyl, propyl, butyl, pentyl, isopropyl, isobutyl, tert-butyl, butene, pentene, isopropylene, isobutylene, hydroxymethyl, phenyl, naphthyl, phenoxymethyl, methylthiomethyl, benzyl, phenethyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methoxymethyl, aminocarbonyl, formyl, acetyl, propionyl, butyryl, methylaminocarbonyl and methylsulfonyl; or a pharmaceutically acceptable salt thereof.

A family of specific compounds of particular interest within Formula II consists of compounds, and their pharmaceutically acceptable salts, of the group selected from:

2-[(4,6-dimethyl-5-methoxy-2-phthalimidylphenyl) methylsulfonyl]-5-methoxy-1H-benzimidazole;
2-[[(5-chloro-1H-benzimidazol-2-yl)sulfinyl]methyl]-3,5-dimethyl-4-methoxybenzenamine;
(+)-2-[[(5-methoxy-1H-benzimidazol-2-yl)sulfinyl] methyl]-3,5-dimethyl-4-methoxybenzenamine;
(-)-2-[[(5-methoxy-1H-benzimidazol-2-yl)sulfinyl] methyl]-3,5-dimethyl-4-methoxybenzenamine;
N-[2-[[(6-methoxy-1H-benzimidazol-2-yl)sulfinyl]methyl]-3,5-dimethyl-4-methoxyphenyl]acetamide;
2-[(4,6-dimethyl-5-methoxy-2-phthalimidylphenyl) methylsulfinyl]-6-chloro-1-isopropyl-1H-benzimidazole;
2-[(4,6-dimethyl-5-methoxy-2-phthalimidylphenyl) methylsulfinyl]-5-chloro-1-isopropyl-1H-benzimidazole;
2-[(4,6-dimethyl-5-methoxy-2-phthalimidylphenyl) methylsulfinyl]-5-chloro-1-ethyl-1H-benzimidazole;
2-[(4,6-dimethyl-5-methoxy-2-phthalimidylphenyl) methylsulfinyl]-6-chloro-1-ethyl-1H-benzimidazole;
2-[[[2-[[(6-chloro-1-ethyl-1H-benzimidazol-2-yl)sulfinyl] methyl]-3,5-dimethyl-4-methoxyphenyl]amino]carbonyl] benzenecarboxylic acid hydrazide;
2-[[[2-[[(5-chloro-1-ethyl-1H-benzimidazol-2-yl)sulfinyl] methyl]-3,5-dimethyl-4-methoxyphenyl]amino]carbonyl] benzenecarboxylic acid hydrazide;
3-[[(1H-benzimidazol-2-yl)sulfinyl]methyl]benzenamine;
2-[[3-methylpyridin-2-ylmethyl]sulfinyl]-1H-benzimidazole;
2-[(imidazo[1,2-a]pyridin-3-yl)methylsulfinyl]-1H-benzimidazole;
2-[(imidazo[1,2-a]pyridin-3-yl)methylsulfinyl]-1H-benzimidazole;
2-[(imidazo[1,2-a]pyridin-3-yl)methylsulfinyl]-5-methyl-1H-benzimidazole;
2-[(imidazo[1,2-a]pyridin-3-yl)methylsulfinyl]-5-methoxy-1H-benzimidazole;
5-chloro-2-[(imidazo[1,2-a]pyridin-3-yl)methylsulfinyl]-1H-benzimidazole;
2-[(imidazo[1,2-a]pyridin-3-yl)methylsulfinyl]-5-trifluoromethyl-1H-benzimidazole;
2-[(imidazo[1,2-a]pyridin-8-yl)methylsulfinyl]-1H-benzimidazole;
2-[(imidazo[1,2-a]pyridin-8-yl)methylsulfinyl]-1H-benzimidazole;
2-[(imidazo[1,2-a]pyridin-8-yl)methylsulfinyl]-5-methoxy-1H-benzimidazole;
5-ethoxy-2-((imidazo[1,2-a]pyridin-8-yl)methylsulfinyl]-1H-benzimidazole;
2-[(imidazo[1,2-a]pyridin-8-yl)methylsulfinyl]-4-methyl-1H-benzimidazole;
2-[(imidazo[1,2-a]pyridin-8-yl)methylsulfinyl]-5-methyl-1H-benzimidazole;
2-[(imidazo[1,2-a]pyridin-8-yl)methylsulfinyl]-5,6-dimethyl-1H-benzimidazole;
2-[(imidazo[1,2-a]pyridin-8-yl)methylsulfinyl]-5,6-dimethoxy-1H-benzimidazole;
5-chloro-2-[(imidazo[1,2-a]pyridin-8-ylmethyl)sulfinyl]-1H-benzimidazole;
2-[(imidazo[1,2-a]pyridin-8-yl)methylsulfinyl]-5-trifluoromethyl-1H-benzimidazole;
2-[[(2,3-dimethylimidazo[1,2-a]pyridin-8-yl)methyl] sulfinyl]-1H-benzimidazole;
2-[[(3-methylimidazo[1,2-a]pyridin-8-yl)methyl]sulfinyl]-1H-benzimidazole;
2-2-[[(2-phenylimidazo[1,2-a]pyridin-8-yl)methyl] sulfinyl]-1H-benzimidazole;
2-[[(3-phenylimidazo[1,2-a]pyridin-8-yl)methyl]sulfinyl]-1H-benzimidazole;
2-[[(3-(4-nitrophenyl)imidazo[1,2-a]pyridin-8-yl)methyl] sulfinyl]-1H-benzimidazole;
2-[[[3-[3-(trifluoromethyl)phenyl]imidazo[1,2-a]pyridin-8-yl]methyl]sulfinyl]-1H-benzimidazole;
5-methyl-2-[[[3-[3-(trifluoromethyl)phenyl]imidazo[1,2-a] pyridin-8-yl]methyl]sulfinyl]-1H-benzimidazole;
5-chloro-2-[[[3-[3-(trifluoromethyl)phenyl]imidazo[1,2-a] pyridin-8-yl]methyl]sulfinyl]-1H-benzimidazole;
2-[[[3-[4-(trifluoromethyl)phenyl]imidazo[1,2-a]pyridin-8-yl]methyl]sulfinyl]-1H-benzimidazole;
5-chloro-2-[[[3-[4-(trifluoromethyl)phenyl]imidazo[1,2-a] pyridin-8-yl]methyl]sulfinyl]-1H-benzimidazole;

4-[8-[ (1H-benzimidazol-2-yl) sulfinylmethyl]imidazo[1,2-a]pyridin-3-yl]benzoate;
2-[[[3-(4-chlorophenyl)imidazo[1,2-a]pyridin-8-yl]methyl]sulfinyl]-1H-benzimidazole;
2-[[[3-(4-methylphenyl)imidazo[1,2-a]pyridin-8-yl]methyl]sulfinyl]-1H-benzimidazole;
2-[(imidazo[1,2-a]pyridin-5-yl)methylsulfinyl]-1H-benzimidazole;
4,6-dimethyl-2-(((imidazo(1,2-a)pyridin-2-yl)methyl)thio)-1H-benzimidazole;
2-[3-methyl-4-(2-(N-benzyl-N-cyclohexylamino)-ethoxy)pyridyl]methylthio-1H-benzimidazole;
ethyl 2-[(1H-benzimidazol-2-yl)thiomethyl]-4-methyl-amino-5-pyrimidine carboxylate;
2-(5-fluoro-2-(4-methoxy-2-pyridyl)-phenylsulfinyl)-1H-benzimidazole;
5-difluoromethoxy-2-(((3,4-dimethoxy-2-pyridinyl)methyl)sulfinyl)-1H-benzimidazole;
2-(((4-difluoromethoxy-3-methyl-2-pyridyl)methylsulfinyl)benzimidazole;
2-((6-azachroman-5-yl)methylsulfinyl)-benzimidazole;
5-carbomethoxy-6-methyl-2-(((3,4-dimethoxy-2-pyridinyl)methyl)sulfinyl-1H-benzimidazole;
5-carbomethoxy-6-methyl-2-(((3,4-dimethoxy-2-pyridinyl)methyl)sulfinyl)-1H-benzimidazol-1-yl-methyl ethyl carbonate;
2-((3-methyl-4-(2,2,2-trifluoroethoxy)-2-pyridyl)methylsulfinyl)benzimidazole;
4-fluoro-2-(((4-methoxy-2-pyridinyl)methyl)sulfinyl-1H-benzimidazol-1-yl-methyl-ethylcarbonate;
2-[3-methyl-4-(1-benzyl-4-piperidyl)oxy-2-pyridyl]methylthio-1H-benzimidazole;
2-(3-methyl-4-(2-(N-methyl-N-(4-methyl-benzyl)amino)ethoxy)-2-pyridyl)methylsulfonyl-1H-benzimidazole;
2-(4-methoxy-6-methyl-2-pyrimidinyl)methylthio-1H-benzimidazole;
5-chloro-2-(3,4-dimethoxy-2-pyridylmethylsulfinyl)-1H-benzimidazole;
5-fluoro-2-(4-cyclopropylmethoxy-2-pyridylmethylsulfinyl)-1H-benzimidazole;
4-fluoro-2-(4-methoxy-2-pyridylmethylsulfinyl)-1H-benzimidazole;
2-(((4-methoxy-3,5-dimethyl-2-pyridyl)-methyl)-sulfinyl)-5-methoxy-1H-benzimidazole;
5-hydroxymethyl-2-((3,5-dimethyl-4-methoxy-2-pyridyl)methylthio-1H-benzimidazole;
2-(4-ethylthio-3-methylpyrid-2-yl-methyl)sulfinyl-benzimidazole;
2-(((4-(2-benzyloxyethoxy)-3-methyl-2-pyridyl)methylthio)benzimidazole;
2-[[2-[N-(2-hydroxyethyl)-N-methylamino]-5-methoxy]benzylsulfinyl]benzimidazole;
2-(5-benzyl-4-chloro-6-methyl-2-pyrimidinyl)methylthio-1H-benzimidazole;
5-carboethoxy-6-methyl-2-(((3-methyl-2-pyridyl)methyl)sulfinyl)-1H-benzimidazole;
5-(2-benzimidazolylsulfinylmethyl)-3,4-dihydro-4-methyl-2H-1,4-benzoxazine;
2-(3-methyl-4-(2-(N-benzyl-N-methylamino)ethoxy-2-pyridyl)methylsulfinyl-1H-benzimidazole;
2-(3-methyl-4-(2-(1,2,3,4-tetrahydroisoquinolin-2-yl)-ethoxy)-2-pyridyl)methylsulfinyl-1H-benzimidazole;
2-[1-(3,5-dimethylpyrazolyl)]methylthiobenzimidazole;
2-(3-chloro-4-methoxy-2-picolylthio)-5-methoxy-1H-benzimidazole;
2-(4-(2-ethoxyethoxy)-3-methyl-2-pyridyl)methylsulfinyl-1H-benzimidazole;
2-(3-methylthieno(2,3-c)pyridin-7-yl)methylsulfinyl)-benzimidazole;
2-(2-dimethylamino-5-methoxybenzylsulfinyl)-5-methoxy-benzimidazole;
2-(2-dimethylamino-5-methylbenzylsulfinyl)-5-methoxybenzimidazole;
2-[4-(2,3,5-trimethyl)pyridylthio]-5-methoxybenzimidazole;
2-[(2-(4-chlorophenyl)-5-methylimidazol-4-yl)methylthio]benzimidazole;
2-(5-hydroxy-1H-benzimidazol-2-ylsulfinylmethyl)-N,N-dimethylbenzenamine;
2-((6-methoxyisoquinolin-1-yl)methylsulfinyl)benzimidazole;
3-(5-methoxy-1H-benzimidazol-2-yl)thiomethylcarbostyril;
5-methoxy-2-(4-dimethylamino-5-fluoro-2-pyridylmethylsulfinyl)-1H-benzimidazole;
2-(2-dimethylaminobenzylsulfinyl)-5-cyclopropylmethoxybenzimidazole;
2-(3,5-dimethyl-2-pyridylmethylsulfinyl)-5-cyclopropylmethoxy-benzimidazole;
2-[2-(N-cyclohexyl-N-methylamino)benzylsulfonyl]benzimidazole;
8-(5-fluoro-6-methoxy-2-benzimidazolyl)sulfinylmethyl-1-ethyl-4-(N-methyl-N-allyl)amino-1,2,3,4-tetrahydroquinoline;
2-(2-benzyloxycarbonylaminobenzylthio)benzimidazole;
2-(2-benzimidazolylmethylthio)pyrimidine;
5-acetyl-2-((2-dimethylaminobenzyl)sulfinyl)benzimidazole;
2-((3,5-dimethyl-4-methoxy-2-pyridyl)methylsulfinyl)-5-fluoro-1H-benzimidazole;
2-(3-pyridylmethylthio)-5-methoxybenzimidazole;
2-(2-methylaminobenzylsulfinyl)benzimidazole;
5-methoxy-2-(2-dimethylaminobenzylsulfinyl)-1H-benzimidazole;
2-(3,4-dimethoxypyrid-2-ylmethylsulfinyl)-5-trifluoromethyl-benzimidazole;
5-methoxy-2-(4-piperidino-2-pyrimidinylmethylsulfinyl)-(1H)-benzimidazole;
2-[2-(4-benzyloxy)-pyridylmethylsulfinyl]benzimidazole;
4-allyloxy-8-(2-benzimidazolyl)thio-3-methyl-5,6,7,8-tetrahydroquinoline;
2-[2-(4-methoxy-5-n-pentyl)-pyridylmethylthio]benzimidazole;
2-(5-bromo-4-piperidino-2-pyridylmethylsulfinyl)-5-methoxy-(1H)-benzimidazole;
2-((3,5-dimethyl-4-morpholinopyrid-2-yl)methylsulfinyl)benzimidazole;
2-((2-pyridinylmethyl)sulfinyl)-1H-benzimidazole-1-methanol;
2-((3,4-dihydro-2H-thieno(3,2-c)pyridinylmethyl)thio)-1H-benzimidazole-1-methanol;
2-(4-isopropoxy-2-pyridyl)methylsulfinylbenzimidazole;
2-((4-fluorobenzyloxy-3-methyl-2-pyridyl)methylsulfinyl)benzimidazole;
2-(2-aminobenzylsulfinyl)-benzimidazole;
N,N-dimethyl-2-(1H-benzimidazol-2-yl-sulfinylmethyl)benzenamine;
2-[(4,5-dimethoxy-2-pyridyl)methylsulfinyl]-5-trifluoromethoxy-1H-benzimidazole;
2-((4-morpholinyl-3-ethylpyridin-2-yl)methylsulfinyl)-5-trifluoromethylbenzimidazole;
2-((4-methoxy-2-pyridyl)methylsulfinyl)-5-trifluoromethoxy-1H-benzimidazole;
5-cyclopropylcarbonyl-2-((4-methoxy-2-pyridyl)methylsulfinyl)-1H-benzimidazole;

2-[2-(3,5-dimethyl-4-methoxy)-pyridylmethylsulfinyl]-(5-chloro)-benzimidazole;
2-[2-(4,5-dimethyl)-pyridylmethylsulfinyl]-(5-acetyl-6-methyl)-benzimidazole;
2-[2-(3,5-dimethyl)pyridylmethylsulfinyl]5-fluorobenzoxazole;
3-[(4-dimethylamino-2-pyridyl) methylthio]indole;
6-benzoylamino-7-chloro-2-(((3,5-dimethyl-4-methoxy-2-pyridyl)-methyl)thio)benzothiazole;
5-(4,5-dihydro-2-oxazolyl)-2-((3,5-dimethyl-4-methoxy-2-pyridyl)methylthio)-1H-benzimidazole;
2-gernaylthio-benzimidazole;
ethyl 2-((1H-benzimidazol-2-yl)-sulfinylmethyl)-4-dimethylamino-5-pyrimidinecarboxylate;
2-[(1H-benzimidazol-2-yl)sulfinylmethyl]benzenamine;
2-[(1H-benzimidazol-2-yl)sulfinylmethyl]N,N-dimethylbenzenamine;
N-[2-[(1H-benzimidazol-2-yl)sulfinylmethyl]phenyl]acetamide;
2-[[(4-methyl-1H-benzimidazol-2-yl)sulfinyl]methyl]benzenamine;
2-[[(5,6-dimethyl-1H-benzimidazol-2-yl)sulfinylmethyl]benzenamine;
2-[[(5-methoxy-1H-benzimidazol-2-yl)sulfinyl]methyl]benzenamine;
methyl 2-[[(2-aminophenyl)methyl]sulfinyl]-5-methoxy-1H-benzimidazole-6-carboxylate;
2-[(1H-benzimidazol-2-yl)sulfinylmethyl]-4-chlorobenzenamine;
2-[(1H-benzimidazol-2-yl)sulfinylmethyl]-5-chlorobenzenamine;
2-[(1H-benzimidazol-2-yl)sulfinylmethyl]-4-methoxybenzenamine;
2-[(1H-benzimidazol-2-yl)sulfinylmethyl]-6-methoxybenzenamine;
2-[(1H-benzimidazol-2-yl)sulfinylmethyl]-3-methylbenzenamine;
2-[(1H-benzimidazol-2-yl)sulfinylmethyl]-4-methylbenzenamine;
2-[(1H-benzimidazol-2-yl)sulfinylmethyl]-6-methylbenzenamine;
2-[(1H-benzimidazol-2-yl)sulfinylmethyl]-4,6-dimethylbenzenamine;
2-[(1H-benzimidazol-2-yl)sulfinylmethyl]-N-methylbenzenamine;
2-[[(5-methoxy-1H-benzimidazol-2-yl)sulfinyl]methyl]-4-methylbenzenamine;
2-[[(5-methoxy-1H-benzimidazol-2-yl)sulfinyl]methyl]-6-methylbenzenamine;
2-[(1H-benzimidazol-2-yl)sulfinylmethyl]-4-ethylbenzenamine;
2-[(1H-benzimidazol-2-yl)sulfinylmethyl]-6-ethylbenzenamine;
2-[(1H-benzimidazol-2-yl)sulfinylmethyl]-4-methoxy-3,5-dimethylbenzenamine;
2-[[(5-methyl-1H-benzimidazol-2-yl)sulfinyl]-methyl]benzenamine;
2-2-[[(5-chloro-1H-benzimidazol-2-yl)sulfinyl]-methyl]benzenamine;
2-[[(5-ethoxy-1H-benzimidazol-2-yl)sulfinyl]-methyl]benzenamine;
2-[[[(5-(trifluoromethyl)-1H-benzimidazol-2-yl]sulfinyl]methyl]benzenamine;
2-[(1H-benzimidazol-2-yl)sulfinylmethyl]-4-(trifluoromethyl)benzenamine;
2-[(1H-benzimidazol-2-yl)sulfinylmethyl]-4-butylbenzenamine;
2-[(1H-benzimidazol-2-yl)sulfinylmethyl]-5,6-dimethylbenzenamine;
2-[(1H-benzimidazol-2-yl)sulfinylmethyl]-3,6-dimethylbenzenamine;
2-[(1H-benzimidazol-2-yl)sulfinylmethyl]-4-chloro-6-methylbenzenamine;
2-[(1H-benzimidazol-2-ylsulfinymethyl]-4-chloro-6-methoxy-3-methylbenzenamine;
2-[[(5-ethoxy-1H-benzimidazol-2-yl)sulfinyl]-methyl]-4-methylbenzenamine;
2-[[(5-methyl-1H-benzimidazol-2-yl)sulfinyl]-methyl]-5,6-dimethylbenzenamine;
2-[[[(5-(trifluoromethy)l-1H-benzimidazol-2-yl]sulfinyl]-3,6-dimethylbenzenamine;
2-[[[(5-(trifluoromethyl)l-1H-benzimidazol-2-yl]sulfinyl]methyl]-6-methoxybenzenamine;
methyl 2-amino-3-[(1H-benzimidazol-2-yl)sulfinylmethyl]benzoate;
ethyl 4-amino-3-[(1H-benzimidazol-2-ylsulfinyl)methyl]benzoate;
ethyl 4-amino-3-[[(5-methoxy-1H-benzimidazol-2-yl)sulfinyl]methyl]benzoate;
2-[[5,6-dimethoxy-1H-benzimidazol-2-yl)sulfinyl]methyl]-4-methylbenzenamine;
2-[(1H-benzimidazol-2-yl)sulfinylmethyl]-4-fluorobenzenamine;
2-[(1H-benzimidazol-2-yl)sulfinylmethyl]-3,4,5-trimethylbenzenamine;
2-2-[[(5-methoxy-1H-benzimidazol-2-yl)sulfinyl]methyl]-4-methoxy-3,5-dimethylbenzenamine;
3-[(1H-benzimidazol-2-yl)sulfinylmethyl]benzenamine;
3-[(1H-benzimidazol-2-yl)sulfinylmethyl]-2-pyridinamine;
3-[(1H-benzimidazol-2-yl)sulfinylmethyl]-N,N-dimethyl-2-pyridinamine;
6-((1H-benzimidazol-2-yl)sulfinylmethyl]-2-pyridinamine;
6-[[(4-methyl-1H-benzimidazol-2-yl)-sulfinyl]methyl]-2-pyridinamine;
6-[[(5-methyl-1H-benzimidazol-2-yl)-sulfinyl]methyl]-2-pyridinamine;
6-[[(5-methoxy-1H-benzimidazol-2-yl)sulfinyl]-methyl]-2-pyridinamine;
6-[[(5-chloro-1H-benzimidazol-2-yl)-sulfinyl]methyl]-2-pyridinamine;
6-[[[5-(trifluoromethyl)-1H-benzimidazol-2-yl]sulfinyl]methyl]-2-pyridinamine;
6-[[(5-ethoxy-1H-benzimidazol-2-yl)-sulfinyl]methyl]-2-pyridinamine;
6-[[(5,6-dimethoxy-1H-benzimidazol-2-yl)-sulfinyl]methyl]-2-pyridinamine;
6-[[(5,6-dimethyl-1H-benzimidazol-2-yl)-sulfinyl]methyl]-2-pyridinamine;
6-[[(4,6-dimethyl-1H-benzimidazol-2-yl)-sulfinyl]methyl]-2-pyridinamine;
6-[[[5-(hydroxymethyl)-1H-benzimidazol-2-yl]sulfinyl]methyl]-2-pyridinamine;
6-[(1H-benzimidazol-2-yl)sulfinylmethyl]-N-(2,2-dimethylpropyl)-2-pyridinamine;
6-[(1H-benzimidazol-2-yl)sulfinylmethyl]-N-ethyl-2-pyridinamine; and
5-[(1H-benzimidazol-2-yl)sulfinylmethyl]-2-pyridinamine.

Within Formula I there is a second subclass of compounds of high interest which can be used to treat viral infection by inhibiting viral proteases, represented by Formula III:

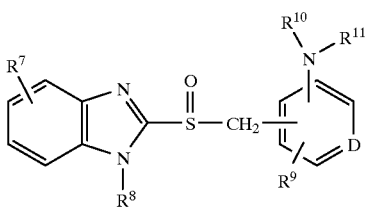
III wherein D is N or CH; wherein $R^7$ is one or more radicals selected from hydrido, alkoxy, amino, cyano, nitro, hydroxyl, alkyl, halo, haloalkyl, carboxyl, alkanoyl, nitro, amino, alkylamino, aminocarbonyl, alkylaminocarbonyl, alkylcarbonylamino, aminosulfonyl, alkylaminosulfonyl, alkylsulfonylamino, alkoxycarbonyl, alkylthio, alkylsulfinyl and alkylsulfonyl; wherein R8 is selected from hydrido, alkyl and cycloalkyl; wherein $R^9$ is one or more radicals selected from hydrido, alkoxy, amino, alkyl, halo, cyano, nitro, hydroxyl, haloalkyl, carboxyl, alkanoyl, nitro, alkylamino, dialkylamino, aminocarbonyl, alkylaminocarbonyl, alkylcarbonylamino, aminosulfonyl, alkylaminosulfonyl, alkylsulfonylamino, alkoxycarbonyl, alkylthio, alkylsulfinyl and alkylsulfonyl; and wherein $R^{10}$ and $R^{11}$ are independently selected from hydrido, alkyl, aryl, alkylcarbonyl and arylcarbonyl wherein the aryl ring may be further substituted with one or more radicals selected from alkyl, halo, alkoxy, aminocarbonyl and hydrazidylcarbonyl, or wherein $R^{10}$ and $R^{11}$ together with the nitrogen atom form a heterocyclic ring; or a pharmaceutically acceptable salt thereof.

A preferred class of compounds consists of those compounds of Formula III wherein $R^7$ is one or more radicals selected from hydrido, lower alkoxy, amino, cyano, nitro, hydroxyl, lower alkyl, halo, lower haloalkyl, carboxyl, lower alkanoyl, lower alkylamino, aminocarbonyl, lower alkylaminocarbonyl, alkylcarbonylamino, aminosulfonyl, alkylaminosulfonyl, alkylsulfonylamino, lower alkoxycarbonyl, lower alkylthio, lower alkylsulfinyl and lower alkylsulfonyl; wherein $R^8$ is selected form hydrido, lower alkyl and lower cycloalkyl; wherein $R^9$ is one or more radicals selected from hydrido, lower alkoxy, amino, lower alkyl, halo, cyano, nitro, hydroxyl, lower haloalkyl, carboxyl, lower alkanoyl, lower alkylamino, aminocarbonyl, lower alkylaminocarbonyl, lower alkylcarbonylamino, aminosulfonyl, lower alkylaminosulfonyl, lower alkylsulfonylamino, lower alkoxycarbonyl, lower alkylthio, lower alkylsulfinyl and lower alkylsulfonyl; and wherein $R^{10}$ and $R^{11}$ are independently selected from hydrido, phenyl, lower alkylcarbonyl, lower alkyl and phenylcarbonyl wherein the phenyl ring may be further substituted with one or more radicals selected from lower alkyl, halo, lower alkoxy, aminocarbonyl and hydrazidylcarbonyl, or wherein $R^{10}$ and $R^{11}$ together with the nitrogen atom form a heterocyclic ring; or a pharmaceutically acceptable salt thereof.

A class of compounds of particular interest consists of those compounds of Formula III wherein $R^7$ is one or more radicals selected from hydrido, methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxyl, formyl, acetyl, propionyl, N-methylamino, N-ethylamino, N-propylamino, N-butylamino, N-tert-butylamino, N-pentylamino, N-hexylamino, N,N-dimethylamino, aminocarbonyl, N-methylaminocarbonyl, N,N-dimethylaminocarbonyl, methylcarbonylamino, aminosulfonyl, methylaminosulfonyl, methylsulfonylamino, methoxycarbonyl, ethoxycarbonyl, isopropoxycarbonyl, tert-butoxycarbonyl, propoxycarbonyl, n-butycarbonyl, isobutoxycarbonyl, pentoxycarbonyl, methylthio, methylsulfinyl and methylsulfonyl; wherein $R^8$ is selected from hydrido, methyl, ethyl, propyl, butyl, pentyl, isopropyl, isobutyl, tert-butyl, cyclopropyl, cyclobutyl and cyclopentyl; wherein $R^9$ is one or more radicals selected from hydrido, methoxy, ethoxy, propoxy, butoxy, isopropoxy, tert-butoxy, amino, methyl, ethyl, propyl, butyl, pentyl, isopropyl, isobutyl, tert-butyl, fluoro, chloro, bromo, iodo, cyano, nitro, hydroxyl, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxyl, formyl, acetyl, propionyl, N-methylamino, N-ethylamino, N-propylamino, N-butylamino, N-tert-butylamino, N-pentylamino, N-hexylamino, N,N-dimethylamino, aminocarbonyl, N-methylaminocarbonyl, N,N-dimethylaminocarbonyl, aminosulfonyl, methylaminosulfonyl, methylsulfonylamino, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methylthio, methylsulfinyl and methylsulfonyl; and wherein $R^{10}$ and $R^{11}$ are independently selected from hydrido, methyl, ethyl, propyl, butyl, pentyl, isopropyl, isobutyl, tert-butyl, phenyl, methylcarbonyl and phenylcarbonyl wherein the phenyl ring may be further substituted with one or more radicals selected from methyl, chloro, methoxy, aminocarbonyl and hydrazidylcarbonyl, or wherein $R^{10}$ and $R^{11}$ together with the nitrogen atom form phthalimidyl, morpholinyl, and piperazinyl; or a pharmaceutically acceptable salt thereof.

A family of specific compounds of particular interest within Formula III consists of compounds, and their pharmaceutically acceptable salts, of the group selected from:

2-[[[(5-chloro-1H-benzimidazol-2-yl)sulfinyl]methyl]-3,5-dimethyl-4-methoxybenzenamine;

(−)-2-[[[(5-methoxy-1H-benzimidazol-2-yl)sulfinyl]methyl]-3,5-dimethyl-4-methoxybenzenamine;

(+)-2-[[[(5-methoxy-1H-benzimidazol-2-yl)sulfinylmethyl]-3,5-dimethyl-4-methoxybenzenamine;

N-[2-[[[(6-methoxy-1H-benzimidazol-2-yl)sulfinyl]methyl]-3,5-dimethyl-4-methoxyphenyl]acetamide;

2-[(4,6-dimethyl-5-methoxy-2-phthalimidylphenyl) methylsulfinyl]-6-chloro-1-isopropyl-1H-benzimidazole;

2-[(4,6-dimethyl-5-methoxy-2-phthalimidylphenyl) methylsulfinyl]-5-chloro-1-isopropyl-1H-benzimidazole;

2-[(4,6-dimethyl-5-methoxy-2-phthalimidylphenyl) methylsulfinyl]-5-chloro-1-ethyl-1H-benzimidazole;

2-[(4,6-dimethyl-5-methoxy-2-phthalimidylphenyl) methylsulfinyl]-6-chloro-1-ethyl-1H-benzimidazole;

2-[[[2-[[(6-chloro-1-ethyl-1H-benzimidazol-2-yl)sulfinyl]methyl]-3,5-dimethyl-4-methoxyphenyl]amino]carbonyl]benzenecarboxylic acid hydrazide;

2-[[[2-[[(5-chloro-1-ethyl-1H-benzimidazol-2-yl)sulfinyl]methyl]-3,5-dimethyl-4-methoxyphenyl]amino]carbonyl]benzenecarboxylic acid hydrazide;

3-[[(1H-benzimidazol-2-yl)sulfinyl]methyl]benzenamine;

2-[(1H-benzimidazol-2-yl)sulfinylmethyl]benzenamine;

2-[(1H-benzimidazol-2-yl)sulfinylmethyl]N,N-dimethylbenzenamine;

N-[2-[(1H-benzimidazol-2-yl)sulfinylmethyl]phenyl]
acetamide;
2-[[(4-methyl-1H-benzimidazol-2-yl) sulfinyl]methyl]
benzenamine;
2-[[(5,6-dimethyl-1H-benzimidazol-2-yl)sulfinyl]methyl]
benzenamine;
2-[[(5-methoxy-1H-benzimidazol-2-yl)sulfinyl]methyl]
benzenamine;
methyl 2-[[(2-aminophenyl)methyl]sulfinyl]-5-methoxy-
1H-benzimidazole-6-carboxylate;
2-[(1H-benzimidazol-2-yl)sulfinylmethyl]-4-
chlorobenzenamine;
2-[(1H-benzimidazol-2-yl)sulfinylmethyl]-5-
chlorobenzenamine;
2-[(1H-benzimidazol-2-yl)sulfinylmethyl]-4-
methoxybenzenamine;
2-((1H-benzimidazol-2-yl)sulfinylmethyl]-6-
methoxybenzenamine;
2-[(1H-benzimidazol-2-yl)sulfinylmethyl]-3-
methylbenzenamine;
2-[(1H-benzimidazol-2-yl)sulfinylmethyl]-4-
methylbenzenamine;
2-[(1H-benzimidazol-2-yl)sulfinylmethyl]-6-
methylbenzenamine;
2-[(1H-benzimidazol-2-yl)sulfinylmethyl]-4,6-
dimethylbenzenamine;
2-[(1H-benzimidazol-2-yl)sulfinylmethyl]-N-
methylbenzenamine;
2-2-[[(5-methoxy-1H-benzimidazol-2-yl)sulfinyl]methyl]-
4-methylbenzenamine;
2-[[(5-methoxy-1H-benzimidazol-2-yl)sulfinyl]methyl]-6-
methylbenzenamine;
2-[(1H-benzimidazol-2-yl)sulfinylmethyl]-4-
ethylbenzenamine;
2-[(1H-benzimidazol-2-yl)sulfinylmethyl]-6-
ethylbenzenamine;
2-[(1H-benzimidazol-2-yl)sulfinylmethyl]-4-methoxy-3,5-
dimethylbenzenamine;
2-[[(5-methyl-1H-benzimidazol-2-yl)sulfinyl]-methyl]
benzenamine;
2-[[(5-chloro-1H-benzimidazol-2-yl)sulfinyl]-methyl]
benzenamine;
2-([[(5-ethoxy-1H-benzimidazol-2-yl)sulfinyl]-methyl]
benzenamine;
2-[[[(5-(trifluoromethyl)-1H-benzimidazol-2-yl]sulfinyl]
methyl]benzenamine;
2-[(1H-benzimidazol-2-yl)sulfinylmethyl]-4-
(trifluoromethyl)benzenamine;
2-[(1H-benzimidazol-2-yl)sulfinylmethyl]-4-
butylbenzenamine;
2-[(1H-benzimidazol-2-yl)sulfinylmethyl]-5,6-
dimethylbenzenamine;
2-[(1H-benzimidazol-2-yl)sulfinylmethyl]-3,6-
dimethylbenzenamine;
2-[(1H-benzimidazol-2-yl)sulfinylmethyl]-4-chloro-6-
methylbenzenamine;
2-[(1H-benzimidazol-2-ylsulfiny)methyl]-4-chloro-6-
methoxy-3-methylbenzenamine;
2-[[(5-ethoxy-1H-benzimidazol-2-yl)sulfinyl]-methyl]-4-
methylbenzenamine;
2-[[(5-methyl-1H-benzimidazol-2-yl)sulfinyl]-methyl]-5,6-
dimethylbenzenamine;
2-([[(5-(trifluoromethy)1-1H-benzimidazol-2-yl]sulfinyl]-
3,6-dimethylbenzenamine;
2-[[[(5-(trifluoromethy)1-1H-benzimidazol-2-yl]sulfinyl]
methyl]-6-methoxybenzenamine;
methyl 2-amino-3-[(1H-benzimidazol-2-yl)sulfinyl)methyl]
benzoate;
ethyl 4-amino-3-[((1H-benzimidazol-2-yl)sulfinyl)methyl]
benzoate;
ethyl 4-amino-3-[[(5-methoxy-1H-benzimidazol-2-yl)
sulfinyl]methyl]benzoate;
2-[[5,6-dimethoxy-1H-benzimidazol-2-yl)sulfinyl]methyl]-
4-methylbenzenamine;
2-[(1H-benzimidazol-2-yl)sulfinylmethyl]-4-
fluorobenzenamine;
2-[(1H-benzimidazol-2-yl)sulfinylmethyl]-3,4,5-
trimethylbenzenamine;
2-[[(5-methoxy-1H-benzimidazol-2-yl)sulfinyl]methyl]-4-
methoxy-3,5-dimethylbenzenamine;
3-[(1H-benzimidazol-2-yl)sulfinylmethyl]benzenamine;
3-[(1H-benzimidazol-2-yl)sulfinylmethyl]-2-pyridinamine;
3-[(1H-benzimidazol-2-yl)sulfinylmethyl]-N,N-dimethyl-2-
pyridinamine;
6-[(1H-benzimidazol-2-yl)sulfinylmethyl]-2-pyridinamine;
6-[[(4-methyl-1H-benzimidazol-2-yl)-sulfinyl]methyl]-2-
pyridinamine;
6-[[(5-methyl-1H-benzimidazol-2-yl)-sulfinyl]methyl]-2-
pyridinamine;
6-[[(5-methoxy-1H-benzimidazol-2-yl)-sulfinyl]-methyl]-2-
pyridinamine;
6-[[(5-chloro-1H-benzimidazol-2-yl)-sulfinyl]methyl]-2-
pyridinamine;
6-[[[5-(trifluoromethyl)-1H-benzimidazol-2-yl]sulfinyl]
methyl]-2-pyridinamine;
6-[[(5-ethoxy-1H-benzimidazol-2-yl)-sulfinyl]methyl]-2-
pyridinamine;
6-[[(5,6-dimethoxy-1H-benzimidazol-2-yl)-sulfinyl]
methyl]-2-pyridinamine;
6-[[(5,6-dimethyl-1H-benzimidazol-2-yl)-sulfinyl]methyl]-
2-pyridinamine;
6-[[(4,6-dimethyl-1H-benzimidazol-2-yl)-sulfinyl]methyl]-
2-pyridinamine;
6-[[[5-(hydroxymethyl)-1H-benzimidazol-2-yl]sulfinyl]
methyl]-2-pyridinamine;
6-[(1H-benzimidazol-2-yl)sulfinylmethyl]-N-(2,2-
dimethylpropyl)-2-pyridinamine;
6-[(1H-benzimidazol-2-yl)sulfinylmethyl]-N-ethyl-2-
pyridinamine; and
5-[(1H-benzimidazol-2-yl)sulfinylmethyl]-2-pyridinamine.

The invention also involves a method of treating viral infection in a subject with an effective amount of a protease inhibitor. Preferably, the subject is treated with a herpesvirus protease inhibitor. More preferred is a method wherein the viral protease inhibitor is a CMV protease inhibitor or an HSV protease inhibitor. Even more preferred is a method wherein the subject is treated with an inhibitor of CMV protease, encoded by $U_L80$, HSV-1 protease or of HSV-2 protease, encoded by $U_L26$.

The invention further involves a method of treating a subject having a viral infection with an effective amount of a composition containing an $(H^+/K^+)ATPase$ inhibitor and another anti-viral compound. Preferably, the composition contains an $(H^+/K^+)ATPase$ inhibitor and a virus-specific protease inhibitor.

The invention further involves compounds selected from a family of compounds and a pharmaceutically-acceptable salt thereof
2-[(4,6-dimethyl-5-methoxy-2-phthalimidylphenyl)
methylsulfonyl]-5-methoxy-1H-benzimidazole.
2-[[(5-chloro-1H-benzimidazol-2-yl)sulfinyl]methyl]-3 3,5-
dimethyl-4-methoxybenzenamine;
(+)-2-[[(5-methoxy-1H-benzimidazol-2-yl)sulfinyl]
methyl]-3,5-dimethyl-4-methoxybenzenamine;
(−)-2-[[(5-methoxy-1H-benzimidazol-2-yl)sulfinyl]
methyl]-3,5-dimethyl-4-methoxybenzenamine;

N-[2-[[(6-methoxy-1H-benzimidazol-2-yl)sulfinyl]methyl]-3,5-dimethyl-4-methoxyphenyl]acetamide;
2-[(4,6-dimethyl-5-methoxy-2-phthalimidylphenyl) methylsulfinyl]-6-chloro-1-isopropyl-1H-benzimidazole;
2-[(4,6-dimethyl-5-methoxy-2-phthalimidylphenyl) methylsulfinyl]-5-chloro-1-isopropyl-1H-benzimidazole;
2-[[(1-methyl-1H-imidazol-2-yl)sulfinyl]methyl]-3,5-dimethyl-4-methoxybenzenamine;
2-[[(1H-imidazol-2-yl) sulfinyl]methyl]-3,5-dimethyl-4-methoxybenzenamine;
2-[(4,6-dimethyl-5-methoxy-2-phthalimidylphenyl) methylsulfinyl]-5-chloro-1-ethyl-1H-benzimidazole;
2-[(4,6-dimethyl-5-methoxy-2-phthalimidylphenyl) methylsulfinyl]-6-chloro-1-ethyl-1H-benzimidazole;
2-[[[2-[[(6-chloro-1-ethyl-1H-benzimidazol-2-yl)sulfinyl] methyl]-3,5-dimethyl-4-methoxyphenyl]amino]carbonyl] benzenecarboxylic acid hydrazide;
2-[[[2-[[(5-chloro-1-ethyl-1H-benzimidazol-2-yl)sulfinyl] methyl]-3,5-dimethyl-4-methoxyphenyl]amino]carbonyl] benzenecarboxylic acid hydrazide; and
4-methoxy-3,5-dimethyl-2-[(2-pyridinyl)sulfinylmethyl] benzenamine.

The present invention comprises a pharmaceutical composition comprising a therapeutically-effective amount of a compound of the above-identified family in association with at least one pharmaceutically-acceptable carrier, adjuvant or diluent.

Where the term "alkyl" is used, either alone or within other terms such as "haloalkyl", "alkylsulfonyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" denotes linear or branched radicals having two to about twenty carbon atoms or, preferably, two to about twelve carbon atoms. More preferred alkenyl radicals are "lower alkenyl" radicals having two to about ten carbon atoms. Most preferred are lower alkenyl radicals having two to about six carbon atoms. Examples of such radicals include ethylene, n-propylene, isopropylene, n-butylene, isobutylene, pentene, hexene and the like. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide haloalkoxy or haloalkoxyalkyl radicals. The term "cycloalkyloxy" embrace radicals having cycloalkyl portions of three to about ten carbon atoms attached to an oxygen atom. More preferred cycloalkyloxy radicals are "lower cycloalkyloxy" radicals having three to six carbon atoms. Examples of such radicals include cyclopropoxy, cyclobutoxy and cyclohexyloxy. The term "alkenyloxy" embraces linear or branched oxy-containing radicals each having alkenyl portions of two to about ten carbon atoms. More preferred alkenyloxy radicals are "lower alkenyloxy" radicals having two to six carbon atoms. Examples of such radicals include propenoxy and butenoxy. The term "alkynyloxy" embrace linear or branched oxy-containing radicals each having alkynyl portions of two to about ten carbon atoms. More preferred alkynyloxy radicals are "lower alkynyloxy" radicals having two to six carbon atoms. Examples of such radicals include propargyloxy and pentynyloxy. The term "alkylthio" embraces radicals containing a linear or branched alkyl radical, of one to about ten carbon atoms attached to a divalent sulfur atom, such as a methythio radical, (CH$_3$—S—). The term "alkenylthio" embraces radicals containing a linear or branched alkenyl radical, of two to about ten carbon atoms attached to a divalent sulfur atom, such as a propenylthio radical. The term "arylthio" embraces radicals containing a linear or branched aryl radical, of six to about ten carbon atoms attached to a divalent sulfur atom, such as a phenylthio radical. The term "aralkylthio" embraces radicals containing a linear or branched aralkyl radical attached to a divalent sulfur atom, such as a benzylthio radical. The term "cycloalkylthio" embraces radicals containing a linear or branched cycloalkyl radical, of three to about ten carbon atoms attached to a divalent sulfur atom, such as a cyclohexylthio radical. The term "alkylsulfinyl" embraces radicals containing a linear or branched alkyl radical, of one to ten carbon atoms, attached to a divalent —S(=O)— radical. "Arylsulfinyl" embraces aryl radicals attached to a sulfinyl radical, where aryl is defined below. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "aminosulfonyl" or "sulfonamidyl" denotes a sulfonyl radical substituted with an amine radical, forming a sulfonamide (—SO$_2$NH$_2$). The terms "alkylaminosulfonyl" and "dialkylaminosulfonyl" embrace radicals having one or two alkyl radicals, respectively, attached to a aminosulfonyl radical, where alkyl is defined as above. The term "alkylsulfonylamino" describes amino radicals substituted with alkylsulfonyl radical as defined above. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronapthyl, indane and biphenyl. The "aryl" radicals may be further substituted with one or more halo, alkyl, nitro, cyano, haloalkoxy, alkoxy or amine radicals. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, thiazolinyl, dihydropyran, dihydrofuran, dihydroquinolyl, tetrahydroisoquinolyl, thiatetrahydroisoquinolyl, cycloheptenopyridine, benzoxazinyl, dihydrothienopyridinyl, tetrahydroquinolyl and dihydrothiazole. The term "heteroaryl" embraces unsaturated heterocyclic radicals. Examples of unsaturated heterocyclic radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, purinyl, azaimidazopyridyl, benzimidazolyl, quinolyl, isoquinolyl, azaquinolyl, azaisoquinolyl, carbostyryl, imadazopyridyl, azachromanyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, thienopyridinyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. The term "heteroarlkyl" embraces heteroaryl-substituted alkyl radicals such as pyridylmethyl and thienylmethyl. The term "acyl" denotes a radical provided by the residue after removal of hydroxyl from an organic acid. Examples of such acyl radicals include alkanoyl and aroyl radicals. The terms "carboxy" or "carboxyl", whether used alone or with other terms, such as "carboxyalkyl", denotes —CO$_2$H. The term "carbonyl", whether used alone or with other terms, such as "alkoxycarbonyl", denotes a divalent —(C=O)— radical. The term "alkylcarbonyl" means a radical containing an alkyl radical, as defined above, attached to a carbonyl radical. Examples of such "alkylcarbonyl" radicals include substituted or unsubstituted methylcarbonyl, ethylcarbonyl, propylcarbonyl, butylcarbonyl and hexylcarbonyl. The term "alkylcarbonylalkyl" denotes an alkyl radical substituted with an alkylcarbonyl radical as defined above. The term "cycloalkylcarbonyl" means a radical containing an cycloalkyl radical, as defined above, attached to a carbonyl radical. Examples of such "cycloalkylcarbonyl" radicals include substituted or unsubstituted cyclopropylcarbonyl, cyclobutylcarbonyl, cyclopentylcarbonyl and cyclohexylcarbonyl. The term "arylcarbonyl" means a radical containing an aryl radical, as defined above, attached to a carbonyl radical. The term "alkoxycarbonyl" means a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" embraces radicals having "alkoxycarbonyl", as defined above substituted to an alkyl radical. Examples of similar radicals include substituted or unsubstituted "aryloxycarbonyl"[e.g. phenoxycarbonyl, 4-nitrophenoxycarbonyl, 2-naphthyloxycarbonyl, etc.], substituted or unsubstituted "aralkoxycarbonyl", [e.g. benzyloxycarbonyl, phenethyloxycarbonyl, benzhydryloxycarbonyl, 4-nitrobenzyloxycarbonyl, etc.] and the like. The "alkanoyl" radicals may be a substituted or unsubstituted carboxyalkyl radical, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The "aroyl" radicals may be benzoyl, naphthoyl, toluoyl, and the like and the aryl in said aroyl may be additionally substituted. The term "acyloxy" denotes an acyl substituted oxygen atom, such as CH$_3$CO$_2$—. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "cycloalkyl" embraces radicals having three to ten carbon atoms, such as cyclopropyl cyclobutyl, cyclopentyl, cyclohexyl and cycloheptyl. The term "cycloalkenyl" embraces unsaturated radicals having three to ten carbon atoms, such as cyclopropenyl, cyclobutenyl, cyclopentenyl, cyclohexenyl and cycloheptenyl. The term "aryloxy" embraces aryl radicals attached through an oxygen atom to other radicals. More preferred aryloxy radicals are "lower aryloxy" radicals having a phenyl radical. An example of such radicals is phenoxy. The term "aryloxyalkyl" embraces alkyl radicals having one or more aryloxy radicals attached to the alkyl radical, that is, to form monoaryloxyalkyl and diaryloxyalkyl radicals. The "aryloxy" or "aryloxyalkyl" radicals may be further substituted to provide haloaryloxyalkyl radicals, alkylaryloxy radicals, and the like. Examples of such radicals include chlorophenoxy and methylphenoxy. The term "aralkyloxy" embrace oxy-containing aralkyl radicals attached through an oxygen atom to other radicals. The "aralkyloxy" radicals may be further substituted on the aryl ring portion of the radical. The term "aminoalkoxy" embraces alkoxy radicals substituted with one or more amino radicals. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "alkylaminoalkyl" denotes an alkyl radical substituted with an alkylamino radical, as the terms are defined above. The term "alkanoylamino" denotes an amino radical substituted with an alkanoyl radical, as the terms are defined above. The term "arylamino" denotes amino groups which have been substituted with one or two aryl radicals, such as N-phenylamino. The term "aralkylamino" denotes amino groups which have been substituted with one or two aralkyl radicals, such as N-benzylamino, N-phenethylamino and phenpropylamino. The "aralkylamino" or "arylamino"radicals may be further substituted on the aryl ring portion of the radical. The term "N-alkyl-N-arylamino" denote amino radicals substituted with one alkyl and one aryl radical. The terms "amide," and "aminocarbonyl", whether used by themselves or with other terms such as "N-monoalkylaminocarbonyl", "N-monoarylaminocarbonyl", "N,N-dialkylaminocarbonyl", and "N-alkyl-N-arylaminocarbonyl", denote a radical formed by an amino substituted carbonyl, or —C(=O)NH$_2$. The terms "N-alkylaminocarbonyl" and "N,N-dialkylaminocarbonyl", denote amido groups which have been substituted with one alkyl radical and with two alkyl radicals, respectively. The N-alkylaminocarbonyl may be unsubstituted or substituted with halo, such as N-methylaminocarbonyl, N-ethylaminocarbonyl, N-propylaminocarbonyl, N,N-dimethylaminocarbonyl, 2,2,2-trifluoroethylaminocarbonyl or the like. The terms "N-monoarylaminocarbonyl" and "N-alkyl-N-arylaminocarbonyl" denote aminocarbonyl radicals substituted, respectively, with one aryl radical, and one alkyl and one aryl radical. The N-arylaminocarbonyl may be phenylaminocarbonyl, naphthylaminocarbonyl, tolylaminocarbonyl, xylylaminocarbonyl, mesitylaminocarbonyl, cumenylaminocarbonyl, and the like, in which the preferable one is phenylaminocarbonyl. The term "aminocarbonyloxy" denote a radical formed by an oxy substituted aminocarbonyl , or —OC(=O)NH$_2$.

Also included in the family of compounds of Formula I are the stereoisomers and tautomers thereof. Compounds of the present invention can possess one or more asymmetric atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula I are the pharmaceutically-acceptable salts thereof or any other compound which, upon administration to a human subject, is capable of providing (directly or indirectly) the antivirally active metabolite or residue thereof (prodrug). The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

The invention is applicable to viral infections and is preferably for use in subjects infected with a DNA virus. More preferably, the method can be used for subjects infected with a herpesvirus, such as HSV-1, HSV-2, CMV, EBV, VZV, and the like.

GENERAL SYNTHETIC PROCEDURES

The compounds of this invention may be prepared by the methods illustrated in the following Schemes. Unless otherwise specified, the various substituents are defined as for Formula I–III, above.

Scheme I illustrates the preparation of sulfur-containing compounds of Formula I.

SCHEME I

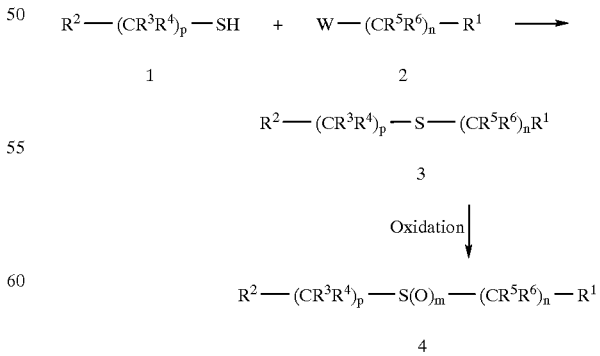

Thio compounds 3 are prepared by at least two routes, each of which uses a mercaptoheterocycle 1. In the preferred route, the mercaptoheterocycle 1 reacts with starting material 2, such as 2-aminobenzylhalide in which W is a halogen, and preferably chlorine or bromine. Typical conditions include reaction at room temperature in an organic solvent, such as absolute ethanol or dimethylformamide (DMF). For those compounds which form hydrohalide salts, the corresponding neutral compounds of 3 are readily obtained by methods known to those skilled in the art. For example, treating such a salt with base (such as aqueous potassium carbonate or preferably sodium hydroxide), followed by extraction into a non-protic organic solvent (such as dichloromethane or chloroform), gives the free base form of 3.

2-Aminobenzyl halides starting material 2, in which W is halogen, are obtained commercially or are prepared from corresponding 2-aminobenzyl alcohols 2, in which W is OH, or 2-methylsulfinylmethylanilines 2, in which W is CH$_3$SO, by synthetic methods well known in the art. For example, reaction of the alcohol with a halogenating reagent, such as thionyl chloride, phosphorus oxychloride, oxalyl chloride, and the like, in an inert organic solvent, such as dichloromethane or chloroform, will give corresponding 2-aminobenzyl chlorides as the hydrochloride salts. A preferred method involves treating the alcohol with hydrochloric or hydrobromic acid at temperatures between about room temperature and about 100° C. See B. Beilenson and F. M. Hamer, *J. Chem. Soc.,* 98–102 (1942).

Where an appropriate 2-aminobenzyl halide 2 is not readily available, thio compounds 3 may also be prepared by an acid-catalyzed reaction of the 2-mercaptoheterocycle 1 with compounds 2. Preferred conditions include heating a mixture of compounds 1 and 2 in glacial acetic acid containing excess (relative to 1 and 2) sulfuric acid. After quenching the reaction by pouring the mixture over ice, the thio compounds 3 are isolated by methods known in the art, including extraction, recrystallization and chromatography. Where an initially required 2-aminobenzyl alcohol 2 is not commercially available, corresponding 2-aminobenzoic acids or 2-aminobenzaldehydes may be reduced using methods known in the art, such as hydrogenation, reaction with lithium aluminum hydride, and the like. Various methods for preparing appropriate aminobenzoic acids are known. See, e.g., Baker et al., *J. Org. Chem.,* 17, 141–148, 149–156 (1952). corresponding 2-nitrobenzyl alcohols or 2-nitrobenzaldehydes may also be reduced using methods known in the art, such as catalytic hydrogenation, to provide the 2-aminobenzyl alcohols.

The sulfoxide compounds 4 of this invention are prepared by oxidation of compounds 3 using methods known to those skilled in the art. Commonly used oxidizing agents include, for example, peracids, such as m-chloroperoxybenzoic acid; magnesium monoperoxyphthalate; peresters; peroxides, such as hydrogen peroxide; sodium metaperiodate; selenium dioxide; manganese dioxide; iodosobenzene; and the like. Preferred conditions for preparing sulfoxides 4 include oxidizing compounds 3 with an approximately equimolar quantity of m-chloroperoxybenzoic acid in an organic solvent, such as dichloromethane, at temperatures between about 0° C. and about room temperature. Oxidization may be terminated by adding dimethylsulfide.

Scheme II illustrates the preparation of sulfur-containing compounds 7 of Formula II.

SCHEME II

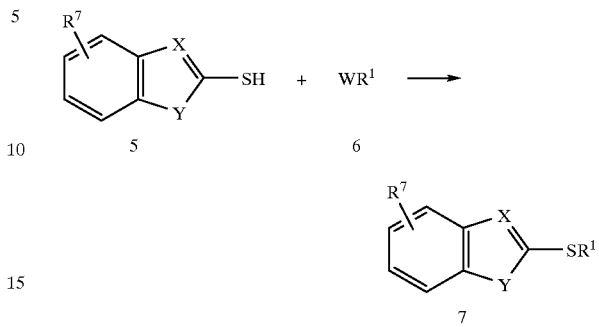

Benzimidazole compounds 7 of Formula II are prepared by at least two routes, similar to that of Scheme I, above, each using a 2-mercaptobenzimidazole 5. In the preferred route, the 2-mercaptobenzimidazole 5 reacts with starting material 6, such as 2-aminobenzyl halide in which W is a halogen, and preferably chlorine or bromine. Typical conditions include reaction at room temperature in an organic solvent such as absolute ethanol or DMF. For those compounds which form hydrohalide salts, the corresponding neutral compounds 7 of Formula II are readily obtained by methods known to those skilled in the art. For example, treating such a salt with base (such as aqueous potassium carbonate or sodium hydroxide), followed by extraction into a non-protic organic solvent (such as dichloromethane or chloroform), gives the free base form of 7.

The 2-aminobenzyl halides of 6, in which W is halogen, are obtained commercially or are prepared from corresponding 2-aminobenzyl alcohols, in which W is OH, or 2-methylsulfinylmethylanilines, in which W is CH$_3$SO, by synthetic methods well known in the art and described above in Scheme I.

Where an appropriate 2-aminobenzyl alcohol starting material 6 is not readily available, compounds of Formula II may also be prepared by an acid-catalyzed reaction of the 2-mercaptobenzimidazole 5 with 2-aminobenzyl alcohols as described above in Scheme I.

Scheme III illustrates the preparation of sulfoxide- and sulfonyl-containing compounds of Formula II.

Scheme III

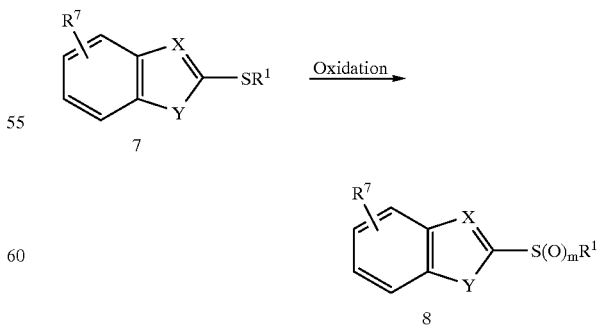

The sulfoxide and sulfonyl containing compounds of this invention are prepared by oxidation of benzimidazoles 7 of Formula II using methods known to those skilled in the art.

Commonly used oxidizing agents include, for example, peracids, such as M-chloroperoxybenzoic acid; peresters; peroxides, such as hydrogen peroxide; sodium metaperiodate; selenium dioxide; manganese dioxide; iodosobenzene; and the like. Preferred conditions for preparing sulfoxides 8 include oxidizing benzimidazoles 7 of Formula II with an approximately equimolar quantity of m-chloroperoxybenzoic acid in an organic solvent, such as dichloromethane, at temperatures between about 0° C. and about room temperature. Oxidization may be terminated by adding dimethylsulfide.

Scheme IV illustrates the preparation of sulfoxide- and sulfonyl-containing compounds of Formula III.

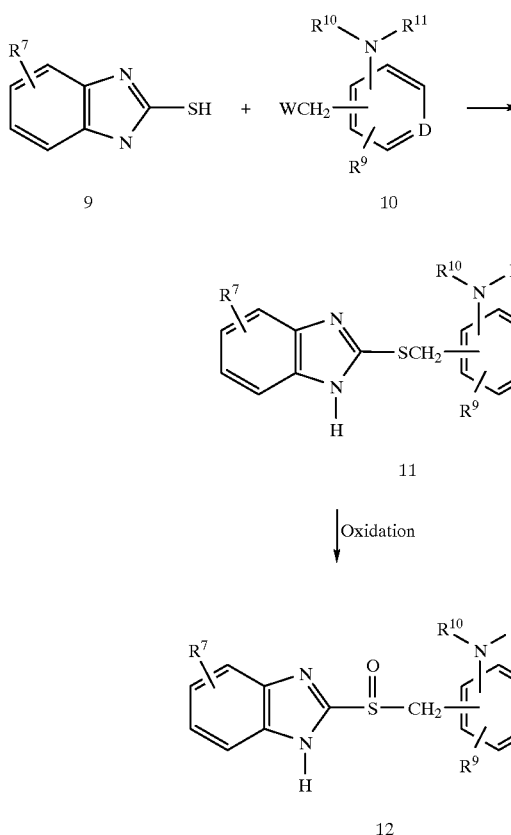

Thio compounds 11 are prepared by a route which uses 2-mercaptobenzimidazole 9. The 2-mercaptobenzimidazole 9 reacts with a 2-aminobenzyl halide or aminopyridyl halide 10 in which W is a halogen, preferably chlorine or bromine. Typical conditions include reaction at room temperature in an organic solvent such as absolute ethanol or isopropyl alcohol. For those compounds which form hydrohalide salts, the corresponding neutral compounds of 11 are readily obtained by methods known to those skilled in the art. For example, treating such a salt with base (such as aqueous potassium carbonate or preferably sodium hydroxide), followed by extraction into a non-protic organic solvent (such as dichloromethane or chloroform), gives the free base form of 11. The sulfoxide-containing 12 and related sulfonyl-containing compounds of this invention are prepared by oxidation of 11 using methods as disclosed above in Scheme III.

Certain of the 2-amino compounds 9 are more conveniently prepared as phthalimide derivatives (that is, where $NR^{10}R^{11}$ is the phthalimide group) and used to prepare corresponding phthalimide derivatives of intermediates 10, as illustrated in the Examples.

Although treatment of such phthalimide derivatives with hydrazine in an alcohol would yield corresponding anilines (that is, intermediates 10 where $R^{10}$ and $R^{11}$ are both hydrogen), the preferred next step is oxidation (as described above) to corresponding phthalimide derivatives of sulfoxides 12. Treatment of the phthalimide derivatives of such sulfoxides with hydrazine hydrate in an alcohol, preferably methanol or ethanol, yields compounds 12 in which $R^{10}$ and $R^{11}$ are both hydrogen. Partial deprotection of the phthalimidyl derivatives yields hydrazidyl derivatives.

Although some of the 2-mercaptobenzimidazoles 9 are commercially available, others may be prepared by synthetic methods known to those skilled in the art. For example, Scheme V illustrates the preparation of 2-mercaptobenzimidazoles from substituted diaminobenzenes of 13.

Scheme V

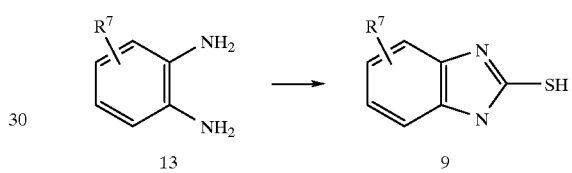

A preferred cyclization method employs an alkali metal alkylxanthate salt of the formula alkyl-O(C=O)S⁻ M+, where M+ represents an alkali metal ion. Such an alkylxanthate salt may be preformed by methods known in the art or may be formed in situ by mixing an alkali metal hydroxide (preferably sodium hydroxide) and carbon disulfide in an alcohol (preferably ethanol). Preferred cyclization conditions include heating an aqueous or alcoholic mixture of a diaminobenzene 13 with sodium or potassium ethylxanthate at reflux under an inert atmosphere, such as argon.

Some of the derivatives of Formula I, to be used according to this invention, are the subject matter of the following patents and publications and can be obtained according to the preparation methods described therein.

The alkoxycarbonylalkylsulfinylthiazolo(5,4-b)pyridines of the Formula I can be prepared with the aid of the methods described in U.S. Pat. No. 5,079,255 which is incorporated by reference.

The alkoxyalkylsulfinylbenzothiazoles of the Formula I can be prepared with the aid of the methods described in EP 370,436 which is incorporated by reference.

The aminoethylthio-(1H)-benzimidazoles of Formula I can be prepared with the aid of the methods described in JP 3,014,566 which is incorporated by reference.

The imidazopyridinylalkylthio-1H-benzimidazoles and imidazopyridinylalkylsulfinyl-1H-benzimidazoles of the Formula I can be prepared with the aid of the methods described in U.S. Pat. Nos. 4,687,775 and 4,721,718 and WO 8,705,021 which are incorporated by reference.

The pyridylalkylthio-1H-benzimidazoles and pyridylalkylsulfinyl-1H-benzimidazoles of the Formula I can be prepared with the aid of the methods described in U.S. Pat. Nos. 5,049,674, 4,772,619, 5,019,584, 5,008,278, 5,045,552, 5,075,323, 5,124,158, 5,250,527, 4,753,955, 4,738,975, 4,727,150, 4,873,337, 4,758,579, 4,619,997, 4,555,518, 4,359,465, 4,255,431, 4,045,563, 4,818,760, WO 9,006,925, WO 9,119,711, WO 9,119,712, WO 8,903,830, WO 8,900,566, DE 4,035,455, DE 3,415,971, EP 481,764, EP 475,456, EP 446,961, EP 298,440, EP 295,603, EP 184,322, EP 178,438, EP 167,943, JP 2,049,774, JP 3,052,887, JP 3,048,680, JP 62,026,275, JP 63,183,577, JP 62,061,978, JP 61,178,919, JP 61,085,383 and JP 5,117,268, which are incorporated by reference.

The benzylthio-1H-benzimidazoles, benzylthio-tetrahydro-1H-benzimidazoles and benzylsulfinyl-1H-benzimidazoles of the Formula I can be prepared with the aid of the methods described in U.S. Pat. No. 5,082,943, WO 8,701,114, EP 526,033, EP 251,536, EP 213,474, GB 2,161,160, GB 2,163,747, JP 63,230,633, JP 63,208,579, JP 62,145,069, JP 62,185,078, JP 62,192,366, JP 62,207,261 and JP 1,230,560, which are incorporated by reference.

The pyrimidinylalkylthio-1H-benzimidazoles, pyrimidinylalkylsulfinyl-1H-benzimidazoles and pyrimidinylalkylsulfonyl-1H-benzimidazoles of Formula I can be prepared with the aid of that described in U.S. Pat. Nos. 4,791,114, 4,777,172, JP 1,132,581, JP 3,038,523, JP 5,262,763 and JP 5,112,559, which are incorporated by reference.

The pyridylalkylthio-dioxolobenzimidazoles and pyridylalkylthio-dioxolobenzimidazoles of the Formula I can be prepared with the aid of the methods described in U.S. Pat. Nos. 4,758,579 and 4,560,693 and WO 8,905,299, which are incorporated by reference.

The benzylsulfinylimidazylpyridines of Formula I can be prepared with the aid of the methods described in U.S. Pat. No. 4,933,458, which are incorporated by reference.

The pyridylalkylsulfinylquinoxalines of Formula I can be prepared with the aid of the methods described in U.S. Pat. No. 4,933,458 and JP 62,161,769, which are incorporated by reference.

The pyridylalkylsulfinylpyridopyrazines of Formula I can be prepared with the aid of the methods described in U.S. Pat. No. 4,933,458 which is incorporated by reference.

The benzimidazolyl-sulfinyl cycloalkylpyridines of Formula I can be prepared with the aid of the methods described in JP 4,364,127 which is incorporated by reference.

The azachromanylalkylsulfinylbenzimidazoles of Formula I can be prepared with the aid of the methods described in U.S. Pat. No. 5,077,407 which is incorporated by reference.

The benzimidazolylsulfinylalkyl-3,4-dihydro-benzoxazines can be prepared with the aid of the methods described in JO 1,022,873 which is incorporated by reference.

The pyrazolylalkylthiobenzimidazoles can be prepared with the aid of the methods described in JP 63,313,784 which is incorporated by reference.

The thienopyridinylalkylsulfinyl benzimidazoles can be prepared with the aid of the methods described in U.S. Pat. No. 4,839,365 and EP 176,308, which are incorporated by reference.

The benzimidazolylthioalkylcarbostyrils can be prepared with the aid of the methods described in JP 62,240,677 which is incorporated by reference.

The isoquinolinylalkylsulfinylbenzimidazoles of Formula I can be prepared with the aid of the methods described in U.S. Pat. No. 4,882,338 which is incorporated by reference.

The imidazolylalkylthiobenzimidazoles can be prepared with the aid of the methods described in JP 63,091,385 which is incorporated by reference.

The benzimidazolylsulfinylalkyl-1,2,3,4-tetrahydroquinolines of Formula I can be prepared with the aid of the methods described in U.S. Pat. Nos. 4,738,970 and 4,963,566 which is incorporated by reference.

The morpholinoalkylsulfinylbenzimidazoles of Formula I can be prepared with the aid of the methods described in U.S. Pat. No. 4,013,776 which is incorporated by reference.

The pyridyl-dihydro-thiazolobenzimidazoles of Formula I can be prepared with the aid of the methods described in U.S. Pat. No. 4,873,237 which is incorporated by reference.

The pyridylalkylthio-naphtho-imidazoles of Formula I can be prepared with the aid of the methods described in U.S. Pat. Nos. 4,182,766 and 4,435,406 which are incorporated by reference.

The pyridylalkylthio-tetrahydro-indeno imidazoles of Formula I can be prepared with the aid of the methods described in U.S. Pat. No. 4,435,406 which is incorporated by reference.

The benzylthio-imidazoquinolines, benzylsulfinyl-imidazoquinolines, pyridylalkylthio-imidazoquinolines and pyridylalkylsulfinyl-imidazoquinolines can be prepared with the aid of the methods described in U.S. Pat. Nos. 4,609,655 and 4,703,044 and JP 3,161,440, which are incorporated by reference.

The pyridylalkylthio-dihydro-indenoimidazol-ones and pyridylalkylsulfinyl-dihydro-indenoimidazol-ones of Formula I can be prepared with the aid of the methods described in U.S. Pat. No. 4,634,710 which is incorporated by reference.

The pyridylalkylthiocycloalkylimidazoles of Formula I can be prepared with the aid of the methods described in U.S. Pat. No. 4,735,955 which is incorporated by reference.

The aralkylalkylthiocycloalkylimidazoles of Formula I can be prepared with the aid of the methods described in JP 1,121,274 and JP 1,121,271 which are incorporated by reference.

The pyridylalkylsulfinylbenzoxazoles of Formula I can be prepared with the aid of the methods described in JP 61,140,582 which is incorporated by reference.

The pyridylalkylthioindoles of Formula I can be prepared with the aid of the methods described in U.S. Pat. No. 4,743,609 which is incorporated by reference.

The pyridylalkylthio-thienoimidazoles and pyridylalkylsulfinyl-thienoimidazoles of Formula I can be prepared with the aid of the methods described in U.S. Pat. Nos. 4,845,118, 5,049,566, WO 8,705,296, JP 1,040,468, EP 304,732 and EP 201,094, which are incorporated by reference.

Pyrimidinylalkylthio-thienoimidazoles of Formula I can be prepared with the aid of the methods described in U.S. Pat. No. 4,956,366 which is incorporated by reference.

Pyridylalkylsulfinylimidazopyridines and pyridylalkylthio-imidazopyridines of Formula I can be prepared with the aid of the methods described in U.S. Pat. Nos. 4,808,596 and 5,049,566, JP 1,190,682, JP 63,146,,883 and JP 62,145,084, which are incorporated by reference.

Pyridylalkylthiobenzothiazoles of Formula I can be prepared with the aid of the methods described in JP 62,207,271 which is incorporated by reference.

Pyridylalkylthioquinolines of Formula I can be prepared with the aid of the methods described in JP 62,209,062 which is incorporated by reference.

Pyrimidinylsulfinyl-quinolines of Formula I can be prepared with the aid of the methods described in U.S. Pat. No. 4,808,591 which is incorporated by reference.

Pyridylalkylsulfinyl-quinazolinones of Formula I can be prepared with the aid of the methods described in U.S. Pat. No. 4,833,144 which is incorporated by reference.

Pyridylalkylthioquinazolines of Formula I can be prepared with the aid of the methods described in JP 63,284,172 which is incorporated by reference.

Pyridylalkylthio-thiadiazoles of Formula I can be prepared with the aid of the methods described in JP 1,233,282 which is incorporated by reference.

Alkenylthio-benzimidazoles of Formula I can be prepared with the aid of the methods described in U.S. Pat. No. 5,106,863 which is incorporated by reference.

Pyridylalkylsulfinyl-pyranobenzimidazoles of Formula I can be prepared with the aid of the methods described in JP 62,145,083 which is incorporated by reference.

Alkoxyalkylsulfinyl-thiazoles of Formula I can be prepared with the aid of the methods described in U.S. Pat. No. 5,171,746 which is incorporated by reference.

Benzylsulfinylimidazoles, pyridylsulfinyl imidazoles, benzylthioimidazoles and pyridylthio imidazoles of Formula I can be prepared with the aid of the methods described in U.S. Pat. Nos. 5,091,403, 3,905,985 and 4,528,298, EP 584588, DT 2,357,277, JP 62,187,469, JP 1,040,467, JP 2,049,727 and JP 3,148,262, which are incorporated by reference.

Pyrimidinylthioalkylimidazoles of Formula I can be prepared with the aid of the methods described in DT 2,403,340 which is incorporated by reference.

Pyridinylthioalkyl-dihydro-1H-imidazoles of Formula I can be prepared with the aid of the methods described in U.S. Pat. No. 4,506,074 which is incorporated by reference.

Pyridylalkylthioheteraryls and pyridylalkylsulfinylheteroaryls of Formula I can be prepared with the aid of the methods described in JP 62,207,270 which is incorporated by reference.

Acid addition salts of this invention may be prepared during the course of the reactions (as described above), by ion exchange from those or other such salts using methods known in the art, or by acidification of free bases of the compounds. Base addition salts of this invention by methods known in the art, including those methods disclosed in British Patent No. 2,137,616 which is incorporated by reference.

The following examples contain detailed descriptions of the methods of preparation of compounds of Formula I–III. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in degrees Centigrade unless otherwise indicated. Omeprazole can be made as described in U.S. Pat. No. 4,255,431 which is incorporated by reference.

EXAMPLE 1

2-[(1H-Benzimidazol-2-yl)thiomethyl]-N,N-dimethylbenzenamine

A mixture of 2.20 g (14.6 mMol) of 2-mercaptobenzimidazole and 3.0 g (14.6 mMol) of 2-(chloromethyl)-N,N-dimethylaniline in 120 ml of absolute ethanol were stirred under nitrogen for about two hours. A solid (4.8 g) was collected by filtration, washed with ethanol, and air-dried. The solid was dissolved in water and made basic with potassium carbonate, then extracted into dichloromethane. The organic phase was dried over sodium sulfate, filtered, and concentrated in vacuo to dryness. Recrystallization from acetonitrile gave 2.3 g of a white solid (first crop). Concentration of the acetonitrile liquors gave 0.7 g of a second crop. The two crops were combined and recrystallized from isopropyl alcohol, giving the title compound as an analytically pure solid, m.p. 167–170° C. Anal. Calc'd. for $C_{16}H_{17}N_3S$: C, 67.81; H, 6.05; N, 14.83; S, 11.31. Found: C, 67.84; H, 6.19; N, 14.73; S, 11.50.

EXAMPLE 2

2-[(1H-Benzimidazol-2-yl)thiomethyl]benzenamine

A mixture of 9.0 g (60 mMol) of 2-mercaptobenzimidazole and 4.9 g (40 mMol) of 2-aminobenzyl alcohol were heated at 84° C. in a mixture of 45 ml of glacial acetic acid and 12.0 g (120 mMol) of sulfuric acid. After two hours an additional 1 g (8 mMol) of 2-aminobenzyl alcohol and 1 g of sulfuric acid were added. After one hour the reaction mixture was cooled and poured into cold benzenamine hemihydrate.

EXAMPLE 3

2-[(1H-Benzimidazol-2-yl)sulfinylmethyl]benzenamine

The title product of Example 2 (830 mg, 3.25 mMol) was dissolved in about 200 ml of boiling chloroform and then cooled to about −10° C. A solution of 662 mg (ca. 3.25 mmol) of ca. 85% m-chloroperoxybenzoic acid in 10 ml of chloroform was then added with stirring over about ten minutes. After another thirty minutes, the reaction was quenched with 4 drops of dimethylsulfide and a white solid was collected by filtration. The solid was washed sequentially with chloroform and diethyl ether, then air dried, giving 550 mg of the title compound: m.p. 164–165° C. Anal. Calc'd. for $C_{14}H_{13}N_3OS*½ H2O$: C,59.98; H,5.03; N, 15.00; S, 11.44. Found: C, 60.11; H, 4.82; N, 14.93; S, 11.44.

3(a) Proceeding in a like manner but replacing 2-aminobenzyl alcohol with 3-aminobenzyl alcohol, 3-[(1H-benzimidazol-2-yl)sulfinylmethyl]benzenamine was prepared.

EXAMPLE 4

2-[(1H-Benzimidazol-2-yl)sulfinylmethyl]N,N-dimethylbenzenamine

The title compound was prepared by the method of Example 3 using 1.5 g of the title product of Example 1 instead of the title product of Example 2. Recrystallization from diethyl ether gave 786 mg of the title compound: m.p. 107–109° C. Anal. Calc'd. for $C_{16}H_{17}N_3OS$: C, 64.19; H, 5.72; N,14.04; S, 10.71. Found: C, 64.44; H, 5.83; N, 14.12; S, 11.06.

EXAMPLE 5

N-[2-[(1H-Benzimidazol-2-yl)thiomethyl]phenyl]acetamide

A solution of 10 g (81.3 mMol) of 2-aminobenzyl alcohol and 50 ml (ca. 530 mMol) of acetic anhydride was allowed to stand in 200 ml of pyridine for 20 hours. The solution was concentrated in vacuo and the resultant solid was washed with diethyl ether. The resultant diacetyl intermediate was collected as white needles. A mixture of 7.30 g (35.3 mMol) of the intermediate and 7.30 g (52.9 mMol) of potassium carbonate was stirred for 30 minutes in 300 ml of methanol. After removing insolubles by filtration, the filtrate was concentrated to give the N-acetyl intermediate. The material was suspended in 1 liter of dichloromethane to which was added 10 ml (ca. 137 mMol) of thionyl chloride. After 19 hours the reaction mixture was concentrated to dryness. Chloroform was added to the residue and then removed in vacuo to give crude N-(2-chloromethylphenyl)acetamide, which was used in the subsequent reaction without further purification. Using the method described in Example 1 with N-(2-chloromethylphenyl) acetamide instead of 2-(chloromethyl)-N,N-dimethylaniline produced 3.9 g of the title compound: m.p. 218–222° C. Anal. Calc'd. for $C_{16}H_{15}N_3OS$: C, 64.62; H, 5.08; N,14.13; S, 10.78. Found: C, 64.20; H, 5.20; N, 14.02; S, 11.06.

EXAMPLE 6

N-[2-[(1H-Benzimidazol-2-yl)sulfinylmethyl] phenyl]acetamide

The title compound was prepared by the method of Example 3 using 1.80 g of the title product of Example 5 instead of the title product of Example 2. Trituration with diethylether gave 1.52 g of the title compound: m.p. 201–202.5° C. Anal. Calc'd. for $C_{16}H_{15}N_3O_2S$: C, 61.32; H, 4.82; N,13.41; S, 10.23. Found: C, 61.00; H, 4.90; N, 13.28; S, 10.50.

EXAMPLE 7

2-[[(4-Methyl-1H-benzimidazol-2-yl)thio]methyl] benzenamine

The title compound was prepared by the method of Example 1 using 3.52 g of 2-mercapto-4-methylbenzimidazole instead of 2-mercaptobenzimidazole and 3.52 g of 2-(chloromethyl) aniline hydrochloride instead of 2-(chloromethyl)-N,N-dimethylaniline. Recrystallization from diethyl ether gave 1.23 g of the title compound: m.p. 125–127° C. Anal. Calc'd. for $C_{15}H_{15}N_3S$: C, 66.89; H, 5.61; N,15.60; S, 11.90. Found: C, 66.76; H, 5.62; N, 15.41; S, 11.87.

EXAMPLE 8

2-[[(4-Methyl-1H-benzimidazol-2-yl)sulfinyl] methyl]benzenamine hemihydrate

The title compound (740 mg) was prepared by the method of Example 3 using 900 mg of the title product of Example 7 instead of the title product of Example 2. Anal. Calc'd. for $C_{15}H_{15}N_3S*½ H_2O$: C, 61.20; H,5.48; N, 14.27; S, 10.89. Found: C, 61.21; H, 5.05; N, 13.88; S, 11.12.

EXAMPLE 9

2-[[(5,6-Dimethyl-1H-benzimidazol-2-yl)thio] methyl]benzenamine

The title compound was prepared by the method of Example 1 using 2.56 g of 5,6-dimethyl-2-mercaptobenzimi- dazole instead of 2-mercaptobenzimidazole and 2.56 g of 2-(chloromethyl) aniline hydrochloride instead of 2-(chloromethyl)-N,N-dimethylaniline. Instead of using sodium carbonate in an extraction, the crude precipitate was neutralized with triethylamine in methanol. Trituration of the resultant crude title compound with methanol and diethyl ether gave 2.0 g of analytically pure title compound. Anal. Calc'd. for $C_{15}H_{15}N_3S$: C, 67.81; H, 6.05; N,14.83; S, 11.31. Found: C, 67.21; H, 6.16; N, 14.50; S, 11.06.

EXAMPLE 10

2-[[(5,6-Dimethyl-1H-benzimidazol-2-yl)sulfinyl] methyl]benzenamine ¼ hydrate

The title compound, m.p. 179–181° C., was prepared by the method of Example 3 using 1.52 g of the title product of Example 9 instead of the title product of Example 2. Anal. Calc'd. for $C_{16}H_{17}N_3OS*¼H_2O$: C, 63.24; H,5.80; N, 13.83; S, 10.55. Found: C, 62.80; H, 5.49; N, 13.53; S, 10.76.

EXAMPLE 11

2-[[(5-methoxy-1H-benzimidazol-2-yl)thio]methyl] benzenamine

The title compound was prepared by the method of Example 1 using 1.68 g (9.33 mMol) of 2-mercapto-5-methoxybenzimidazole instead of 2-mercaptobenzimidazole and 1.99 g (11.2 mMol) of 2-(chloromethyl)aniline hydrochloride instead of 2-(chloromethyl)-N,N-dimethylaniline in 250 ml of isopropyl alcohol. The basic extraction used 5% sodium hydroxide instead of sodium carbonate. Chromatography on silica gel, followed by crystallization from diethylether, gave 520 mg of pure title compound: m.p. 140–142° C. Anal. Calc'd. for $C_{15}H_{15}N_3OS$: C, 63.14; H, 5.30; N,14.73; S, 11.23. Found: C, 63.44; H, 5.42; N, 14.43; S, 11.07.

EXAMPLE 12

2-[[(5-Methoxy-1H-benzimidazol-2-yl)sulfinyl] methyl]benzenamine

The title compound was prepared by the method of Example 3 using 1.20 g of the title product of Example 11 instead of the title product of Example 2. Trituration with diethylether gave 1.04 g of the title compound: m.p. 147–148° C. Anal. Calc'd. for $C_{15}H_{15}N_3O_2S$: C, 59.78; H, 5.02; N,13.94; S, 10.64. Found: C, 59.30; H, 4.95; N, 13.55; S, 10.73.

EXAMPLE 13

Methyl 2-[[(2-aminophenyl)methyl]thio]-5-methoxy-1H-benzimidazole-6-carboxylate, dihydrochloride To a mixture of 29.0 g (0.16 mole) of methyl-4-amino-2-methoxybenzoate, 0.5 g of 4-dimethylaminopyridine, and 16.0 gm (0.16 mole) of triethylamine in 500 ml of dichloromethane was added in batches 22 ml (ca. 0.23 mole) of acetic acid. After two hours the reaction mixture was neutralized with sodium bicarbonate (in solution and as a solid). The organic phase was washed successively with aqueous sodium bicarbonate. The organic phase was washed successively with aqueous sodium bicarbonate and brine, dried over magnesium sulfate, filtered, and concentrated in vacuo. Recrystallization from toluene gave 30 g of methyl-4-acetamido-2-methoxybenzoate. To 100 ml of fuming nitric acid, stirred at –40° C., was slowly added 22.3 g (0.10 mole) of the acetylated intermediate. After about twenty minutes the mixture was warmed to 0° C. and stirred for another twenty minutes. The mixture was poured onto one liter of ice and the resultant precipitate was collected. Recrystallization from toluene/ethanol gave 14.2 g of the nitrated and deacetylated compound, methyl-4-amino-2-methoxy-5-nitrobenzoate. (Under similar conditions in which the acetyl group is not removed, saponification with methanolic sodium hydroxide gives the same product.) Hydrogenation of the nitro intermediate in tetrahydrofuran using Raney nickel as catalyst gave methyl-4,5-diamino-2-methoxybenzoate. A mixture of 4.83 g (24.6 mMol) of the diamine and 7.08 g (49.2 mMol) of potassium ethylxanthate was heated at reflux under argon in 40 ml of water. The resultant product mixture was chromatographed on silica gel to give 1.5 g of methyl-2-mercapto-5-methoxy-1H-benzimidazole-6-carboxylate. (Analysis. Calc'd. for $C_{10}H_{10}N_2O_3S$: C, 50.41; H, 4.23; N, 11.76; S, 13.46. Found: C, 50.30; H, 4.19; N, 11.71; S, 13.12.) The title compound was then prepared by the method of Example 1 using 1.19 g (5.0 mMol) of methyl-2-mercapto-5-methoxy-1H-benzimidazole-6-carboxylate instead of 2-mercaptobenzimidazole and 0.97 g (5.5 mMol)of 2-(chloromethyl)aniline hydrochloride instead of 2-(chloromethyl)-N,N-dimethylaniline. Anal. Calc'd. for $C_{17}H_{17}N_3O_3S*2HCl$: C, 49.05; H,4.60; N, 10.09; S, 7.70; Cl, 17.03. Found: C, 49.37; H, 4.77; N, 9.72; S, 7.43; Cl, 16.77.

EXAMPLE 14

Methyl 2-[[(2-aminophenyl)methyl]sulfinyl]-5-methoxy-1H-benzimidazole-6-carboxylate The title compound is prepared by the method of Example 3 using the title product of Example 11 instead of the title product of Example 2.

EXAMPLE 15

2-[(1H-Benzimidazol-2-yl)thiomethyl]-4-chlorobenzenamine

The title compound was prepared by the method of Example 1 using 6.0 g of 2-(bromomethyl)-4-chloroaniline hydrobromide instead of 2-(chloromethyl)-N,N-dimethylaniline and isopropyl alcohol instead of ethanol. Concentration to dryness, chromatography on silica gel, and crystallization from methanol to which was added water, gave 343 mg of the title compound: m.p. 114–118° C. Anal. Calc'd. for $C_{14}H_{12}N_3ClS$: C, 58.02; H, 4.17; N, 14.50; Cl, 12.23; S, 11.06. Found: C, 58.16; H, 4.24; N, 14.44; Cl, 12.35; S, 11.35.

EXAMPLE 16

2-[(1H-Benzimidazol-2-yl) sulfinylmethyl]-4-chlorobenzenamine

The title compound was prepared by the method of Example 3 using 1.36 g of the title product of Example 15 instead of the title product of Example 2 and dichloromethane instead of chloroform. After the initial trituration, purification was effected using chromatography on silica gel. Trituration with methanol/dichloromethane gave 316 mg of the title compound: m.p. 210–211° C. Anal. Calc'd. for $C_{14}H_{13}N_3OClS$: C, 54.99; H, 3.96; N, 13.74; Cl, 11.59; S, 10.48. Found: C, 54.87; H, 3.91; N, 13.55; Cl, 12.26; S, 10.61.

EXAMPLE 17

2-[(1H-Benzimidazol-2-yl)thiomethyl]-5-chlorobenzenamine

The title compound was prepared by the method of Example 1 using 5.40 g of 2-(bromomethyl)-5-chloroaniline hydrobromide instead of 2-(chloromethyl)-N,N-dimethylaniline in 100 ml of isopropyl alcohol. Chromatography on silica gel and recrystallization from acetonitrile gave 160 mg of the title compound: m.p. 158–160.5° C. Anal. Calc'd. for $C_{14}H_{12}N_3ClS$: C, 58.03; H, 4.17; N, 12.23; S, 11.06. Found: C, 57.95; H, 4.22; N, 14.41; Cl, 12.54; S, 10.96.

EXAMPLE 18

2-[(1H-Benzimidazol-2-yl) sulfinylmethyl]-5-chlorobenzenamine

The title compound was prepared by the method of Example 3 using 1.13 g of the title product of Example 17 instead of the title product of Example 2. Trituration with chloroform gave 1.04 g of the title compound: m.p. 173.5–175.5° C. Anal. Calc'd. for $C_{14}H_{12}N_3ClOS$: C, 54.99; H, 3.96; N, 13.74; Cl, 11.59; S, 10.48. Found: C, 54.37; H, 3.99; N, 13.43; Cl, 11.52; S, 10.21.

EXAMPLE 19

2-[(1H-Benzimidazol-2-yl)thiomethyl]-4-methoxybenzenamine dihydrochloride

The title compound was prepared by the method of Example 1 using 2.85 g of 2-(chloromethyl)-4-methoxyaniline hydrochloride instead of 2-(chloromethyl)-N,N-dimethylaniline. The precipitate was not neutralized with base but was instead washed sequentially with ethanol and diethyl ether, giving 2.56 g of the title compound as the dihydrochloride, m.p. 206–208° C. Anal. Calc'd. for $C_{15}H_{15}N_3OS*2HCl$: C, 50.29; H,4.78; N, 11.73; S, 8.95; Cl, 19.79. Found: C, 49.95; H, 4.57; N, 11.55; S, 9.07; Cl, 19.09.

EXAMPLE 20

2-[(1H-Benzimidazol-2-yl)sulfinylmethyl]-4-methoxybenzenamine

The title compound was prepared by the method of Example 3 using 2.20 g of the free base of the title product of Example 19 instead of the title product of Example 2. Trituration with diethyl ether gave 900 mg of the title compound: m.p. 152–153° C. Anal. Calc'd. for $C_{15}H_5N_3O_2S$: C, 59.78; H, 5.02; N, 13.94; S, 10.64. Found: C, 59.01; H, 4.97; N, 13.65; S, 10.65.

EXAMPLE 21

2-[(1H-Benzimidazol-2-yl)thiomethyl]-6-methoxybenzenamine hemihydrate

The title compound was prepared by the method of Example 1 using 4.16 g of 2-(chloromethyl)-6-methoxyaniline hydrochloride instead of 2-(chloromethyl)-N,N-dimethylaniline. Trituration with diethyl ether gave 2.40 g of the title compound. Anal. Calc'd. for $C_{15}H_{15}N_3OS*½ H_2O$: C, 61.20; H, 5.48; N, 14.27; S, 10.89. Found: C, 61.79; H, 5.10; N, 14.72; S, 11.10.

EXAMPLE 22

2-[(1H-Benzimidazol-2-yl)sulfinylmethyl]-6-methoxybenzenamine hemihydrate

The title compound was prepared by the method of Example 3 using 1.50 g of the title product of Example 21 instead of the title product of Example 2. The reaction mixture was concentrated in vacuo and triturated with diethyl ether. After filtration, the filtrate deposited 202 mg of the title compound: m.p. 141–143.0° C. Anal. Calc'd. for $C_{15}H_{15}N_3O_2S*½H_2O$: C, 58.05; H, 5.20; N, 13.54; S, 10.33. Found: C, 57.65; H, 5.17; N, 13.19; S, 10.50.

EXAMPLE 23

2-[(1H-Benzimidazol-2-yl)thiomethyl]-3-methylbenzenamine

The title compound was prepared by the method of Example 1 using 3.55 g of 2-(chloromethyl)-3-methylaniline hydrochloride instead of 2-(chloromethyl)-N,N-dimethylaniline. Trituration with diethyl ether gave 2.31 g of the title compound. Anal. Calc'd. for $C_{15}H_{15}N_3S$: C, 66.89; H, 5.61; N, 15.60; S, 11.90. Found: C, 66.61; H, 5.53; N, 15.52; S, 11.80.

EXAMPLE 24

2-[(1H-Benzimidazol-2-yl)sulfinylmethyl]-3-methylbenzenamine ¼ hydrate

The title compound was prepared by the method of Example 3 using 1.07 g of the title product of Example 23 instead of the title product of Example 2. Trituration with dichloromethane gave 327 mg of the title compound: m.p. 152–153.0° C. Anal. Calc'd. for $C_{15}H_{15}N_3OS*¼H_2O$: C, 62.21; H, 5.31; N, 14.51; S, 11.07. Found: C, 62.28; H, 5.05; N, 14.46; S, 11.22.

EXAMPLE 25

2-[(1H-Benzimidazol-2-yl)thiomethyl]-4-methylbenzenamine

The title compound was prepared by the method of Example 1 using 2-(chloromethyl)-4-methylaniline hydrochloride instead of 2-(chloromethyl)-N,N-dimethylaniline. Chromatography on silica gel gave 650 mg of the title compound. Anal. Calc'd. for $C_{15}H_{15}N_3S$: C, 66.89; H, 5.61; N, 15.60; S, 11.90. Found: C, 66.70; H, 5.65; N, 15.50; S, 11.85.

EXAMPLE 26

2-[(1H-Benzimidazol-2-yl)sulfinylmethyl]-4-methylbenzenamine

The title compound was prepared by the method of Example 3 using 2.68 g of the title product of Example 25 instead of the title product of Example 2 and using 1,2-dichloroethane as solvent instead of chloroform. Trituration with diethyl ether gave 3.0 g of the title compound. Anal. Calc'd. for $C_{15}H_{15}N_3OS$: C, 63.14; H, 5.30; N, 14.73; S, 11.23. Found: C, 61.44; H, 4.98; N, 14.35; S, 11.10.

EXAMPLE 27

2-[(1H-Benzimidazol-2-yl)thiomethyl]-6-methylbenzenamine

The title compound was prepared by the method of Example 1 using 5.00 g of 2-(chloromethyl)-6-methylaniline hydrochloride instead of 2-(chloromethyl)-N,N-dimethylaniline. Trituration with hexane gave 3.33 g of the title compound: m.p. 130–134.0° C. Anal. Calc'd. for $C_{15}H_{15}N_3S$: C, 66.89; H, 5.61; N, 15.60; S, 11.90. Found: C, 66.85; H, 5.61; N, 15.20; S, 11.50.

EXAMPLE 28

2-[(1H-Benzimidazol-2-yl)sulfinylmethyl]-6-methylbenzenamine

The title compound was prepared by the method of Example 3 using 1.68 g of the title product of Example 27 instead of the title product of Example 2. Trituration with acetonitrile gave 948 mg of the title compound: m.p. 156–157.0° C. Anal. Calc'd. for $C_{15}H_{15}N_3OS$: C, 63.14; H, 5.30; N, 14.73; S, 11.23. Found: C, 62.91; H, 5.18; N, 14.33; S, 11.08.

EXAMPLE 29

2-[(1H-Benzimidazol-2-yl)thiomethyl]-4,6-dimethylbenzenamine

The title compound was prepared by the method of Example 1 using 1.68 g of 2-(chloromethyl)-4,6-dimethylaniline hydrochloride instead of 2-(chloromethyl)-N,N-dimethylaniline. Crystallization from diethyl ether gave 788 mg of the title compound: m.p. 139–141° C. Anal. Calc'd. for $C_{16}H_{17}N_3S$: C, 67.81; H, 6.05; N, 14.83; S, 11.31. Found: C, 67.30; H, 5.93; N, 14.66; S, 11.29.

EXAMPLE 30

2-[(1H-Benzimidazol-2-yl)sulfinylmethyl]-4,6-dimethylbenzenamine hemihydrate

The title compound was prepared by the method of Example 3 using 950 mg of the title product of Example 29 instead of the title product of Example 2. Trituration with diethylether gave 434 mg of the title compound. Anal. Calc'd. for $C_{16}H_{17}N_3OS*½H_2O$: C, 62.23; H, 5.88; N, 13.63; S, 10.40. Found: C, 62.39; H, 5.72; N, 13.50; S, 10.65.

EXAMPLE 31

2-[(1H-Benzimidazol-2-yl)thiomethyl]-N-methylbenzenamine

The title compound was prepared by the method of Example 1 using 28.8 g of 2-(chloromethyl)-N-methylaniline hydrochloride instead of 2-(chloromethyl)-N,N-dimethylaniline. Trituration with diethyl ether gave 22.5 g of the title compound: m.p. 109–112° C. Anal. Calc'd. for $C_{15}H_{15}N_3S$: C, 66.89; H, 5.61; N, 15.60; S, 11.90. Found: C, 66.76; H, 5.72; N, 15.47; S, 11.98.

EXAMPLE 32

2-[(1H-Benzimidazol-2-yl)sulfinylmethyl]-N-methylbenzenamine monohydrate

The title compound was prepared by the method of Example 3 using 10.0 g of the title product of Example 31 instead of the title product of Example 2. Trituration with diethylether, filtration, and concentration of the filtrate gave 4.33 g of the title compound: m.p. 117–120° C. Anal. Calc'd. for $C_{15}H_{15}N_3OS*H_2O$: C, 59.39; H, 5.65; N, 13.85; S, 10.57. Found: C, 59.10; H, 5.57; N, 13.92; S, 10.47.

EXAMPLE 33

2-[[(5-Methoxy-1H-benzimidazol-2-yl)thio]methyl]-4-methylbenzenamine

The title compound (1.95 g) was prepared by the method of Example 1 using 2.81 g of 2-mercapto-5- methoxybenzimidazole instead of 2-mercaptobenzimidazole and 3.00 g of 2-(chloromethyl)-4-methylaniline hydrochloride instead of 2-(chloromethyl)-N,N-dimethylaniline. Anal. Calc'd. for $C_{16}H_{17}N_3OS$: C, 64.19; H, 5.72; N, 14.04; S, 10.71. Found: C, 63.71; H, 5.80; N, 13.86; S, 10.60.

EXAMPLE 34

2-[[(5-Methoxy-1H-benzimidazol-2-yl)sulfinyl]methyl]-4-methylbenzenamine

The title compound was prepared by the method of Example 3 using 1.50 g of the title product of Example 33 instead of the title product of Example 2. Concentration to dryness and trituration with diethyl ether gave 1.10 g of the title compound: m.p. 148–149° C. Anal. Calc'd. for $C_{16}H_{17}N_3O_2S$: C, 60.93; H, 5.43; N, 13.32; S, 10.17. Found: C, 60.67; H, 5.38; N. 13.20; S, 9.95.

EXAMPLE 35

2-[[(5-Methoxy-1H-benzimidazol-2-yl)thio]methyl]-6-methylbenzenamine

The title compound was prepared by the method of Example 1 using 3.75 g of 2-mercapto-5-methoxybenzimidazole instead of 2-mercaptobenzimidazole and 4.00 g of 2-(chloromethyl)-6-methylaniline hydrochloride instead of 2-(chloromethyl)-N,N-dimethylaniline. Trituration with hexane gave 3.02 g of the title compound: m.p. 132–134° C. Anal. Calc'd. for $C_{16}H_{17}N_3OS$: C, 64.19; H, 5.72; N, 14.04; S, 10.71. Found: C, 64.21; H, 5.77; N, 14.00; S, 10.38.

EXAMPLE 36

2-[[(5-Methoxy-1H-benzimidazol-2-yl) sulfinyl]methyll-6-methylbenzenamine

The title compound was prepared by the method of Example 3 using 2.00 g of the title product of Example 35 instead of the title product of Example 2. Trituration with diethylether gave 1.58 g of the title compound: m.p. 142–144° C. Anal. Calc'd. for $C_{16}H_{17}N_3O_2S$: C, 60.93; H, 5.43; N, 13.32; S, 10.17. Found: C, 60.60; H, 5.42; N, 12.83; S, 9.86.

EXAMPLE 37

2-[(1H-Benzimidazol-2-yl)sulfinylmethyl]-4-ethylbenzenamine

The title compound, m.p. 155–156° C., was prepared by the methods of Examples 1 and 3 using 2-(chloromethyl)-4-ethylaniline hydrochloride instead of 2-(chloromethyl)-N,N-dimethylaniline. Anal. Calc'd. for $C_{16}H_{17}N_3OS$: C, 64.19; H, 5.72; N, 14.04; S, 10.71. Found: C, 63.86; H, 5.67; N, 14.01; S, 10.68.

EXAMPLE 38

2-[(1H-Benzimidazol-2-yl)sulfinylmethyl]-6-ethylbenzenamine

The title compound was prepared by the methods of Examples 1 and 3 using 2-(chloromethyl)-6-ethylaniline hydrochloride instead of 2-(chloromethyl)-N,N-dimethylaniline. Anal. Calc'd. for $C_{16}H_{17}N_3OS$: C, 64.19; H, 5.73; N, 14.04; S, 10.71. Found: C, 63.88; H, 5.55; N, 13.87, S, 10.57.

EXAMPLE 39

2-[(1H-Benzimidazol-2-yl)sulfinylmethyl]-4-methoxy-3,5-dimethylbenzenamine

A mixture of 10 g (66.2 mmol) of 4-methoxy-3,5-dimethylaniline and 10 g (67.6 mMol) of phthalic anhydride was heated at 170° C. for 30 minutes, then allowed to cool overnight to room temperature. Recrystallization from aqueous ethanol gave 16.4 g (58.4 mMol) of the phthalimide derivative. Paraformaldehyde (3 g, 100 mMol) was dissolved in 100 ml of concentrated sulfuric acid and the mixture was cooled to 0° C. Hydrogen chloride gas was introduced over a five-minute period, after which the phthalimide derivative was added in small batches. After additional hydrogen chloride gas was introduced for five minutes, the mixture was stirred at 0° C. for 45 minutes. The mixture was poured over ice, filtered, and washed with water, giving 5.34 g of the phthalimide derivative (m.p. 267–271° C.) of 2-hydroxymethyl-4-methoxy-3,5-dimethylaniline. Using the general method of Example 2 with this phthalimide derivative instead of 2-aminobenzyl alcohol and concentrated hydrochloric acid instead of sulfuric acid produced the phthalimide derivative of 2-[(1H-benzimidazol-2-yl)thiomethyl]-4-methoxy-3,5-dimethylbenzenamine. Trituration with diethyl ether gave 3.4 g of the analytically pure compound, m.p. 240–244° C. [Anal. Calc'd. for $C_{25}H_{21}N_3O_3S$: C, 67.70; H, 4.77; N, 9.47; S, 7.23. Found: C, 67.57; H, 4.84; N, 9.53; S, 7.31.] Using the method of Example 3 with 3.0 g (6.8 mMol) of this phthalimide derivative instead of the title product of Example 2 produced the corresponding sulfoxide. Trituration with diethyl ether gave 2.81 g of the analytically pure sulfoxide as the ¼ hydrate: m.p. 198.5–201° C. [Anal. Calc'd. for $C_{25}H_{21}N_3O_4S*¼ H_2O$: C, 64.71; H, 4.67; N, 9.06; S, 6.91. Found: C, 64.82; H, 4.63; N, 9.07;S, 6.96.] The sulfoxide (1.0 g, 2.2 mmol) was dissolved in 50 ml of methanol by warming to 50–60° C. and then allowed to cool to room temperature. Hydrazine hydrate (1 ml, ca. 20 mMol) was added and the mixture was stirred for about 5 hours. The resultant suspension was concentrated in vacuo, suspended in water, and treated with about 50 drops of aqueous ammonium hydroxide. The precipitate was collected and washed with dilute ammonium hydroxide to give 0.47 g of the title compound: m.p. 150–155° C. Anal. Calc'd. for $C_{17}H_{19}N_3O_2S$: C, 61.98; H, 5.81; N, 12.76; S, 9.73. Found: C, 61.66; H, 5.85; N, 12.61; S, 9.34.

EXAMPLE 40

2-[[(S-Methyl-1H-benzimidazol-2-yl)thio]methyl]benzenamine

The title compound was prepared by the method of Example 1 using 2.50 g of 2-mercapto-5-methylbenzimidazole instead of 2-mercaptobenzimidazole and 2.71 g of 2-(chloromethyl)aniline hydrochloride instead of 2-(chloromethyl)-N,N-dimethylaniline in isopropyl alcohol. The basic extraction used 5% sodium hydroxide instead of sodium carbonate. Washing the solid residue from the dichloromethane extract with additional dichloromethane gave 1.65 g of the title compound. Anal. Calc'd. for $C_{15}H_{15}N_3S$: C, 66.89; H, 5.61; N, 15.60; S, 11.90. Found: C, 65.78; H, 5.48; N, 15.54; S, 11.94.

EXAMPLE 41

2-[[(S-Methyl-1H-benzimidazol-2-yl)sulfinyl]methyl]benzenamine

The title compound was prepared by the method of Example 3 using 1.46 g of the title product of Example 40 instead of the title product of Example 2. Trituration with 2.5% aqueous potassium carbonate and with water gave 1.02 g of the title compound: m.p. 170–171° C. Anal. Calc'd. for $C_{15}H_{15}N_3OS$: C, 63.14; H, 5.30; N, 14.73; S, 11.23. Found: C, 62.76, H, 5.30; N, 14.86; S, 11.25.

EXAMPLE 42

2-[[(5-Chloro-1H-benzimidazol-2-yl)thio]-methyl]benzenamine

The title compound was prepared by the method of Example 1 using 2.50 g of 2-mercapto-5-chlorobenzimidazole instead of 2-mercaptobenzimidazole and 2.42 g of 2-(chloromethyl)aniline hydrochloride instead of 2-(chloromethyl)-N,N-dimethylaniline. The basic extraction used 5% sodium hydroxide instead of sodium carbonate. Washing the solid residue from the dichloromethane extract with additional dichloromethane gave 2.47 g of the title compound. Anal. Calc'd. for $C_{14}H_{12}N_3ClS$: C, 58.03; H, 4.17; N, 14.10; S, 11.06; Cl, 12.23. Found: C, 57.33; H, 4.06; N, 14.27; S, 10.99; Cl, 12.74.

EXAMPLE 43

2-[(5-Chloro-1H-benzimidazol-2-yl)sulfinyl]-methyl]benzenamine

The title compound (1.41 g), m.p. 165–166° C., was prepared by the method of Example 3 using 2.00 g of the title product of Example 42 instead of the title product of Example 2. Anal. Calc'd. for $C_{14}H_{12}N_3ClOS$: C, 54,99; H, 3.96; N, 13.74; S, 10.48; Cl, 11.59. Found: C, 54.40; H, 3.86; N, 13.47; S, 10.83; Cl, 12.05.

EXAMPLE 44

2-[[(5-Ethoxy-1H-benzimidazol-2-yl)thio]-methyl]benzenamine monohydrate

The title compound was prepared by the method of Example 1 using 3.00 g of 2-mercapto-5-ethoxybenzimidazole instead of 2-mercaptobenzimidazole and 2.76 g of 2-(chloromethyl)aniline hydrochloride instead of 2-(chloromethyl)-N,N-dimethylaniline in 250 ml of isopropyl alcohol. The basic extraction used 5% sodium hydroxide instead of sodium carbonate. Crystallization during concentration of the dichloromethane extract gave 2.60 g of the title compound as the monohydrate: m.p. 87–89° C. Anal. Calc'd. for $C_{16}H_{17}N_3OS*H_2O$: C, 63.76; H, 5.68; N, 13.94; S, 10.64. Found: C, 63,65; H, 5.74; N, 13.89; S, 10.89.

EXAMPLE 45

2-[[(5-Ethoxy-1H-benzimidazol-2-yl)sulfinyl]-methyl]benzenamine

The title compound was prepared by the method of Example 3 using 2.30 g of the title product of Example 44 instead of the title product of Example 2. The reaction mixture was washed with 10% aqueous potassium carbonate, dried over sodium sulfate, filtered, and concentrated in vacuo to dryness. Trituration with diethyl ether gave 1.95 g of the title compound: m.p. 154–155° C. Anal. Calc'd. for $C_{16}H_{17}N_3O_2S$: C, 60.93; H, 5.43; N, 13.32; S, 10.17. Found: C, 60.59; H, 5.36; N, 13.23; S, 10.27.

EXAMPLE 46

2-[[[(5-(Trifluoromethyl)-1H-benzimidazol-2-yl]thio]methyl]benzenamine

The title compound was prepared by the method of Example 1 using 4.36 g of 2-mercapto-5-(trifluoromethyl) benzimidazole instead of 2-mercaptobenzimidazole and 3.56 g of 2-(chloromethyl)aniline hydrochloride instead of 2-(chloromethyl)-N,N-dimethylaniline in isopropyl alcohol. The basic extraction used 5% sodium hydroxide instead of sodium carbonate. Washing the solid residue from the dichloromethane extract with additional dichloromethane gave 2.40 g of the title compound: m.p. ca. 155° C. Anal. Calc'd. for $C_{15}H_{12}N_3F_3S$: C, 55.72; H, 3.74; N, 13.00; S, 9.92; F, 17.63. Found: C, 55.55; H, 3.68; N, 13.10; S, 10.12; F, 17.38.

EXAMPLE 47

2-[[[(5-(Trifluoromethyl)-1H-benzimidazol-2-yl]sulfinyl]methyl]benzenamine

The title compound was prepared by the method of Example 3 using 2.00 g of the title product of Example 46 instead of the title product of Example 2. The reaction mixture, which contained no precipitate, was concentrated in vacuo. Crystallization during the concentration gave 568 mg (in three crops) of the title compound: m.p. 152–152.5° C. Anal. Calc'd. for $C_{15}H_{12}N_3F_3OS$: C, 53.09; H, 3.56; N, 12.38; S, 9.45; F, 16.80. Found: C, 53.23; H, 3.61; N, 12.48; S, 9.64; F, 16.89.

EXAMPLE 48

2-[(1H-Benzimidazol-2-yl)thiomethyl]-4-(trifluoromethyl)benzenamine

To a cold (ca. 0° C.) solution of 10.0 g (62 mMol) of 4-(trifluoromethyl)aniline and 6.6 g (65 mMol) of triethylamine in 100 ml of dichloromethane was added dropwise 7.9 g (65 mMol) of pivaloyl chloride. After stirring overnight, the mixture was poured into water. The aqueous layer was washed with additional dichloromethane and the organic layers were combined. The organic extracts were washed with three portions of water, dried over magnesium sulfate, filtered, and concentrated in vacuo to dryness. The residue was recrystallized from hexane, giving 14.2 g of the N-acylated aniline derivative. A mixture of 17.2 g of the N-acylated aniline derivative and 24 ml or redistilled tetramethylethylenediamine was stirred in diethyl ether cooled to about –5° C. in an ice-methanol bath. As the temperature was maintained at or below 5° C., 100 ml of 1.55 M butyllithium in hexane was added to form the aromatic carbanion. After being allowed to warm to room temperature, the mixture was stirred for about four hours. Formulation of the carbanion was effected by adding 15 ml of dimethylformamide dropwise at –5° C. The reaction mixture was partitioned between water and diethylether. The water layer was separated and washed with additional diethyl ether. The ether layers were combined, dried over magnesium sulfate, filtered, and concentrated in vacuo to an oil. Column chromatography on silica gel gave 12.9 g of N-acylated 2-amino-5-(trifluoromethyl)benzaldehyde as a solid. The benzaldehyde derivative (6.3 g) was converted to the corresponding benzyl alcohol derivative by reaction in 60 ml of ethanol with 1.05 g of sodium borohydride, added as a solution in 10 ml of aqueous 0.6 N sodium hydroxide. The borohydride solution was acidified with dilute hydrochloric and concentrated in vacuo to dryness. The residual solid was washed thoroughly with water and air-dried, giving 6.2 g of the benzyl alcohol derivative. A solution of 3 g of the benzyl alcohol derivative in 30 ml of dioxane was heated at about 80° C. for about four hours with 40 ml of concentration aqueous hydrochloric acid. Upon cooling, the reaction mixture was concentrated to dryness under a stream of nitrogen. The residue was washed thoroughly with diethyl ether, giving 2-(chloromethyl)-4-(trifluoromethyl)aniline hydrochloride. Using the general method of Example 1 with 1.56 g of 2-(chloromethyl)-4-(trifluoromethyl)aniline hydrochloride instead of 2-(chloromethyl)-N,N-dimethylaniline produced the title compound. The reaction mixture, which contained no precipitate, was concentrated in vacuo to dryness. The residue was partitioned between dichloromethane and 5% aqueous sodium hydroxide instead of sodium carbonate. The dichloromethane extract was dried over sodium sulfate, filtered, and concentrated in vacuo to a gum. Recrystallization from dichloromethane gave 290 mg of the title compound: m.p. 130–137° C. Anal. Calc'd. for $C_{15}H_{12}N_3F_3S$: C, 55.72; H, 3.74; N, 13.00; S, 9.92; F, 17.63. Found: C, 55.62; H, 3.59; N, 13.02; S, 10.25; F, 17.27.

EXAMPLE 49

2-[(1H-Benzimidazol-2-yl)sulfinylmethyl]-4-(trifluoromethyl)benzenamine

The title compound was prepared by the method of Example 3 using 530 mg of the title product of Example 48 instead of the title product of Example 2. Washing the precipitate from the reaction mixture with chloroform gave 465 mg of the title compound: m.p. 185–187° C. Anal. Calc'd. for $C_{15}H_{12}N_3F_3S$: C, 53,09; H, 3.56; N, 12.38; S, 9.45; F, 16.80. Found: C, 52.39; H, 3.41; N, 12.17; S, 9.66; F, 16.52.

EXAMPLE 50

2-[(1H-Benzimidazol-2-yl)thiomethyl]-4-butylbenzenamine

The title compound was prepared by the method of Example 1 using 1.08 g of 4-butyl-2-(chloromethyl)aniline hydrochloride instead of 2-(chloromethyl)-N,N-dimethylaniline. The reaction mixture was concentrated in vacuo to dryness. The residue was partitioned between dichloromethane and 5% aqueous sodium hydroxide instead of sodium carbonate. The dichloromethane extract was dried over sodium sulfate, filtered, and concentrated in vacuo to an oil. Trituration with hexane gave a solid that was recrystallized from diethyl ether-hexane to give the title compound: m.p. 108–109.5° C. The compound was used in subsequent reactions without further purification.

EXAMPLE 51

2-[(1H-Benzimidazol-2-yl)sulfinylmethyl]-4-butylbenzenamine

The title compound was prepared by the method of Example 3 using 487 mg of the title product of Example 50 instead of the title product of Example 2. The precipitate from the reaction mixture was collected, giving 351 mg of the title compound: m.p. 146–148° C. Anal. Calc'd. for $C_{18}H_2N_3OS$: C, 66.03; H, 6.46; N, 12.83; S, 9.79. Found: C, 65.69; H, 6.50; N, 12.85; S. 9.79.

EXAMPLE 52

2-[(1H-Benzimidazol-2-yl)thiomethyl]-5,6-dimethylbenzenamine

The title compound was prepared by the method of Example 1 using 3.00 g of 2-(chloromethyl)-5,6-dimethylaniline hydrochloride instead of 2-(chloromethyl)-N,N-dimethylaniline in isopropyl alcohol. The basic extraction used 5% sodium hydroxide instead of sodium carbonate. The solid residue from the dichloromethane extract gave, without further purification, 3.09 g of the title compound. Anal. Calc'd. for $C_{16}H_{17}N_3S$: C, 67.81; H, 6.05; N, 14.83; S, 11.31. Found: C, 67.46; H, 6.36; N, 14.40; S, 10.90.

EXAMPLE 53

2-[(1H-Benzimidazol-2-yl)sulfinylmethyl]-5,6-dimethylbenzenamine ¼ hydrate

The title compound was prepared by the method of Example 3 using 2.97 g of the title product of Example 52 instead of the title product of Example 2. The reaction mixture was concentrated in vacuo to dryness. The residue was washed with diethyl ether and redissolved in 400 ml of 15% (by volume) of methanol in dichloromethane. The organic solution was washed with 5% aqueous potassium carbonate, dried over sodium sulfate, filtered, and concentrated in vacuo. Crystallization during the concentration gave 1.36 g of the title compound: m.p. 160° C. (decomp). Anal. Calc'd. for $C_{16}H_{17}N_3OS*¼ H_2O$: C, 63.24; H, 5.80; N, 13.85; S, 10.55. Found: C, 62.72; H, 5.65; N, 13.58; S, 10.50

EXAMPLE 54

2-[(1H-Benzimidazol-2-yl)thiomethyl]-3,6-dimethylbenzenamine

The title compound was prepared by the method of Example 1 using 2.00 g of 2-(chloromethyl)-3,6-dimethylaniline hydrochloride instead of 2-(chloromethyl)-N,N-dimethylaniline in isopropyl alcohol. The basic extraction used 10% sodium hydroxide instead of sodium carbonate. Crystallization during concentration of the dichloromethane extract gave 1.60 g of the title compound. Anal. Calc'd. for $C_{16}H_{17}N_3S$: C, 67.81; H, 6.05; N, 14.83; S, 11.31. Found: C, 67.20; H, 6.03; N, 14.82; S, 11.29.

EXAMPLE 55

2-[(1H-Benzimidazol-2-yl)sulfinylmethyl]-3,6-dimethylbenzenamine monohydrate The title compound was prepared by the method of Example 3 using the title product of Example 54 instead of the title product of Example 2. The reaction mixture was concentrated in vacuo to dryness. The residue was washed with diethyl ether and redissolved in 400 ml of 10% (by volume) of methanol in dichloromethane. The organic solution was washed with 10% aqueous potassium carbonate, dried over sodium sulfate, filtered, and concentrated in vacuo. The resultant residue was washed with diethylether to give 621 mg of the title compound: m.p. 144–145° C. Anal. Calc'd. for $C_{16}H_{17}N_3OS*H_2O$: C, 60.55; H, 6.03; N, 13.24; S, 10.10. Found: C, 60.40; H, 5.69; N, 13.05; S, 9.98.

EXAMPLE 56

2-[(1H-Benzimidazol-2-yl)thiomethyl]-4-chloro-6-methylbenzenamine

The title compound was prepared by the method of Example 1 using 4.3 g of 2-(chloromethyl)-4-chloro-6-methylaniline hydrochloride instead of 2-(chloromethyl)-N,N-dimethylaniline in isopropyl alcohol. The basic extraction used 10% sodium hydroxide instead of sodium carbonate. The solid residue from the dichloromethane extract was

EXAMPLE 57

2-[(1H-Benzimidazol-2-yl)sulfinylmethyl]-4-chloro-6-methylbenzenamine hemihydrate The title compound was prepared by the method of Example 3 using 3.12 g of the title product of Example 56 instead of the title product of Example 2. The reaction mixture was concentrated in vacuo to dryness. The residue was dissolved in 400 ml of 5% (by volume) of methanol in chloroform. The organic solution was washed with 10% aqueous potassium carbonate, which was then backwashed with dichloromethane. The organic layers were combined, dried over sodium sulfate, filtered, and concentrated in vacuo. Washing the residue with diethyl ether gave 674 mg of the title compound: m.p. 168–169° C. Anal. Calc'd. for $C_{15}H_{14}N_3ClOS*½H_2O$: C, 54.79; H, 4.29; N, 12.78; S, 9.75. Found: C, 54.59; H, 4.43; N, 12.64; S, 9.88.

EXAMPLE 58

2-[(1H-Benzimidazol-2-yl)thiomethyl]-4-chloro-6-methoxy-3-methylbenzenamine

The title compound was prepared by the method of Example 1 using 2.50 g of 2-(chloromethyl)-4-chloro-6-methoxy-3-methylaniline hydrochloride instead of 2-(chloromethyl)-N,N-dimethylaniline in isopropyl alcohol. The precipitate from the reaction mixture was partitioned between dichloromethane and 5% aqueous sodium hydroxide instead of sodium carbonate. The dichloromethane extract was dried over sodium sulfate, filtered, and concentrated in vacuo to a solid. Trituration with hexane gave 2.23 g of the title compound: m.p. 146–148° C. (partial melting at ca. 100° C. with solidification). Anal. Calc'd. for $C_{16}H_{16}N_3ClOS$: C, 57.57; H, 4.83; N, 12.59; S, 9.60; Cl, 10.62. Found: C, 57.49; H, 4.83; N. 12.40; S, 9.55; Cl, 10.80.

EXAMPLE 59

2-[(1H-Benzimidazol-2-yl)sulfinylmethyl]-4-chloro-6-methoxy-3-methylbenzenamine

The title compound was prepared by the method of Example 3 using 2.00 g of the title product of Example 58 instead of the title product of Example 2. The reaction mixture, after clarification by filtration, was washed with 10% aqueous potassium carbonate, dried over sodium sulfate, filtered, and concentrated in vacuo. Washing the residue with diethyl ether gave 1.19 g of the title compound: m.p. 163–164° C. Anal. Calc'd. for $C_{16}H_{16}N_3ClO_2S$: C, 54.93; H, 4.61; N, 12.01; S, 9.16; Cl, 10.13. Found: C, 54.68; H, 4.54; N, 11.56; S, 8.89; Cl, 10.29.

EXAMPLE 60

2-[[(5-Ethoxy-1H-benzimidazol-2-yl)thio]-methyl]-4-methylbenzenamine

The title compound was prepared by the method of Example 1 using 3.00 g of 2-mercapto-5-ethoxybenzimidazole instead of 2-mercaptobenzimidazole and 3.71 g of 2-(chloromethyl)-4-methylaniline hydrochloride instead of 2-(chloromethyl)-N,N-dimethylaniline in isopropyl alcohol. The basic extraction used 10% sodium hydroxide instead of sodium carbonate. Crystallization during concentration of the dichloromethane extract gave 2.13 g of the title compound, which was used in subsequent reactions without further purification.

EXAMPLE 61

2-[[(5-Ethoxy-1H-benzimidazol-2-yl)sulfinyl]-methyl]-4-methylbenzenamine

The title compound was prepared by the method of Example 3 using 1.90 g of the title product of Example 60 instead of the title product of Example 2. The reaction mixture, which contained no precipitate, was concentrated in vacuo to dryness. Trituration with diethyl ether gave 1.19 g of the title compound: m.p. 144–145° C. Anal. Calc'd. for $C_{17}H_{19}N_3O_2S$: C, 61.98; H, 5.81; N, 12.76; S, 9.73. Found: C, 61.38; H, 5.80; N, 12.57; S, 9.85.

EXAMPLE 62

2-[(5-Methyl-1H-benzimidazol-2-yl)thio]methyl]-5,6-dimethylbenzenamine

The title compound was prepared by the method of Example 1 using 207 mg of 2-mercapto-5-methylbenzimidazole instead of 2-mercaptobenzimidazole and 260 mg of 2-(chloromethyl)-5,6-dimethylaniline hydrochloride instead of 2-(chloromethyl)-N,N-dimethylaniline in isopropyl alcohol. The basic extraction used 10% sodium hydroxide instead of sodium carbonate. The dichloromethane extract was dried over sodium sulfate, filtered, and concentrated in vacuo to 274 mg of the title compound as a gum. The compound was used in subsequent reactions without further purification.

EXAMPLE 63

2-[[(5-Methyl-1H-benzimidazol-2-yl)sulfinyl]-methyl]-5,6-dimethylbenzenamine hemihydrate The title compound (45 mg), m.p. 141–143° C., was prepared by the method of Example 3 using 254 mg of the title product of Example 62 instead of the title product of Example 2. Anal. Calc'd. for $C_{17}H_{19}N_3OS*H_2O$: C, 63.33; H, 5.94; N, 13.03; S, 9.94. Found: C, 63.74; H, 5.91; N, 12.54; S, 9.73.

EXAMPLE 64

2-[[[(5-(Trifluoromethyl)1-1H-benzimidazol-2-yl]thio]methyl]-3,6-dimethylbenzenamine The title compound was prepared by the method of Example 1 using 529 mg of 2-mercapto-5-(trifluoromethyl)benzimidazole instead of 2-mercaptobenzimidazole and 500 mg of 2-(chloromethyl)-3,6-dimethylaniline hydrochloride instead of 2-(chloromethyl)-N,N-dimethylaniline in isopropyl alcohol. The basic extraction used 10% sodium hydroxide instead of sodium carbonate. The dichloromethane extract was dried over sodium sulfate, filtered, and concentrated in vacuo to 590 mg of the title compound as a gum. The compound was used in subsequent reactions without further purification.

EXAMPLE 65

2-[[[(5-(Trifluoromethyl)1-1H-benzimidazol-2-yl]sulfinyl]-3,6-dimethylbenzenamine The title compound was prepared by the method of Example 3 using 578 mg of the title product of Example 64 instead of the title product of Example 2. The reaction mixture, which contained no precipitate, was washed with 5% aqueous potassium carbonate, dried over sodium sulfate, filtered, and concentrated in vacuo to a gum. Crystallization from acetonitrile gave 126 mg of the title compound. Anal. Calc'd. for $C_{17}H_{16}N_3FOS$: C, 55.58; H, 4.39; N, 11.44; S, 8.73; F, 15.51. Found: C, 55.43; H, 4.32; N, 11.48; S, 8.92; F, 15.31.

EXAMPLE 66

2-[[[(5-(Trifluoromethyl)1-1H-benzimidazol-2-yl] thio]methyl]-6-methoxybenzenamine The title compound was prepared by the method of Example 1 using 1.09 g of 2-mercapto-5-(trifluoromethyl) benzimidazole instead of 2-mercaptobenzimidazole and 1.04 g of 2-(chloromethyl)-6-methoxyaniline hydrochloride instead of 2-(chloromethyl)-N,N-dimethylaniline in isopropyl alcohol. The basic extraction used 10% sodium hydroxide instead of sodium carbonate. The dichloromethane extract was dried over sodium sulfate, filtered, and concentrated in vacuo to an oil. Trituration with 1:1 (by volume) diethyl ether-hexane gave 1.16 g of the title compound as a solid: m.p. ca. 130–148° C. The compound was used in subsequent reactions without further purification.

EXAMPLE 67

2-[[[(5-(Trifluoromethyl)1-1H-benzimidazol-2-yl] sulfinyl]methyl]-6-methoxybenzenamine The title product of Example 66 (945 mg, 2.68 mMol) was dissolved in about 1 liter of warmed chloroform, filtered, and cooled to about −5° C. A solution of 600 mg (ca. 2.95 mMol) of ca. 85% M-chloroperbenzoic acid in 20 ml of chloroform was added and the mixture stirred for about one hour. Fine granular potassium carbonate (5 g) was added and the mixture was stirred for 20 hours, after which the insolubles were removed by filtration. The filtrate was passed through a pad of granular potassium carbonate and concentrated in vacuo to a gum. The gum was triturated with diethyl ether. The ether supernatant was removed by decanting and allowed to stand, giving 219 mg of a solid. The remaining gum was again triturated with diethyl ether, giving 227 mg additional solid. The solids were combined and dissolved in chloroform containing a small amount of methanol. The solution was washed with 5% aqueous potassium carbonate, dried over sodium sulfate, filtered, and concentrated in vacuo to dryness. Chromatography on silica gel gave, after washing the residue with hexane, 60 mg of the title compound. Anal. Calc'd. for $C_{16}H_{14}N_3F_3O_2S$: C, 52.03; H, 3.82; N, 11.38; S, 8.68; F, 15.43. Found: C, 52.01; H, 3.85; N, 11.24; S, 8.62; F, 15.05.

EXAMPLE 68

Methyl 2-amino-3-[(1H-benzimidazol-2-yl) thiomethyl]benzoate

The title compound was prepared by the method of Example 1 using 1.27 g of methyl 2-amino-3-(chloromethyl) benzoate hydrochloride (prepared from methyl 2-amino-3-(methylsulfinylmethyl)benzoate as reported by J. P. Chupp et al., *J. Org. Chem.*, 49, 4711 (1984) instead of 2-(chloromethyl)-N,N-dimethylaniline in isopropyl alcohol. Recrystallization of the title compound from diethyl ether gave 1.72 g of the title compound in three crops. Anal. Calc'd. for $C_{16}H_{15}N_3O_2S$: C, 61.32; H, 4.82; N, 13.41; S, 10.23. Found: C, 60.73; H, 4.86; N, 12.87; S, 9.67.

EXAMPLE 69

Methyl 2-amino-3-[(1H-benzimidazol-2-yl) sulfinylmethyl]benzoate hydrate

The title compound was prepared by the method of Example 3 using 1.55 g of the title product of Example 68 instead of the title product of Example 2. The precipitate from the reaction mixture was collected and redissolved in 10% (by volume) of methanol in diethyl ether. The organic solution was washed with 5% aqueous potassium carbonate, dried over sodium sulfate, filtered, and concentrated in vacuo. The resultant residue was washed with diethyl ether to give 496 mg of the title compound. Anal. Calc'd. for $C_{16}H_{15}N_3O_3S*H_2O$: C, 55.32; H, 4.35; N, 12.10; S, 9.23. Found: C, 55.01; H, 4.78; N, 11.86; S, 9.04.

EXAMPLE 70

Ethyl 4-amino-3-[(1H-benzimidazol-2-yl) thiomethyl]benzoate

Ethyl 4-amino-3-(chloromethyl)benzoate hydrochloride was prepared from 20.0 g of ethyl 4-aminobenzoate using the method reported by J. P. Chupp et al., *J. Org. Chem.*, 49, 4711 (1984). The title compound was then prepared by the method of Example 1 using 1.75 g of ethyl 4-amino-3-(chloromethyl)benzoate hydrochloride instead of 2-(chloromethyl)-N,N-dimethylaniline in isopropyl alcohol. The basic extraction used 10% sodium hydroxide instead of sodium carbonate. Washing to solid residue from the dichloromethane extract with diethyl ether gave 865 mg of the title compound: m.p. 174–176° C. Anal. Calc'd. for $C_{17}H_{17}N_3O_2S$: C, 62.37; H, 5.23; N, 12.83; S, 9.79. Found: C, 61.52; H, 5.31; N, 12.54; S, 9.72.

EXAMPLE 71

Ethyl 4-amino-3-[(1H-benzimidazol-2-yl) sulfinylmethyl]benzoate hemihydrate

The title compound (528 mg), m.p. 192–194° C., was prepared by the method of Example 3 using 781 mg of the title product of Example 70 instead of the title product of Example 2. Anal. Calc'd. for $C_{17}H_{17}N_3O_3S*1/2\ H_2O$: C, 57.93; H, 4.86; N, 11.92; S, 9.10. Found: C, 57.75; H, 4.73; N, 11.96; S, 9.36.

EXAMPLE 72

Ethyl 4-amino-3-[[(5-methoxy-1H-benzimidazol-2-yl)thio]methyl]benzoate

The title compound was prepared by the method of Example 1 using 1.30 g of 2-mercapto-5-methoxybenzimidazole instead of 2-mercaptobenzimidazole and 1.80 g of ethyl 4-amino-3-(chloromethyl)benzoate hydrochloride (prepared as for Example 70) instead of 2-(chloromethyl)-N,N-dimethylaniline in isopropyl alcohol. The basic extraction used 10% sodium hydroxide instead of sodium carbonate and 1,2-dichloroethane instead of dichloromethane. The 1,2-dichloroethane extract was dried over sodium sulfate, filtered, and concentrated in vacuo to a gum. Recrystallization from diethyl ether-hexane gave 650 mg of the title compound: m.p. 140–146° C. Anal. Calc'd. for $C_{18}H_{19}N_3O_3S$: C, 60.49; H, 5.36; N, 11.76; S, 8.90. Found: C, 60.27; H, 5.44; N, 11.39; S, 8.70.

EXAMPLE 73

Ethyl 4-amino-3-[[(5-methoxy-1H-benzimidazol-2-yl)sulfinyl]methyl]benzoate

The title compound was prepared by the method of Example 3 using 557 mg of the title product of Example 72 instead of the title product of Example 2. The reaction mixture was passed three times through a column of potassium carbonate powder and concentrated in vacuo to dryness. Crystallization for acetonitrile gave 257 mg of the title compound. Anal. Calc'd. for $C_{18}H_{19}N_3O_4S$: C, 57.90; H, 5.13; N, 11.25; S, 8.59. Found: C, 57.63; H, 5.15; N, 11.32; S, 8.65.

EXAMPLE 74

2-[[5,6-Dimethoxy-1H-benzimidazol-2-yl)thio] methyl]benzenamine

The title compound was prepared by the method of Example 1 using 1.5 g of 2-mercapto-5,6-dimethoxybenzimidazole instead of 2-mercaptobenzimidazole and 1.3 g of 2-(chloromethyl) aniline hydrochloride instead of 2-(chloromethyl)-N,N-dimethylaniline in isopropyl alcohol. The precipitate from the reaction mixture was triturated with aqueous potassium carbonate, collected by filtration, and dried to give 1.9 g of the title compound, which was used in subsequent reactions without further purification.

EXAMPLE 75

2-[[5,6-Dimethoxy-1H-benzimidazol-2-yl)sulfinyl] methyl]-4-methylbenzenamine

The title compound was prepared by the method of Example 3 using 1.9 g of the title product of Example 74 instead of the title product of Example 2. The reaction mixture was concentrated in vacuo to dryness. The residue was triturated sequentially with diethyl ether, aqueous sodium carbonate, and diethyl ether. Column chromatography on silica gel gave 50 mg of the title compound. Anal. Calc'd. for $C_{16}H_{17}N_3O_3S$: C, 57.99; H, 5.17; N. 12.68; S, 9.67. Found: C, 57.44; H, 5.19; N, 12.50; S, 9.80.

EXAMPLE 76

2-[(1H-Benzimidazol-2-yl)sulfinylmethyl]-4-fluorobenzenamine

A solution of 9.0 g (58 mMol) of 3-fluoro-6-nitrotoluene in 200 ml of ethyl acetate was hydrogenated at room temperature with 60 psi of hydrogen gas using 0.9 g of 5% palladium on charcoal as catalyst. The solution was filtered and concentrated to give 6.7 g of 4-fluoro-2-methylaniline as an oil. A mixture of 1.33 g of the oil and 1.57 of phthalic anhydride was heated at 160° C. for 30 minutes and cooled. The resultant solid was washed with methanol and air dried to give 1.96 of the phthalimide derivative of 4-fluoro-2-methylaniline, m.p. 189.5–190.5° C. [Anal. Calc'd. for $C_{15}H_{10}NFO_2$: C,70.58; H, 3.95; N, 5.49; S, 7.44. Found: C, 70.68; H,3.95; N, 5.42; F, 7.39.] Bromination of the methyl group was effected by heating at reflux under an incandescent light source a mixture of 567 mg (2.22 mMol) of the phthalimide derivative, 435 mg of N-bromosuccinimide, and 59 mg of benzoyl peroxide in 25 ml of carbon tetrachloride. After one hour the mixture was cooled to room temperature, filtered, and concentrated in vacuo to give 720 mg of the crude bromomethyl phthalimide derivative. Using the general method of Example 1 with 284 mg of this bromomethyl phthalimide derivative instead of 2-(chloromethyl)-N,N-dimethylaniline in isopropyl alcohol produced the phthalimide derivative of 2-[(1H-benzimidazol-2-yl)thiomethyl]-4-fluorobenzenamine. The residue from the dichloromethane extraction (as in Example 1) was washed with diethyl ether and purified by column chromatography, giving 190 mg of the phthalimide derivative as a white solid. Using the method of Example 3 with 104 mg (0.248 mmol) of this phthalimide derivative of 2-[(1H-benzimidazol-2-yl)thiomethyl]-4-fluorobenzenamine instead of the title product of Example 2 produced the corresponding sulfoxide. The reaction mixture was diluted with dichloromethane, washed with aqueous sodium bicarbonate, dried over sodium sulfate, filtered, and concentrated in vacuo to give 119 mg of the sulfoxide as an oil. The sulfoxide was stirred in a solution of 0.14 ml of hydrazine hydrate in 5 ml of ethanol for two hours to remove the phthalimide group. The mixture was concentrated in vacuo to a solid, which was washed sequentially with 3% aqueous ammonium hydroxide and water, and air-dried to give 50 mg of the title compound: m.p. 184–185° C. Anal. Calc'd. for $C_{14}H_{12}N_3FOS$: C, 58.12; H, 4.18; N, 14.52; F, 6.57. Found: C, 58.11; H, 4.21; N, 14.54; F, 6.34.

EXAMPLE 77

2-[(1H-Benzimidazol-2-yl)sulfinylmethyl]-3,4,5-trimethylbenzenamine hemihydrate

The title compound, m.p. 145° C. (softening) with decomp. at 235° C., was prepared by the method of Example 39 using 3,4,5-trimethylaniline instead of 4-methoxy-3,5-dimethylaniline and using sulfuric acid instead of hydrochloric acid during the reaction according to Example 2. Anal. Calc'd. for $C_{17}H_{19}N_3OS*H_2O$: C, 63.33; H, 6.25; N, 13.03; F, 9.95. Found: C, 63.53; H, 5.92; N, 13.16; F, 9.60.

EXAMPLE 78

2-[[(5-Methoxy-1H-benzimidazol-2-yl)sulfinyl] methyl]-4-methoxy-3,5-dimethylbenzenamine The title compound, m.p. 149–155° C., was prepared by the method of Example 39 using 2-mercapto-5-methoxybenzimidazole instead of 2-mercaptobenzimidazole. Anal. Calc'd. for $C_{18}H_{21}N_3O_3S$: C, 60.15; H, 5.89; N, 11.69; F, 8.92. Found: C, 59.71; H, 5.83; N, 11.56; F, 8.64.

EXAMPLE 79

3-[(1H-Benzimidazol-2-yl)thiomethyl]-2-pyridinamine hemihydrate

A mixture of 9.6 g (63 mMol) of 2-mercaptobenzimidazole and 7.7 g (62 mMol) of 3-hydroxymethyl-2-pyridinamine was dissolved in 60 ml of 48% aqueous hydrobromic acid and 60 ml of acetic acid and heated to reflux. After being cooled to room temperature, the mixture was poured into water and made alkaline with potassium carbonate. The oil that separated solidified upon addition of diethyl ether to the aqueous mixture. The solid was collected by filtration, washed with portions of diethyl ether and water, and air dried to yield 12.4 g of the title compound as an analytically pure hemihydrate. Structure assignment was supported by the nmr and infrared spectra and by elemental analysis. Anal. Calc'd. for $C_{13}H_{12}N_4S*1/2 H_2O$: C,58.84; H, 4.93; N, 21.11; S, 12.08. Found: C, 59.06; H, 4.48; N, 20.82; S, 12.16.

EXAMPLE 80

3-[(1H-Benzimidazol-2-ylsulfonyl)methyl]-2-pyridinamine

A suspension of 4.0 g (15 mMol) of 3-[(1H-benzimidazol-2-yl)thiomethyl]-2-pyridinamine hemihydrate (see Example 79) in 50 ml of dichloromethane was cooled in an ice bath. A solution of 3.0 g (15 mMol) of ca. 85% m-chloroperbenzoic acid in the minimum amount of dichloromethane needed to form a solution was then added dropwise with stirring. After addition was complete, another 3.0 g of ca. 85% m-chloroperbenzoic acid was added. The reaction was quenched with 10 drops of dimethylsulfide. The mixture was washed with saturated aqueous sodium bicarbonate. The organic phase was concentrated in vacuo and chromatographed on silica gel (using ethanol-dichloromethane-triethylamine as eluent). Initial fractions yielded 249 mg of the title sulfone. Structure assignment was supported by the nmr and infrared spectra and by elemental analysis. Anal. Calc'd. for $C_{12}H_{12}N_4SO_2$: C, 54.15; H, 4.19; N, 19.43. Found: C, 53.79; H, 4.09; N, 19.29.

EXAMPLE 81

3-[(1H-Benzimidazol-2-yl)sulfinylmethyl]-2-pyridinamine hydrate

Later fractions from the chromatographic separation of Example 80 yielded 653 mg of the title sulfoxide. Structure assignment was supported by the nmr and infrared spectra and by elemental analysis. Anal. Calc'd. for $C_{13}H_{12}N_4SO*H_2O$: C, 53.77; H, 4.16; N, 12.29; S, 11.04. Found: C, 53.59; H, 4.34; N, 18.93; S, 11.26.

EXAMPLE 82

3-[(1H-Benzimidazol-2-yl)thiomethyl]-N,N-dimethyl-2-pyridinamine

To a cold (ca. −78° C.) solution of 2.9 g (21 mMol) of 3-methyl-2-(N,N-dimethylamino)pyridine in 35 ml of tetrahydrofuran was added dropwise 15 ml (23 mMol) of 1.55 M butyllithium in hexane. The mixture was stirred at 0° C. for four hours and then recooled to ca. −78° C. Trimethyl borate (2.65 ml, ca. 23 mMol) was added dropwise and the mixture was stirred at 0° C. After one hour 2.9 ml of 30% hydrogen peroxide was added and the mixture was stirred at 25° C. After another hour, the reaction mixture was poured into water and extracted with several portions of diethyl ether. The combined ether extracts were dried over magnesium sulfate, filtered, and concentrated in vacuo to an oil. Chromatography on silica gel (using ethanol-toluene as eluent) yielded 600 mg of 3-hydroxymethyl-2-(N,N-dimethylamino)pyridine, as confirmed by the nmr and infrared spectra. Using the method of Example 79 with 3-hydroxymethyl-2-(N,N-dimethylamino) pyridinamine instead of 3-hydroxymethyl- 2-pyridinamine yielded the title compound, which was used in subsequent reactions without further purification. Structure assignment was supported by the nmr and infrared spectra.

EXAMPLE 83

3-[(1H-Benzimidazol-2-yl)sulfinylmethyl]-N,N-dimethyl-2-pyridinamine 1/3 hydrate The title compound was prepared by the method of Example 80 using 1.5 g of 3-[(1H-benzimidazol-2-yl)sulfinylmethyl]-N,N-dimethyl-2-pyridinamine (see Example 82) instead of 3-[(1H-benzimidazol-2-yl)thiomethyl]-2-pyridinamine hemihydrate and using chloroform as solvent instead of dichloromethane. Structure assignment was supported by the nmr and infrared spectra and by elemental analysis. Anal. Calc'd. for $C_{15}H_{16}N_4OS*1/3 H_2O$: C, 58.84; H, 5.48; N, 18.29; S, 10.44. Found: C, 59.24; H, 5.31; N, 18.10; S, 10.05.

EXAMPLE 84

6-[(1H-benzimidazol-2-yl)thiomethyl]-2-pyridinamine hemihydrate

To a cold (ca. 0° C.) solution of 86.4 g (0.88 mole) of 2-amino-6-methylpyridine and 101 g (0.96 mole) of triethylamine in 1.0 liter of dichloromethane was added dropwise a solution of 106.1 g (0.88 mole) of trimethylacetyl chloride in 100 ml of dichloromethane. After stirring an hour after addition was completed, the mixture was poured into water and the layers separated. The aqueous layer was extracted with dichloromethane. The organic layers were combined and washed with water, dried over magnesium sulfate, filtered, and concentrated in vacuo to an oil that crystallized upon standing. The solid was triturated with hexane and collected by filtration, giving 115 g of 2-(trimethylacetamido)-6-methylpyridine. A 22.6 g (0.12 mMol) portion of the amide derivative was suspended in 250 ml of carbon tetrachloride containing 22.9 g (0.12 mMol) of N-bromosuccinimide and 100 mg of 2,2'-azabisisobutyronitrile. The mixture was heated at reflux under a sun lamp for one hour, after which insolubles were removed by filtration. The filtrate was concentrated in vacuo to an oil consisting of a mixture of the 6-bromomethyl-2-(trimethylacetamido)pyridine and 6-dibromomethyl-2-(trimethylacetamido)pyridine derivatives. The crude mixture was heated at reflux for fifteen minutes with 11.7 g (78 mMol) of 2-mercaptobenzimidazole in 300 ml of isopropyl alcohol. Upon cooling, a precipitate formed and was collected and washed with portions of isopropyl alcohol and diethylether. The trimethylacetyl group was removed by heating at reflux for four hours in 300 ml of 10% aqueous hydrochloric acid. After cooling, the mixture was concentrated in vacuo to an oil. The oil was dissolved in water and made alkaline with aqueous potassium carbonate. The oil that separated solidified upon addition of dichloromethane to the aqueous mixture. The solid was collected by filtration, washed with portions of water and dichloromethane, and air dried to yield 9.6 g of the title compound as an analytically pure hemihydrate. (An additional 2.5 g of the title compound was isolated from the dichloromethane washes.) Structure assignment was supported by the nmr and infrared spectra and by elemental analysis. Anal. Calc'd. for $C_{13}H_{12}N_4S*1/2 H_2O$: C, 58.84; H, 4.93; N, 21.11; S, 12.08. Found: C, 59.03; H, 4.40; N, 20.90; S, 12.30.

EXAMPLE 85

6-[(1H-Benzimidazol-2-yl)sulfinylmethyl]-2-pyridinamine

A suspension of 5.0 g (18.8 mMol) of 6-[(1H-benzimidazol-2-ylthio)methyl]-2-pyridinamine hemihydrate (see Example 84) in 250 ml of chloroform was cooled to −5° C. A solution of 4.2 g (20 mMol) of ca. 85% m-chloroperbenzoic acid in chloroform was added dropwise with stirring. After an additional fifteen minutes, the reaction was quenched with several drops of dimethylsulfide and concentrated in vacuo. The residue was triturated with diethyl ether, filtered, and washed with diethyl ether, yielding 2.6 g of the title compound. Structure assignment was supported by the nmr and infrared spectra and by elemental analysis. Anal. Calc'd. for $C_{13}H_{12}N_4SO$: C, 57.33; H, 4.44; N, 20.57; S, 11.77. Found: C, 57.04; H, 4.42; N, 20.50; S, 11.87.

EXAMPLE 86

6-[[(4-Methyl-1H-benzimidazol-2-yl)-thio]methyl]-2-pyridinamine hemihydrate

A solution of 20 g (0.13 mole) of 2-methyl-6-nitroaniline in 22.9 ml of concentrated aqueous hydrochloric acid, 200 ml of tetrahydrofuran, and 350 ml of methanol was hydrogenated at room temperature using 25 psi. of hydrogen gas over 2.0 g of 5% palladium on carbon. The mixture was filtered and the filtrate was concentrated in vacuo. The residue was dissolved in 150 ml of ethanol and neutralized with 17.2 g (0.26 mole) of potassium hydroxide dissolved in 30 ml of water. Potassium ethylxanthate (23g, 0.155 mole) was added and the mixture was heated at reflux for 18 hours. Upon cooling, a solid was collected, washed with water, and air dried to yield 6.2 g of 2-mercapto-4-methylbenzimidazole, as confirmed by the nmr and infrared spectra. The title compound (1.5 g) was prepared by the method of Example 84 using 1.6 g of 2-mercapto-4-methylbenzimidazole instead of 2-mercaptobenzimidazole. Structure assignment was supported by the nmr and infrared spectra and by elemental analysis. Anal. Calc'd. for $C_{14}H_{14}N_4S*1/2\ H_2O$: C, 60.19; H, 5.01;N, 20.05; S, 11.45. Found: C, 60.49; H, 5.03; N, 20.41; S, 11.76.

EXAMPLE 87

6-[[(4-Methyl-1H-benzimidazol-2-yl)-sulfinyl] methyl]-2-pyridinamine

The title compound (450 mg) was prepared by the method of Example 85 using 600 mg (2.2 mMol) of 6-[[(4-methyl-1H-benzimidazol-2-yl)thio]methyl]-2-pyridinamine (see Example 8) instead of 6-[(1H-benzimidazol-2-yl) thiomethyl]-2-pyridinamine. Structure assignment was supported by the nmr and infrared spectra and by elemental analysis. Anal. Calc'd. for $C_{14}H_{14}N_4SO$: C, 58.72; H, 4.93; N, 19.57; S, 11.20. Found: C, 58.70; H, 4.86; N, 19.60; S, 10.88.

EXAMPLE 88

6-[[(5-Methyl-1H-benzimidazol-2-yl)thio]-methyl]-2-pyridinamine hemihydrate

A mixture of 12.2 g (0.1 mole) of 3,4-diaminotoluene, 35 ml of carbon disulfide, and 4.0 g (0.1 mole) of sodium hydroxide was heated at reflux in 350 ml of ethanol. After 2.5 hours the mixture was concentrated in vacuo. The residue was suspended in 200 ml of 4% aqueous hydrochloric acid, and the product was collected by filtration, washed sequentially with water and diethyl ether, and air dried to yield 12.2 g of 2-mercapto-5-methylbenzimidazole, as confirmed by the nmr and infrared spectra. The title compound (2.0 g) was prepared by the method of Example 84 using 1.6 g (9.7 mMol) of 2-mercapto-5-methylbenzimidazole instead of 2-mercaptobenzimidazole. Structure assignment was supported by the nmr and infrared spectra and by elemental analysis. Anal. Calc'd. for $C_{14}H_{14}N_4S$: C, 60.19; H, 5.01; N, 20.05; S, 11.47. Found: C, 59.80; H, 5.05; N, 20.00; S, 11.17.

EXAMPLE 89

6-[[(5-Methyl-1H-benzimidazol-2-yl)-sulfinyl] methyl]-2-pyridinamine

The title compound (240 mg) was prepared by the method of Example 85 using 1.0 g (3.7 mMol) of 6-[[(5-methyl-1H-benzimidazol-2-yl)thio]methyl]-2-pyridinamine (see Example 88) instead of 6-[(1H-benzimidazol-2-yl) thiomethyl]-2-pyridinamine. Structure assignment was supported by the nmr and infrared spectra and by elemental analysis. Anal. Calc'd. for $C_{14}H_{14}N_4SO$: C, 58.72; H, 4.93; N, 19.57; S, 11.20. Found: C, 58.62; H, 4.91; N, 19.60; S, 10.99.

EXAMPLE 90

6-[[(5-Methoxy-1H-benzimidazol-2-yl) -thio] methyl]-2-pyridinamine

The title compound was prepared by the method of Example 84 using 7.0 g of 2-mercapto-5-methoxybenzimidazole instead of 2-mercaptobenzimidazole. Structure assignment was supported by the nmr spectrum.

EXAMPLE 91

6-[[(5-Methoxy-1H-benzimidazol-2-yl)sulfinyl]-methyl]-2-pyridinamine

The title compound (940 mg) was prepared by the method of Example 85 using 4.67 g (16.3 mMol) of 6-[[(5-methoxy-1H-benzimidazol-2-yl)thio]methyl]-2-pyridinamine (see Example 90) instead of 6-[(1H-benzimidazol-2-yl) thiomethyl]-2-pyridinamine. Structure assignment was supported by the nmr and infrared spectra and by elemental analysis. Anal. Calc'd. for $C_{14}H_{14}N_4SO_2$: C, 55.62; H, 4.67; N, 18.53; S, 10.60. Found: C, 55.52; H, 4.59; N, 17.86; S, 10.35.

EXAMPLE 92

6-[[(5-Chloro-1H-benzimidazol-2-yl)thio]-methyl]-2-pyridinamine

A solution of 20 g (0.12 mole) of 3-chloro-6-nitroaniline in 350 ml of methanol was hydrogenated over 5% palladium on carbon to yield 24.9 g of the corresponding diamino compound. Reaction of the diamino compound with potassium ethylxanthate using the method described in Example 86.yielded 19 g of 5-chloro-2-mercaptobenzimidazole, as confirmed by elemental analysis. The title compound (1.8 g) was prepared by the method of Example 84 using 3.6 g (19 mMol) of 5-chloro-2-mercaptobenzimidazole instead of 2-mercaptobenzimidazole. Structure assignment was supported by the nmr and infrared spectra.

EXAMPLE 93

6-[[(5-Chloro-1H-benzimidazol-2-yl)-sulfinyl] methyl]-2-pyridinamine

The title compound (250 mg) was prepared by the method of Example 85 using 1.5 g (5.2 mMol) of 6-[[(5-chloro-1H-benzimidazol-2-yl)thio]methyl]-2-pyridinamine (see Example 92) instead of 6-[(1H-benzimidazol-2-yl)thiomethyl]-2-pyridinamine. Structure assignment was supported by the nmr spectrum and by elemental analysis. Anal. Calc'd. for $C_{13}H_{11}N_4ClSO$: C, 50.90; H, 3.61; N, 18.26; S, 10.45; Cl, 11.56. Found: C, 50.97; H, 3.60; N, 18.45; S, 10.47; Cl, 11.74.

EXAMPLE 94

6-[[[5-(Trifluoromethyl)-1H-benzimidazol-2-yl]thio] methyl]-2-pyridinamine

A solution of 50 g (0.24 mole) of 4-(trifluoromethyl)-2-nitroaniline in 500 ml of ethanol was hydrogenated over 10% palladium on carbon to yield 21.0 g of the corresponding diamino compound. Reaction of 20.0 g of the diamino compound with carbon disulfide using the method described in Example 88 yielded 22.9 g of 5-(trifluoromethyl)-2-mercaptobenzimidazole, as confirmed by elemental analysis. The title compound (1.5 g) was prepared by the method of Example 84 using 5.7 g (26 mMol) of 5-(trifluoromethyl)-2-mercaptobenzimidazole instead of 2-mercaptobenzimidazole. Structure assignment was supported by the nmr and infrared spectra.

EXAMPLE 95

6-[[[5-(Trifluoromethyl)-1H-benzimidazol-2-yl]sulfinyl]methyl]-2-pyridinamine

The title compound (900 mg) was prepared by the method of Example 85 using 1.5 g (4.6 mMol) of 6-[[[5-(trifluoromethyl)-1H-benzimidazol-2-yl]thio]methyl]-2-pyridinamine (see Example 94) instead of 6-[(1H-benzimidazol-2-yl)thiomethyl]-2-pyridinamine. Structure assignment was supported by the nmr and infrared spectra and by elemental analysis. Anal. Calc'd. for $C_{14}H_{11}N_4F_3SO$: C, 49.41; H, 3.26; N, 16.46; S, 9.42. Found: C, 49.42; H, 3.29; N, 16.30; S, 9.49.

EXAMPLE 96

6-[[(5-Ethoxy-1H-benzimidazol-2-yl)thio]-methyl]-2-pyridinamine

A solution of 51.3 g (0.28 mole) of 4-ethoxy-2-nitroaniline in methanol was hydrogenated over 5% palladium on carbon to yield 63.4 g of the corresponding diamino compound. Reaction of the diamino compound with potassium ethylxanthate using the method described in Example 86 yielded 43.4 g of 5-ethoxy-2-mercaptobenzimidazole, as confirmed by the nmr and infrared spectra. The title compound (1.0 g) was prepared by the method of Example 84 using 3.7 g of 5-ethoxy-2-mercaptobenzimidazole instead of 2-mercaptobenzimidazole. The title compound was used in subsequent reactions without further characterization.

EXAMPLE 97

6-[[(5-Ethoxy-1H-benzimidazol-2-yl)-sulfinyl]methyl]-2-pyridinamine

The title compound (700 mg) was prepared by the method of Example 85 using 900 mg (3.0 mMol) of 6-[[(5-ethoxy-1H-benzimidazol-2-yl)thio]methyl]-2-pyridinamine (see Example 96) instead of 6-[(1H-benzimidazol-2-ylthio]methyl]-2-pyridinamine. Structure assignment was supported by the nmr and infrared spectra and by elemental analysis. Anal. Calc'd. for $C_{15}H_{16}N_4SO_2$: C, 56.95; H, 5.10; N, 17.71; S, 10.14. Found: C, 56.67; H, 4.99; N, 17.48; S, 10.27.

EXAMPLE 98

6-[[(5,6-Dimethoxy-1H-benzimidazol-2-yl)-thio]methyl]-2-pyridinamine 3/4 hydrate A solution of 62.2 g (0.31 mole) of 3,4-dimethoxy-6-nitroaniline in tetrahydrofuran was hydrogenated with Raney nickel to yield 52.7 g of the corresponding diamino compound. Reaction of the diamino compound with potassium ethylxanthate using the method described in Example 86 yielded 59 g of 5,6-dimethoxy-2-mercaptobenzimidazole as confirmed by the nmr and infrared spectra. The title compound (1.9 g) was prepared by the method of Example 84 using 4.3 g of 5,6-dimethoxy-2-mercaptobenzimidazole instead of 2-mercaptobenzimidazole. Structure assignment was supported by the nmr and infrared spectra and by elemental analysis. Anal. Calc'd. for $C_{15}H_{16}N_4SO_2*3/4$ $H_2O$: C, 54.61; H, 5.30; N, 16.98; S, 9.70. Found: C, 54.75; H, 5.13; N, 17.08; S, 9.72.

EXAMPLE 99

6-[[(5,6-Dimethoxy-1H-benzimidazol-2-yl)-sulfinyl]methyl]-2-pyridinamine 1/4 hydrate The title compound (600 mg) was prepared by the method of Example 85 using 1.6 g (5.0 mMol) of 6-[[(5,6-dimethoxy-1H-benzimidazol-2-yl)thio]methyl]-2-pyridinamine (see Example 98) instead of 6-[(1H-benzimidazol-2-yl)thio-methyl]-2-pyridinamine. Structure assignment was supported by the nmr spectrum and by elemental analysis. Anal. Calc'd. for $C_{15}H_{16}N_4SO_3*1/4$ $H20$: C, 53.48; H, 4.90; N, 16.63; S, 9.52. Found: C, 53.54; H, 4.57; N, 16.45; S, 9.79.

EXAMPLE 100

6-[[(5,6-Dimethyl-1H-benzimidazol-2-yl)-thio]methyl]-2-pyridinamine

Reaction of 30 g (0.22 mole) of 4,5-dimethyl-1,2-phenylenediamine with potassium ethylxanthate using the method described in Example 86 yielded 19 g of 5,6-dimethyl-2-mercaptobenzimidazole, as confirmed by the nmr and infrared spectra and by elemental analysis. The title compound (3.0 g) was prepared by the method of Example 84 using 3.5 g of 5,6-dimethyl-2-mercaptobenzimidazole instead of 2-mercaptobenzimidazole. Structure assignment was supported by the nmr spectrum.

EXAMPLE 101

6-[[(5,6-Dimethyl-1H-benzimidazol-2-yl)-sulfinyl]methyl]-2-pyridinamine

The title compound was prepared by the method of Example 85 using 1.5 g (5.3 mMol) of 6-[[(5,6-dimethyl-1H-benzimidazol-2-yl)thio]methyl]-2-pyridinamine (see Example 100) instead of 6-[(1H-benzimidazol-2-yl)thio-methyl]-2-pyridinamine. Structure assignment was supported by the nmr spectrum and by elemental analysis. Anal. Calc'd. for $C_{15}H_{16}N_4SO$: C, 59.98; H, 5.37; N, 18.65; S, 10.67. Found: C, 59.67; H, 5.20; N, 18.83; S, 10.87.

EXAMPLE 102

6-[[(4,6-Dimethyl-1H-benzimidazol-2-yl)-thio]methyl]-2-pyridinamine

A solution of 5 g (0.03 mole) of 2,4-dimethyl-6-nitroaniline in methanol was hydrogenated over 5% palladium on carbon to yield 4.0 g of the corresponding diamino compound. Reaction of the diamino compound with potassium ethylxanthate using the method described in Example 86 yielded 4.9 g of 4,6-dimethyl-2-mercaptobenzimidazole, as confirmed by the nmr and infrared spectra and by elemental analysis. The title compound (1.5 g) was prepared by the method of Example 84 using 3.5 g (20 mMol) of 4,6-dimethyl-2-mercaptobenzimidazole instead of 2-mercaptobenzimidazole. Structure assignment was supported by the nmr spectrum.

EXAMPLE 103

6-[[(4,6-Dimethyl-1H-benzimidazol-2-yl)-sulfinyl]methyl]-2-pyridinamine

The title compound was prepared by the method of Example 85 using 1.0 g (3.5 mmol) of 6-[[(4,6-dimethyl- 1H-benzimidazol-2-yl)thio]methyl]-2-pyridinamine (see Example 102) instead of 6-[(1H-benzimidazol-2-yl)thiomethyl]-2-pyridinamine. Structure assignment was supported by the nmr and infrared spectra and by elemental analysis. Anal. Calc'd. for $C_{15}H_{16}N_4SO$: C, 59.98; H, 5.37; N, 18.65; S, 10.67. Found: C, 59.60; H, 5.32; N, 18.47; S, 10.75.

EXAMPLE 104

6-[[[5-(Hydroxymethyl)-1H-benzimidazol-2-yl]thio]methyl]-2-pyridinamine

The title compound (600 mg) was prepared by the method of Example 84 using 2.7 g of 5-hydroxymethyl-2-mercaptobenzimidazole instead of 2-mercaptobenzimidazole. Structure assignment was supported by the nmr spectrum.

EXAMPLE 105

6-[[[5-(Hydroxymethyl)-1H-benzimidazol-2-yl]sulfinyl]methyl]-2-pyridinamine 1/4 hydrate The title compound was prepared by the method of Example 85 using 350 mg of 6-[[[5-(hydroxymethyl)-1H-benzimidazol-2-yl]thio]methyl]-2-pyridinamine (see Example 104) instead of 6-[(1H-benzimidazol-2-yl)thiomethyl]-2-pyridinamine. Structure assignment was supported by the nmr and infrared spectra and by elemental analysis. Anal. Calc'd. for $C_{14}H_{14}N_4SO_2$*1/4 H2O: C, 54.80; H,4.60; N, 18.25; S, 10.44. Found: C, 54.85; H, 4.70; N, 18.01; S, 10.26.

EXAMPLE 106

6-[[(1H-Benzimidazol-2-yl)thio]methyl]-N-(2,2-dimethylpropyl)-2-pyridinamine

A suspension of 40 g (0.21 mole) of 2-(trimethylacetamido)-6-methylpyridine (prepared as described in Example 84) in 500 ml of water was heated to 70° C. Potassium permanganate (65 g, 420 mMol) was added in eight portions over four hours and the mixture was then heated at 90° C. After 18 hours the mixture was filtered hot. The filtrate was concentrated in vacuo to about 50 ml and adjusted to about pH 3 with concentrated hydrochloric acid. The resultant precipitate was collected, washed with water, and dried in vacuo to yield 7.5 g of the 6-carboxylic acid derivative. To a suspension of 7.0 g of the carboxylic acid derivative in 50 ml of cold (ca. 0° C.) tetrahydrofuran was added dropwise 85 ml (ca. 85 mMol) of 1 M borane in tetrahydrofuran. The mixture was allowed to stir at room temperature for two hours and at 50° C. for another 18 hours. After the mixture was allowed to cool, the reaction was quenched with water. The mixture made basic with 10% aqueous sodium hydroxide and extracted with several portions of ethyl acetate. The combined organic layers were dried over magnesium sulfate, filtered, and concentrated in vacuo to an oil. Chromatography on silica gel (using ethanol-dichloromethane as eluent) yielded 1.3 g of 6-hydroxymethyl-N-(2,2-dimethylpropyl)-2-pyridinamine, as confirmed by the nmr and infrared spectra. The title compound (1.9 g) was prepared by the method of Example 79 using 1.3 g (6.7 mMol) of 6-hydroxymethyl-N-(2,2-dimethylpropyl)-2-pyridinamine instead of 3-hydroxymethyl-2-pyridinamine. Structure assignment was supported by the nmr spectrum.

EXAMPLE 107

6-[[(1H-Benzimidazol-2-yl)sulfinyl]methyl]-N-(2,2-dimethylpropyl)-2-pyridinamine 1/4 hydrate The title compound (100 mg) was prepared by the method of Example 85 using 1.52 g (4.65 mMol) of 6-[[(1H-benzimidazol-2-yl)thio]methyl]-N-(2,2-dimethylpropyl)-2-pyridinamine (see Example 106) instead of 6-[[(1H-benzimidazol-2-yl)thio]methyl]-2-pyridinamine. Structure assignment was supported by the nmr and infrared spectra and by elemental analysis. Anal. Calc'd. for $C_{18}H_{22}N_4SO$*1/4 H20: C, 62.31; H, 6.48; N, 16.15; S, 9.24. Found: C, 62.19; H, 6.47; N, 15.76; S, 9.09.

EXAMPLE 108

6-[[(1H-Benzimidazol-2-yl)thio]methyl]-N-ethyl-2-pyridinamine

The title compound (2.1 g) was prepared by the method of Example 106 using 45 g (0.30 mole) of 2-acetamido-6-methylpyridine (prepared from 2-amino-6-methylpyridine as described in Example 84 using acetyl chloride instead of trimethylacetyl chloride) instead of 2-(trimethylacetamido)-6-methylpyridine. Structure assignment was supported by the nmr and infrared spectra.

EXAMPLE 109

6-[[(1H-Benzimidazol-2-yl)sulfinyl)]methyl]-N-ethyl-2-pyridinamine

The title compound was prepared by the method of Example 85 using 2.0 g (7.03 mMol) of 6-[[(1H-benzimidazol-2-yl)thio]methyl]-N-ethyl-2-pyridinamine (see Example 108) instead of 6-[[(1H-benzimidazol-2-yl)thio]methyl]-2-pyridinamine. Structure assignment was supported by the nmr and infrared spectra and by elemental analysis. Anal. Calc'd. for $C_{15}H_{16}N_4SO$: C, 59.98; H, 5.37; N, 18.65; S, 10.67. Found: C, 60.07; H, 5.37; N, 18.45; S, 10.61.

EXAMPLE 110

5-[[(1H-Benzimidazol-2-yl)thio]methyl]-2-pyridinamine 1/4 hydrate

The title compound was prepared by the general method described in Example 84 using 2-amino-5-methylpyridine instead of 2-amino-6-methylpyridine. The crystalline solid was collected and washed with portions of water and diethyl ether to yield 1.8 g of the title compound. Structure assignment was supported by the nmr and infrared spectra and by elemental analysis. Anal. Calc'd. for $C_{13}H_{12}N_4S$*1/4 $H_2O$: C, 59.86; H, 4.83; N, 21.48; S, 12.29. Found: C, 59.91; H, 4.67; N, 21.86; S, 12.45.

EXAMPLE 111

5-[[(1H-Benzimidazol-2-yl)sulfinyl]methyl]-2-pyridinamine 1/4 hydrate

The title compound was prepared by the method of Example 85 using 1.0 g (3.9 mMol) of 5-[[(1H-benzimidazol-2-yl)thio]methyl]-2-pyridinamine (see Example 110) instead of 6-[[(1H-benzimidazol-2-yl)thio)]methyl]-2-pyridinamine. Structure assignment was supported by the nmr and infrared spectra and by elemental analysis. Anal. Calc'd. for $C_{13}H_{12}N_4SO$*1/4 $H_2O$: C, 56.40; H, 4.55; N, 20.24; S, 11.58. Found: C, 56.35; H, 4.46; N, 20.25; S, 11.66.

EXAMPLE 112

2-[(4,6-Dimethyl-5-methoxy-2-phthalimidylphenyl)methylsulfonyl]-5-methoxy-1H-benzimidazole The 2-[[(5-methoxy-1H-benzimidazol-2-yl)thio]methyl]-4-methoxy-3,5-dimethylbenzenamine (221 mg, 0.45 mmol)

described in Example 78 was dissolved in 2.5 ml of $CH_2Cl_2$ and cooled in an ice bath. MCPBA (94 mg; 0.45 mmol) was dissolved in 1.0 ml of $CH_2Cl_2$ and added dropwise to the above solution. The reaction mixture was washed with dilute $K_2CO_3$. The organic layer was washed with water, dried over $MgSO_4$ and concentrated. The residue was purified by preparative thin-layer chromatography eluting with 40% EtOAc/hexane to give the title compound (185 mg, 81%): $^{13}C$ NMR (CDCl$_3$) δ167.9, 157.6, 134.2, 133.6, 133.1, 131.3, 129.3, 126.7 124.0, 123.6, 56.2, 55.3, 50.0, 15.6, 12.5.

EXAMPLE 113

2-[[(5-Chloro-1H-benzimidazol-2-yl)sulfinyl] methyl]-3,5-dimethyl-4-methoxybenzenamine According to the general procedure of Example 39, the phthalimide derivative of 2-hydroxymethyl-4-methoxy-3,5-dimethylaniline (0.622 g, 2 mmol) was reacted with 6-chloro-2-mercaptobenzimidozole, prepared according to the procedure described in U.S. Pat. No. 4,687,775 (0.369 g, 2.0 mmol), to give a residue which was purified on silica gel eluting with 20/80 ethyl acetate/hexane to give the requisite sulfide derivative (0.89 g, 93%). Analysis calc'd for $C_{25}H_{20}N_3O_3SCl$: C, 62.82; H, 4.22; N, 8.79. Found, C, 62.64; H, 4.40; N, 8.40. MS (EI) m/z=477 (M). This sulfide (0.177 g, 0.37 mmol) was oxidized with MCPBA (0.078 g. 0.37 mmol) according to the general procedure of Example 39 to afford a light yellow solid which was triturated with ether to give the phthalimidyl sulfinyl compound as a white solid (0.102 g, 56%). Analysis calc'd for $C_{25}H_{20}N_3O_4SCl.H_2O$: C, 58.40; H, 4.33; N, 8.21; found C, 58.40; H, 3.77; N, 7.39. MS (CI) m/z=494 (M+1). The phthalimidyl compound (62 mg, 0.13 mmol) was deprotected with hydrazine according to the general procedure of Example 39 to give the title compound (20 mg, 44%). Analysis calc'd for $C_{17}H_{18}N_3O_2SCl*0.3 H_2O$: C, 55.29; H, 5.08; N, 11.38. Found C, 55.33; H, 4.93; N, 11.12.

EXAMPLES 114–115

(+)-2-[[(5-Methoxy-1H-benzimidazol-2-yl)sulfinyl] methyl]-3,5-dimethyl-4-methoxybenzenamine (−)-2-[[(5-Methoxy-1H-benzimidazol-2-yl)sulfinyl] methyl]-3,5-dimethyl-4-methoxybenzenamine The phthalimide sulfinyl mixture of enantiomers from Example 39 (60 mg) derivative was resolved by chiral chromatography on a Daicel Chiralcel® OD column eluting with 20/80 isopropanol/heptane to give 6.9 mg of enantiomer 1 and 14 mg of enantiomer 2. To a solution of protected enantiomer 1 (6.9 mg, 0.014 mMol) in 1 ml ethanol, at 0° C. was added 1 drop of hydrazine hydrate and the solution was stirred for 1 hour at 0° C. and 0.5 hour at room temperature. The solvent was removed under vacuum and the residue was dissolved in chloroform, washed with aqueous dilute potassium carbonate, dried over potassium carbonate, filtered and concentrated in vacuo to give 3.5 mg (70%) of (+)-2-[[(5-methoxy-1H-benzimidazol-2-yl)sulfinyl]methyl]-3,5-dimethyl-4-methoxybenzenamine (Example 114). $[α]_D$=+90.9° (c=0.028 g/dL in methanol). Protected enantiomer 2 (14 mg, 0.028 mMol) was deprotected with hydrazine as described for enantiomer 1 to give (−)-2-[[(5-methoxy-1H-benzimidazol-2-yl)sulfinyl]methyl]-3,5-dimethyl-4-methoxybenzenamine (Example 115) (11 mg, 100%). $[α]_D$=−132° (c=0.025 g/dL in methanol).

EXAMPLE 116

N-[2-[[(6-methoxy-1H-benzimidazol-2-yl)sulfinyl] methyl]-3,5-dimethyl-4-methoxyphenyl]acetamide Paraformaldehyde (0.07 g, 2.3 mmol) was dissolved in concentrated $H_2SO_4$ (2.5 ml) at 0° C. and HCl gas was purged into the reaction mixture for 15 minutes. N-acetyl-4-methoxy-3,5-dimethylaniline (0.25 g, 1.3 mmol) was added, the HCl gas purge was resumed and continued for another 15 minutes. The reaction solution stirred at 0° C. for another 30 minutes and was poured into ice water. The precipitate of 2-chloromethyl-N-acetyl-4-methoxy-3,5-dimethylaniline was collected, washed with $H_2O$, dried under vacuum, and used without further purification. The 2-chloromethyl-N-acetyl-4-methoxy-3,5-dimethylaniline (0.142 g, 0.587 mmol) was added to a DMF (3 ml) solution of $K_2CO_3$ (0.24 g, 1.74 mmol) and 6-methoxy-2-mercaptobenzimidazole (0.115 g, 0.638 mmol). After stirring at room temperature overnight, the reaction solution was concentrated and residue obtained was dissolved in $CH_2Cl_2$. The organic layer was washed succesively with 10% citric acid, sat. $NaHCO_3$ solution and brine, dried over $MgSO_4$ and concentrated to give a residue. Purification on silica gel with 50/50 ethyl acetate/hexane gave the sulfide (79 mg, 36%). Analysis calc'd for $C_{20}H_{23}N_3O_3S*H_2O$: C, 59.53; H, 6.25; N, 10.41. Found C, 59.74; H, 5.92; N, 9.80. MS (EI) m/z=385 (M). The sulfide thus obtained (30 mg, 0.078 mmol) was treated with MCPBA as described in Example 39 to give the titled compound. Analysis calc'd for $C_{20}H_{23}N_3O_4S*0.5 H_2O$: C, 58.52; H, 5.89; N, 10.24. Found, C, 58.56; H, 5.69; N, 9.48. MS (EI) m/z=401 (M).

EXAMPLE 117

2-[(4,6-Dimethyl-5-methoxy-2-phthalimidylphenyl) methylsulfinyl]-6-chloro-1-isopropyl-1H-benzimidazole According to the general procedure of Example 39, the phthalimide derivative of 2-hydroxymethyl-4-methoxy-3,5-dimethylaniline (311 mg, 1.0 mmol) was reacted with 6-chloro-N-isopropyl-2-mercaptobenzimidazole (220 mg, 1.0 mmol, prepared by the general method described in U.S. Pat. No. 4,687,775) to afford 340 mg (65%) of the requisite sulfide. Analysis calc'd $C_{28}H_{27}N_3O_3SCl$: C, 64.67; H, 5.22; N, 8.06. Found: C, 64.51; H, 5.30; N, 7.39. The sulfide (320 mg, 0.61 mmol) was oxidized with MCPBA (100 mg, 0.58 mmol) according to the general procedure of Example 39 to afford the title compound (302 mg, 95%). Analysis Calc'd $C_{28}H_{26}N_3O_4SCl*3/4 H_2O$: C, 61.20, H, 5.04, N, 7.65. Found: C, 61.14, H, 4.80; N, 7.40.

EXAMPLE 118

2-[(4,6-Dimethyl-5-methoxy-2-phthalimidylphenyl) methylsulfinyl]-5-chloro-1-isopropyl-1H-benzimidazole According to the general procedure of Example 39, the phthalimide derivative of 2-hydroxymethyl-4-methoxy-3,5-dimethylaniline (311 mg, 1.0 mmol) was reacted with 5-chloro-1-isopropyl-2-mercaptobenzimidazole (prepared by the general method described in U.S. Pat. No. 4,687,775) to afford the requisite sulfide (126 mg, 24%). This sulfide (126 mg, 0.2 mmol) was oxidized with MCPBA (40 mg, 023 mmol) according to the general method of Example 39 to afford the title compound (95 mg, 90%). Analysis calc'd $C_{28}H_{26}N_3O_4SCl*1/4 H_2O$:: C, 62.22, H, 4.94, N, 7.77. Found: C, 62.03, H, 4.78; N, 7.42.

EXAMPLE 119

2-[[(1-Methyl-1H-imidazol-2-yl)sulfinyl]methyl]-3, 5-dimethyl-4-methoxybenzenamine According to the general procedure of Example 39, the phthalimide derivative of 2-hydroxymethyl-4-methoxy-3,5- dimethylaniline (311 mg; 0.001 mole) was reacted with 2-mercapto-1-methylimidazole (127 mg; 1.0 mmol) to give 181 mg (45%) of the desired sulfide. This sulfide (170 mg; 0.42 mmol) was oxidized with MCPBA (87 mg; 0.42 mmol) according to the general procedure of Example 39 to yield 139 mg (78%) of the sulfoxide. This phthalimide derivative (137 mg, 0.32 mmol) was deprotected with hydrazine according to the general procedure of Example 39 to give the title compound (66 mg, 73%). Analysis calc'd for $C_{14}H_{19}N_3SO_2$*1/2 $H_2O$: C, 55.61; H, 6.67; N, 13.90. Found C, 55.91, H, 6.17; N, 13.58. HRMS calc'd for $C_{14}H_{19}N_3SO_2$: 294.1274. Found 294.1272.

EXAMPLE 120

2-[[(1H-Imidazol-2-yl)sulfinyl]methyl]-3,5-dimethyl-4-methoxybenzenamine

According to the general procedure of Example 39, the phthalimide derivative of 2-hydroxymethyl-4-methoxy-3,5-dimethylaniline (311 mg; 1.0 mmol) was reacted with 2-mercaptoimidazole (100 mg; 1.0 mmol) to afford the requisite sulfide (159 mg, 41%). This sulfide (148 mg; 0.38 mmol) was oxidized with MCPBA (79 mg; 0.38 mmol) as described in Example 39 to give the corresponding sulfoxide (85 mg, 54%). This sulfoxide phthalimide derivative (85 mg, 0.21 mmol) was deprotected with hydrazine according to the general procedure of Example 39 to give a residue which was purified using prep-plate chromatography eluting with 10% $CH_3OH/CHCl_3$ to afford the title compound (24 mg, 42%). $^1$H NMR ($CD_3OD$) $\delta$2.09 (s, 3H), 2.19 (s, 3H), 3.59 (s, 3H), 4.50 (q, 2H), 6.53 (s, 1H), 7.31 (s, 2H). MS for $C_{13}H_{17}N_3SO_2$: 279, Found M+1:280.

EXAMPLE 121

2-[(4,6-Dimethyl-5-methoxy-2-phthalimidylphenyl) methylsulfinyl]-5-chloro-1-ethyl-1H-benzimidazole According to the general procedure of Example 39, the phthalimide derivative of 2-hydroxymethyl-4-methoxy-3,5-dimethylaniline (311 mg, 1.0 mmol) was reacted with N-ethyl-5-chloro-2-mercaptobenzimidazole (prepared by the general method of U.S. Pat. No. 4,687,775) to afford 390 mg (77%) of requisite sulfide. This sulfide (340 mg, 0.67 mmol) was oxidized with MCPBA (113 mg, 0.66 mmol) according to the general procedure of Example 39 to give the title compound (160 mg, 45%). $^1$H NMR ($CDCl_3$) $\delta$1.24 (t, 3H), 2.29(s, 3H), 2.32 (s, 3H), 3.68 (s, 3H), 4.17 (m, 2H) 4.52 (d, 1H), 5.27 (d, 1H), 6.92 (s, 1H), 7.18 (dd, 1H), 7.32 (d, 1H), 7.64 (d, 1H), 7.74 (t, 1H), 7.79 (t, 3H), 7.92 (d, 1H).

EXAMPLE 122

2-[(4,6-Dimethyl-5-methoxy-2-phthalimidylphenyl) methylsulfinyl]-6-chloro-1-ethyl-1H-benzimidazole According to the general procedure of Example 39, the phthalimide derivative of 2-hydroxymethyl-4-methoxy-3,5-dimethylaniline (311 mg, 1.0 mmol) was reacted with 6-chloro-N-isopropyl-2-mercaptobenzimidazole (prepared by similar method described in U.S. Pat. No. 4,687,775) to afford 230 mg (45%) of the requisite sulfide. This sulfide (230 mg, 0.45 mmol) was oxidized with MCPBA (74 mg, 0.43 mmol) according to the general procedure of Example 39 to afford the title compound 174 mg (73%). $^1$H NMR ($CDCl_3$): $\delta$1.22 (t, 3H), 2.28 (s, 3H), 2.39 (s, 3H), 3.19 (s, 3H), 4.19 (m, 2H), 4.50 (d, 1H), 5.37 (d, 1H), 6.88 (s, 1H); 7.14 (d, 1H) 7.27 (q, 2H), 7.53 (d, 1H), 7.74 (t, 1H), 7.80 (t, 1H), 7.89 (d, 1H).

EXAMPLE 123

2-[[[2-[[(6-Chloro-1-ethyl-1H-benzimidazol-2-yl) sulfinyl]methyl]-3,5-dimethyl-4-methoxyphenyl] amino]carbonyl]benzenecarboxylic acid hydrazide The title compound of Example 122 (65 mg, 0.12 mmol) was treated with hydrazine according to the general procedure of Example 39 to give 48 mg (100%) of the partially deprotected amine title compound. $^1$H NMR ($CDCl_3$) $\delta$1.31 (t, 3H), 2.28 (s, 3H), 2.32 (s, 3H), 3.65 (s, 3H), 4.16 (s, 1H), 4.32 (m, 2H), 4.48 (q, 2H), 7.19 (s, 1H), 7.31 (m, 1H), 7.49 (s, 1H), 7.59 (m, 2H), 7.70 (m, 1H), 7.80 (m, 2H).

EXAMPLE 124

2-[[[2-[[(5-Chloro-1-ethyl-1H-benzimidazol-2-yl) sulfinyl]methyl]-3,5-dimethyl-4-methoxyphenyl] amino]carbonyl]benzenecarboxylic acid hydrazide 2-[(4,6-Dimethyl-5-methoxy-2-phthalimidylphenyl) methylsulfinyl]-5-chloro-1-ethyl-1H-benzimidazole (Example 121) (66 mg, 0.13 mmol) was treated with hydrazine according to the procedure of Example 39 to give the crude acyl hydrazide as an oil which was triturated with ether to give the partially deprotected amine as the title compound (28 mg, 57%). $^1$H NMR $\delta$1.29, (t, 3H), 2.26 (s, 3H), 2.34 (s, 3H), 3.66 (s, 3H), 4.16 (s, 2H), 4.29 (m, 2H), 4.95 (q, 2H), 7.24 (s, 2H), 7.37 (s, 1H), 7.48 (s, 1H), 7.55 (m, 2H), 7.69 (m, 1H), 7.82 (m, 1H), 7.87 (s, 1H).

EXAMPLE 125

4-Methoxy-3,5-dimethyl-2-[(2-pyridinyl) sulfinylmethyl]benzenamine

The general procedure described in Tet. Lett. 27, 5385 (1986) was utilized employing the phthalimide derivative of 2-hydroxymethyl-4-methoxy-3,5-dimethylaniline of Example 78 (156 mg, 0.50 mmol) and of 2,2'-dipyridyl disulfide (143 mg, 0.65 mmol) to give a crude product which was chromatographed on prep-plate chromatography (3/7 ethyl acetate/hexane) to give the requisite sulfide (41 mg, 20%). Subsequent oxidation of the sulfide (38 mg, 0.09 mmol) with MCPBA (19 mg, 0.09 mmol) according to the general procedure of Example 39 gave 22 mg (56%) of the corresponding sulfoxide. Deprotection of the sulfoxide with hydrazine according to the general procedure of Example 39 afforded the title compound (10 mg, 76%) after prep-plate chromatography eluting with 1% $CH_3OH/CHCl_3$. $^1$H NMR ($CDCl_3$) $\delta$2.24, (d, 6H), 3.65 (s, 3H), 4.16 (d, 1H), 4.39 (d, 1H), 6.49 (s, 1H), 7.44 (m, 1H), 7.99 (m, 2H), 8.72 (d, 1H).

BIOLOGICAL EVALUATION

The compounds of this invention exhibited gastric antisecretory activity in canines, as indicated by inhibition in vitro of ($H^+/K^+$)-ATPase obtained from canine gastric mucosa and by inhibition in vivo of gastric acid secretion in dogs. The antisecretory activity of the compounds of this invention illustrated in the Examples was determined by the following methods.

Inhibition of ($H^+/K^+$)-ATPase from Canine Gastric Mucosa

Mongrel dogs weighing 15 to 25 kilograms were fasted for twenty-four hours, with water provided ad libitum. The animals were anesthetized with pentobarbital and the stomachs were removed. Subsequent tissue manipulations and subcellular fractionations were performed at 0° C. to 4° C. After the stomachs were cut open and rinsed with tap water, the antral and cardiac regions were removed and the remaining tissue was rinsed three times in saline. The glandular mucosa was removed mechanically, chopped finely in a medium containing 10 mM Tris hydrochloride (pH 7.4) and 250 mM sucrose, and homogenized. The homogenate was centrifuged at 20,000×g for twenty minutes and the pellet discarded. The supernatant was then centrifuged at 150,000×g for ninety minutes and the supernatant discarded. The pellet was resuspended in the Tris-HCl/sucrose medium by homogenization. Part (2 ml) of the resultant microsomal suspension was layered onto a step gradient consisting of 9 ml of 15% sucrose above 12 ml of 30% sucrose, each sucrose solution being buffered with 10 mM Tris hydrochloride (pH 7.4) containing 0.01% sodium azide. The microsomes retained at the 15%–30% sucrose interface, after centrifugation at 250,000×g for sixty minutes, were used as the source of $(H^+/K^+)$-ATPase. Microsomal preparations were lyophilized, a process that assured potassium ion permeability, and stored at −10° C. until used.

$(H^+/K^+)$-ATPase activity for each test compound was determined, in duplicate, by measuring the release of inorganic phosphate, which was assayed according to the method of J. ChandraRajan and L. Klein, *Anal. Biochem.*, 72, 407 (1976). The $(H^+/K^+)$-ATPase assay medium consisted of 20 mM Mes-Tris (pH 6.0), 5 mM magnesium chloride, 25 mM sucrose, and 4 mM Tris-ATP with or without 20 mM potassium chloride in a total volume of 2 ml. Microsomal suspensions (20 to 60 mcl, containing about 25 μg protein) were added to the assay medium, without Tris-ATP, and then preincubated with a test compound for thirty minutes at 37° C. The assay was initiated by adding Tris-ATP and the mixture was incubated another thirty minutes at 37° C. A 200-mcl aliquot of the assay mixture was then added to 1.4 ml of a solution consisting of 0.1 M sodium acetate (pH 4.0) and 10% sodium dodecylsulfate, followed by the addition of 200 mcl each of 1% ammonium molybdate and 1% ascorbic acid. At least fifteen minutes later, the optical absorbance at 870 nM (which was proportional to inorganic phosphate concentration up to 100 nmoles per tube, as determined by a standard curve) was obtained. Enzyme activity was linear with incubation time.

$(H^+/K^+)$-ATPase activity is represented by the difference between the measured activities in the presence of potassium ion ($K^+$-stimulated) and in the absence of potassium ion (basal). The concentration of a test compound required to inhibit 50% of the $(H^+/K^+)$-ATPase activity (i.e., the $IC_{50}$) was determined at least in duplicate using linear regression analysis of results obtained for three different compound concentrations ranging from 0.1 μM to 0.2 mM. If the $IC_{50}$ for a test compound could not be determined for the concentration range tested, percent inhibition of $(H^+/K^+)$-ATPase was obtained for the compound at 0.1 mM.

Inhibition of Gastric Acid Secretion in Gastric Fistula Beagle Dogs

Adult female beagle dogs weighing 6 to 11 kilograms obtained from Laboratory Research Enterprises (Kalamazoo, Mich.) or from Hazelton Research Animals (Cumberland, Va.) were surgically implanted with a simple Thomas-type gastric cannula. After recovery from surgery, the dogs were trained to stand quietly, fully conscious, in Pavlov-type dog restraining slings and were acclimated to intravenous infusion of histamine dihydrochloride. During the course of these studies, no dog was used more than once a week. All dogs were deprived of food, but not water, for 18 hours prior to each assay. Each dog was initially infused with 0.15 M sodium chloride solution at a constant rate of 6.5 mg/hr. The volume of gastric secretions, collected in plastic bottles affixed to the cannula, were measured to the nearest 0.1 ml at 30 minute intervals. One of the following protocols was followed, depending on the route chosen for administration of test compound.

Intravenous Dosing

Following a 30-minute basal secretion period, test compounds were administered intravenously (i.v.). At the end of an additional 30 minute period, the saline infusion was replaced with histamine dihydrochloride in saline administered at a rate 15 mcg per kilogram of body weight per hour. Histamine stimulation was maintained for a maximum of four hours during which time gastric secretions were collected every 30 minutes. The pH and titratable acidity were determined for samples from each collection period.

Intragastric Dosing

Following a 30-minute basal secretion period, the collection bottles were removed, dosing plugs were inserted, and test compounds were administered intragastrically (i.g.). At the end of a 30-minute drug absorption period, the stomachs were emptied, the collection bottles were reattached, and collections were resumed at 30-minute intervals. Simultaneously, the saline infusion was replaced with a continuous intravenous infusion of histamine dihydrochloride in saline administered for four hours at a rate 15 mcg per kilogram of body weight per hour.

Intraduodenal Dosing

Dogs were also equipped with duodenal cannulas for intraduodenal (i.d.) administration of test compounds. Dosing was otherwise performed as described for intragastric dosing.

Data from each protocol were analyzed for three gastric sample variables: volume of gastric juice, acid concentration, and total acid output. Percent inhibition for each four-hour experimental period was determined for each parameter by comparison with 3 to 4 controls in which only food was given.

Estimates of $ED_{50}$'s were determined from dose response curves.

Inhibition of Gastric Acid Secretion in Meal-Stimulated Pavlov Pouch Dog

Adult female beagle dogs weighing 6 to 10 kilograms were obtained from Laboratory Research Enterprises (Kalamazoo, Mich.) or from Hazelton Research Animals (Cumberland, Va.). Surgical implantation of a Thomas-type gastric cannula into an innervated Pavlov pouch of each dog was performed by the method reported by L. Burrows et al., *J. Surgical Res.*, 4, 147 (1964). After recovery from surgery, the dogs were trained to stand quietly, fully conscious, in Pavlov-type dog restraining slings. All dogs were deprived of food, but not water, for 24 hours prior to each assay. Basal acid secretion was measured by collecting from the cannulas for 30 minutes before dosing with a test compound. Solutions of the test compounds in iso-osmotic phosphate buffer (pH 7.4) were given either intravenously or directly into the Pavlov pouch. After 30 minutes the pouch was drained. The dogs were then fed 320 grams of dog food and gastric acid secretions were collected each half hour for four hours. Controls were determined in the same way except that only food (i.e., no test compound) was administered.

Data were analyzed for three different variables: volume of gastric juice, acid concentration, and total acid output.

Percent inhibition for the four-hour experimental period was determined for each parameter by comparison with 3 to 4 controls. Estimates of $ED_{50}$ were determined from dose response curves. Results are shown in Table 1.

TABLE 1

Pharmacological Test Results

| Example | $(H^+/K^+)$-ATPase IC50 ($\mu$M) | Gastric-Fistula % Inhibition (3 mg/kg dose) | Pavlov-Pouch % Inhibition (dose (mg/kg)) |
|---|---|---|---|
| 3 | 4.3 | 59 i.v. | 87 (10 mg/kg) |
|   |     | 53 i.d. | 20 (1 mg/kg) |
| 4 | 0.7 | 14 i.v. | 8 (3 mg/kg) |
| 6 | >100 | 37 i.v. | |
| 8 | 7.4 | 60 i.v. | |
| 10 | 13.5 | 44 i.v. | |
| 12 | 11.0 | 90 i.d. | 54 (10 mg/kg) |
|    |      |         | 19 (3 mg/kg) |
| 16 | 130.0 | 24 i.v. | |
| 18 | 24.0 | 13 i.v. | |
| 20 | 1.6 | 37 i.v. | 22 (3 mg/kg) |
| 22 | 9.3 | 70 i.v. | |
| 24 | 0.6 | 73 i.v. | |
| 26 | 2.1 | 67 i.v. | |
| 28 | 3.2 | 93 i.v. | 43 (3 mg/kg) |
|    |     | 44 i.d. | |
| 30 | 0.8 | | |
| 32 | 0.6 | 21 i.d. | |
| 34 | 4.2 | 91 i.v. | 79 (3 mg/kg) |
|    |     | 66 i.d. | |
|    |     | 43 i.g. | |
| 36 | 5.4 | 96 i.v. | |
|    |     | 72 i.d. | |
| 37 | 2.0 | 62 i.d. | |
| 38 | 3.9 | 21 i.d. | |
| 39 | 0.2 | 53 i.d. | |
| 41 | 7.9 | | |
| 43 | 12.0 | | |
| 45 | 24.0 | | |
| 47 | 4.4 | 37 i.d. | |
| 49 | >100 | 16 i.d. | |
| 51 | 2.6 | 19 i.d. | |
| 53 | 0.6 | 79 i.d. | |
| 55 | 0.8 | | |
| 57 | 60.0 | | |
| 59 | 2.7 | | |
| 61 | 5.3 | | |
| 63 | 0.71 | | |
| 65 | 1.5 | | |
| 67 | 8.5 | | |
| 69 | 153.0 | 28 i.d. | |
| 71 | >100 | 7 i.d. | |
| 73 | >100 | | |
| 75 | 120.0 | | |
| 76 | 24.9 | | |
| 77 | 16.0 | | |
| 78 | 2.1 | 31 i.d. | |
| 81 | 100 | 41 i.v. | |
| 83 | 8.6 | 15 i.v. | |
| 85 | 2.5 | 59 i.v. | |
| 87 | 2.2 | | |
| 89 | 1.68 | | |
| 91 | 4.5 | 46 i.v. | |
| 93 | 6.9 | | |
| 95 | 6.95 | | |
| 97 | 3.1 | | |
| 99 | 23.7 | | |
| 101 | 0.7 | | |
| 103 | 1.8 | | |
| 105 | 9.5 | | |
| 107 | 9.1 | | |
| 109 | 20.0 | 58 i.d. | |
| 111 | 34.8 | | |
| omeprazole | 1.9 | | |

Enzymatic Assay for HCMV Protease (Assemblin) Inhibitors

The compounds of this invention exhibited antiviral activity as indicated by inhibition in vitro of herpesvirus protease and by inhibition in vivo of herpesvirus infectivity. The antiviral activity of the compounds of this invention illustrated in the Examples was determined by the following methods.

The enzymatic assay for assemblin protease inhibitors compared the rate of product appearance between a control reaction containing no inhibitor and one that contained a known concentration of a potential inhibitor. There were two phases to the enzyme reaction. The first was a period of incubation of enzyme in the presence of inhibitor, but in the absence of the substrate. This incubation allowed for the inhibitor to bind and potentially block the enzyme from hydrolyzing the substrate. The second phase was started by adding the substrate and measuring the rate of product production.

Assay Components

Recombinant HCMV Protease

HCMV protease was purified from E. coli expressing a DNA construction encoding the protease domain of the $U_L80$ open reading frame of human cytomegalovirus strain AD169. The construction also encoded six additional histidine residues at the amino terminus of the protease. These additional histidine residues provided an affinity ligand by which it was purified using nickel-nitriloacetic acid-agarose (Qiagen).

The purified protease was stored as a 1–3 mg/ml stock solution in 50 mM sodium phosphate buffer, pH 7.4; 300 mM sodium chloride; 100 mM imidazole; 50% (v/v) glycerol. This stock was diluted with assay buffer to 4.8 $\mu$g/ml. A 100 $\mu$L aliquot of this solution was used in the enzyme reaction.

A specific substrate was synthesized based on the cleavage specificity of HCMV protease at the "maturation site" of the assembly protein (F. Liu and B. Roizman, J. Virol., 65, 5149 (1991), and A. R. Welch, et al, J. Virol., 65, 4091 (1991)). The assembly protein maturation site has the sequence ... AGVVNA*SCRLATA ...; the substrate used was dabcyl-Abu-GVVNASARLA-EDANS (DE2). Upon excitation at 360 nM the EDANS chromophore emitted light (fluoresces) at 490 nM that was absorbed by the dabcyl chromophore ($E_{max}$=460 nM). However, when the two chromophores are separated because of hydrolysis of the peptide moiety by HCMV protease the EDANS fluorescence was no longer quenched and an increase in fluorescence was realized. DE2 was stored as a stock solution at 160 $\mu$g/ml in dimethyl sulfoxide. This was diluted 10-fold with assay buffer to give a concentration of 16 $\mu$g/ml just before use. An aliquot of 50 $\mu$L was used in the reaction.

An assay Buffer (10 mM sodium phosphate buffer, pH 7.4; 150 mM sodium acetate; 0.1% CHAPS; and 20% (v/v) glycerol) was used to dilute stock solutions of enzyme and substrate.

Inhibitors were dissolved in dimethyl sulfoxide at 16-times the final assay concentration. A 10 $\mu$L aliquot of this inhibitor solution was used in the reaction.

A 100 $\mu$L aliquot of enzyme solution (4.8 $\mu$g/ml) was mixed with 10 $\mu$L of inhibitor solution in a 96-well plate cell and incubated at 22° C. for 30 minutes. Control reactions contained 10 $\mu$L of dimethylsulfoxide instead of inhibitor solution. After the preincubation was completed, 50 $\mu$L of substrate solution was added and the fluorescence recorded every 5 minutes for a period of 30 minutes. All reactions were run in triplicate with the exception of the uninhibited control reaction which was replicated 6-fold. The change in fluorescence was recorded over time and an average rate for each set of 3 reactions was calculated. Fluorescence assays were subject to spurious variations due to factors such as dust in the 96-well plate; such results were omitted from the calculation of relative rates.

ANTIVIRAL ASSAYS

These complementary assays tested the ability of a compound to inhibit the production of new virus and the toxicity of the compound to the host cells. It was important that both assays be performed simultaneously in order to compare the results directly since toxicity may indirectly reduce viral yield.

Abbreviations

DMEM—Dulbecco's Modified Eagle Medium; commercially available.

FBS—fetal bovine serum; commercially available and contains unknown factors necessary for growth of cells in culture.

PBS—phosphate buffered saline: 10 mM sodium phosphate buffer, pH 7.4, 120 mM sodium chloride, 2.7 mM potassium chloride.

Enzyme Linked ImmunoSorbant Assay (ELISA) for HCMV Antigens

Viral yield was estimated by measuring the amount of a viral antigen produced 4 days post infection with a monoclonal antibody to an abundant "immediate early" viral protein. An enzyme-linked (horseradish peroxidase) secondary antibody specific to the primary (mouse) antibody was used to measure the amount of viral antigen. Test compounds were diluted to 2-times the desired final concentration in DMEM+5% FBS. One hundred microliters of this solution was placed in each well of a 96-well plate. This was performed once for the antiviral 96-well plate and again for a cytotoxicity plate. Two controls were also included for both plates; a no drug control and a ganciclovir control. Ganciclovir was included because it has known antiviral activity for HCMV. All cells were prepared by harvesting human foreskin fibroblasts, MRHF, with trypsin and re-suspending at a concentration of $5 \times 10^5$ cells/ml in DMEM. Infected cells were prepared by infecting these with HCMV (strain AD169) at a multiplicity of infection=0.2. One hundred microliters of uninfected cells ($5 \times 10^4$ cells) were added to the appropriate wells of the cytotoxicity plate. In a similar manner 100 µl of infected cells ($5 \times 10^4$ cells) were added to the appropriate wells of the antiviral plate. Additionally, uninfected cells not treated with test compound were included as controls on the antiviral plate. Plates were incubated for 96 hours at 37° C. in 5% $CO_2$ atmosphere and processed to measure the amount of viral antigen and toxicity.

The following was performed on the antiviral plate only. Media was removed and cells were fixed with 1:1 acetone:methanol for 15 minutes at −20° C. Fixative was removed and cells were washed once with PBS containing 0.05% Tween20. In order to block nonspecific binding of antibodies each well was incubated with PBS containing 3% (w/v) bovine serum albumin (BSA) for 1 hour at 22° C. The blocking solution was removed and the cells were washed once with PBS containing 0.05% Tween20 before incubating with 1:100 dilution of primary antibody in PBS containing 3% BSA for 2 hours at 22° C. The primary antibody was a monoclonal antibody (mouse source) specific to the immediate early nuclear antigen of HCMV and was commercially available (Dupont). The 1° antibody solution was removed and the plate was rinsed 5 times with PBS containing 1% (v/v) Triton X-100 (PBST) before incubating with secondary antibody diluted 1:1000 in PBS containing 3% BSA for 2 hours at 22° C. The secondary antibody (goat source) recognized the murine-specific determinants of the 1° antibody and was covalently linked to horseradish peroxidase (Sigma). The plate was rinsed 5 times with PBST and once with deionized water before adding 100 µl TMB substrate solution and incubating 30 minutes at 22° C. The reaction was stopped by adding 100 µL of phosphoric acid and the OD at 450 nm recorded. TMB (3,3',5,5' tetramethylbenzidine) was the substrate for the horseradish peroxidase linked to the 2° antibody (Kirkegaard & Perry Laboratories, Inc.). Antiviral activity was calculated by comparing the amount of viral antigen produced in drug treated wells with that produced in wells absent of drug. Results are included in Table 2.

Recombinant Human Cytomegalovirus Antiviral Assay

In this assay, HCMV replication was monitored by the production of $E.\ coli$ β-galactosidase by the engineered virus RC256 [Spaete and Mocarski, Proc.Nat.Acad.Sci., 84, 7213–7217 (1987)]. One antiviral assay and one cytotoxicity assay were done for each compound. Dilutions of test compounds and infection of cells in a 96-well plate was essentially as described above for the HCMV ELISA except for the following. Human foreskin fibroblasts at $3.5 \times 10^5$ cells per milliliter were infected in solution with RC256 at 0.05 pfu per cell. Compounds and cells were incubated 3 days and processed at 2 days post infection. For the β-galactosidase detection, the supernatant was aspirated from the antiviral assay plates and 50 µl Reporter Lysis Buffer (Promega, diluted to 1× with water) was added per well. The plates were incubated at room temperature at least 30 minutes and plates were frozen at −20° C. at this point for later processing. 50 µl of 2× assay buffer [120 mM $Na_2HPO_4$, 80 mM $NaH_2PO_4$, 2 mM $MgCl_2$, 100 mM 2-mercaptoethanol, 4.4 mM ONPG (Sigma)] was added per well and incubated at room temperature 30 to 45 minutes. The reaction was stopped with 100 µl 1M CAPS buffer, pH=11.0, per well and the optical density was read at 410 nm. Ganciclovir was used as a positive control and the $EC_{50}$ was determined as described above for the HCMV ELISA. Results are included in Table 2.

HSV-1 Crystal Violet Antiviral Assay

Compounds were screened for antiviral activity by their ability to prevent viral cytopathic effect as monitored by crystal violet staining [Alder et al., Antiviral Res., 23, 93–105 (1994)]. Plate set up and serial dilution of compounds was as described above for the HCMV antiviral ELISA. Two assays were performed per compound, an antiviral assay and an assay to measure cytotoxicity of the compounds. Vero cells (ATCC) were trypsinized and resuspended at a concentration of $3.5 \times 10^5$ cells per ml in MEM/ 5% FBS (Life Technologies) and infected with HSV-1 (strain KOS, from P. Olivo, Washington University, St. Louis, Mo.) at an MOI=0.05 pfu per cell. Infected cells or uninfected cells (100 µl) were added per well as described above. The plates were incubated 3 days and processed at 2 days post infection. The supernatant was aspirated and the plates were stained with crystal violet as described above for the human foreskin fibroblast cytotoxicity assay. The $EC_{50}$ and $TC_{50}$ were determined as described above. Acyclovir (Sigma, catalog number S4669) was used as a positive control.

Engineered Cell Line Assay for Assessment of Antiviral Activity Against Herpes Simplex Virus Construction of Cell Line HSV-1 (strain 17) DNA in plasmid pMON27010 was used as a substrate for polymerase chain reaction amplification of the putative $U_L26.5$ promoter region [Liu and Roizman, *J. Virol.*, 65, 206–212 (1991)]. pMON27010 has the HSV-1 3.4 kbp Kpn I fragment that includes the $U_L26$ open reading frame in pUC19. Oligonucleotide primers (5' GTACGAATTCCGCCCTTTCGCCACCTGTCGCC-3') and (5' GTACGGATCCAACGGGGTTCAGGGGGGGC-AGT-3') were used to amplify a 435 bp fragment that begins 401 bases upstream (5') to the capsid assembly protein initiator methionine codon and ends 11 bases 3' to the adenosine of the methionine initiation codon. Oligonucleotides were synthesized by Genosys Biotechnologies, Inc. (Woodlands, Tex.). The adenosine of the ATG initiator codon in the amplified product was mutated by the downstream oligonucleotide to a guanosine to prevent translation start from the natural capsid assembly protein initiator codon. The amplified HSV DNA was flanked by an Eco RI site on the 5' end and a Bam HI site on the 3' end. Amplification was according to recommended conditions using the GeneAmp kit (Perkin-Elmer-Cetus, Norwalk, Conn.) with the addition of dimethyl sulfoxide to 5% of the total reaction volume and a Perkin-Elmer-Cetus DNA thermocycler. The amplification reaction steps were as follows: One cycle of 94° C.: 1.5 minutes; 62° C.: 2 minutes; 72° C.: 2 minutes followed by 30 cycles of 94° C.: 45 seconds; 62° C.: 45 seconds; 72 ° C.: 1 minute followed by 1 cycle as the previous cycle except the last 72° C. step was for 5 minutes. Standard molecular biology techniques were according to Sambrook, Fritsch and Maniatis (eds.), Molecular Cloning: A Laboratory Manual, Second Edition, Cold Spring Harbor Press, Cold Spring Harbor, N.Y. 1989. The amplified fragment was subcloned into pCRII (Invitrogen, San Diego, Calif.) using the manufacturer's protocol. The resulting plasmid was designated pMON15837a. pMON15837a and pMON3327 which contains the SV40 polyadenylation signal in pUC18 [Highkin et al., *Poultry Science*, 70, 970–981 (1990)] were digested with Eco RI and Bam HI. The fragments were gel purified using Qiaex resin (Qiagen, Chatsworth, Calif.). The HSV containing sequence from pMON15837a was ligated into pMON3327 to generate pMON15841. Bacterial β-galactosidase and firefly luciferase [DeWet et al., *Mol. Cell. Biol.*, 7, 725–737 (1987] coding regions were isolated as Bam HI fragments and ligated into Bam HI-digested, shrimp alkaline phosphatase treated (US Biochemical Corp, Cleveland, Ohio) pMON15841 to generate pMON15842 and pMON15843 which have the respective coding regions in the orientation necessary for expression from the $U_L26.5$ promoter.

BHK-21 cells (ATCC) were transfected with 10 μg of pMON15842 or pMON15843 and 1 μg of pSV2neo [Southern and Berg, *J. Mol. and Appl. Genet.*, 1, 327–341 (1982)] using LipofectAmine Reagent (Life Technologies) and recommended procedures. After 48 hours, cells were split into media (DMEM/10% FBS/2 mM extra glutamine/penicillin and streptomycin) containing 400 μg/ml G418 (Life Technologies). Surviving colonies were isolated, expanded and infected with HSV-1 (strain F,(ATCC) or strain 17, from R. N. Lausch, University of South Alabama) or HSV-2 (strain MS, ATCC) to test for stimulation of luciferase or β-galactosidase activity as follows. Cells were seeded into a 6-well dish. The following day, the cell density was scored on a scale of 1 to 4 with 4 being the most dense. All wells were infected with $1 \times 10^6$ plaque forming units (pfu) of HSV 1 or HSV-2 in 1.0 ml for 1.5 hours. Two milliliters of media was added and cells were harvested the following day. The media was aspirated and the cells were lysed in 250 μl of 1× Reporter Lysis Buffer (Promega) at room temperature for 15 to 30 minutes. The lysate was scraped into a Eppendorf tube and the debris was pelleted by centrifugation for 2 minutes in a microfuge. Cells transfected with the β-galactosidase containing plasmids were assayed for activity by adding 50 μl of lysate to 50 μl of 2× substrate buffer (see RC256 assay above) which contains ONPG. After 10 minutes at 37° C., the reaction was stopped with 150 μl 1 M sodium carbonate. The optical density was read at 410 nm. Cells transfected with the luciferase containing plasmids were assayed for luciferase activity by adding 5 μl of extract to a white 96-well plate (Dynatech). 70 μl of luciferase substrate (Promega) was injected automatically by the luminometer (Dynatech) and the light burst was recorded. Cell lines displaying the most activity per relative density were further characterized. Two cell lines (BHK 42-21 for β-galactosidase and BHK 43-4 for luciferase) were the most sensitive cell lines upon stimulation by HSV-1 or HSV-2 infection.

Antiviral Assay using Engineered Cell Lines

The compound to be tested was diluted and plated in a 96-well plate (Falcon) as above. BHK 42-21 cells were mixed with HSV 1(strain 17) or HSV-2 (strain MS, ATCC) at a multiplicity of infection of 0.002 to 0.004 pfu/cell. $5 \times 10^4$ cells (with virus or without virus for controls) were added per well and incubated at 37° C. for 48 hours in 7.5% $CO_2$. The media was aspirated and the cells were lysed in 50 μl of 1× Reporter Lysis buffer (Promega) for 15 minutes at room temperature. 20 μl of the lysate was added to 20 μl of 2× β-galactosidase substrate (Promega) in a 96-well dish for 10 minutes at room temperature then stopped with 60 μl 1 M sodium carbonate. The optical density at 410 nm was determined using a plate reader. The optical density was plotted as a function of drug concentration using a semilog plot. The $EC_{50}$ (concentration drug necessary to decrease the optical density and, therefore, virus replication by 50%) was estimated from the dose-response curve. Acyclovir was used as a standard. Conditions were essentially the same for BHK 43-4 except $1 \times 10^4$ cells per well are used and 5 μl of cell lysate is assayed using 70 μl of luciferase substrate. The dose-response to acyclovir using HSV-2 (strain MS, ATCC) was nearly the same as with HSV-1 except the responsiveness in terms of maximum optical density or relative light units was lower. Results are included in Table 2.

TABLE 2

| COMPOUND | Assemblin % Inhibition at 100 μm | HCMV cell $EC_{50}$ (μm) | RC256 $EC_{50}$ (μm) | HSV2 $EC_{50}$ (μm) |
|---|---|---|---|---|
| omeprazole | 0 | 57 | 90 | >100 |
| 3a | 20 | 16 | 65 | >100 |
| 10 | 43 | | | |
| 12 | 26 | | | |
| 20 | 60 | | | |
| 22 | 35 | | | |
| 32 | 52 | | | |
| 39 | 46 | | | |
| 41 | 67 | 59 | | |
| 43 | 74 | 23 | | |
| 45 | 51 | | | |
| 47 | 40 | | | |
| 53 | 85 | 13 | | |
| 55 | | 13 | 22 | |
| 57 | 66 | | | |
| 59 | 71 | | | |
| 63 | 86 | 13 | 18 | |
| 71 | 44 | | | |

TABLE 2-continued

| COMPOUND | Assemblin % Inhibition at 100 μm | HCMV cell EC$_{50}$ (μm) | RC256 EC$_{50}$ (μm) | HSV2 EC$_{50}$ (μm) |
|---|---|---|---|---|
| 73 | 50 | | | |
| 78 | 82 | 61 | 18 | 28 |
| 83 | 88 | | | |
| 112 | 18 | | | |
| 113 | 95 | | | |
| 114 | 67 | | | |
| 115 | 79 | | | |
| 116 | 59 | | | |
| 119 | 91 | | | |
| 120 | 88 | | | |

Regardless of the route of administration selected, the compounds of the present invention are formulated into pharmaceutically acceptable dosage forms by conventional methods known to those skilled in the art. The compounds may be formulated using pharmacologically acceptable acid addition or base addition salts. Moreover, the compounds or their salts may be used in a suitable hydrated form.

The compounds according to the invention may be administered to the subject concerned in conventional manner. In general, the compounds may be administered by a topical, oral, rectal or parenteral (e.g. intravenous, subcutaneous or intramuscular) route. The dosage of the compound will depend on the condition being treated, the particular antiviral compound employed, and other clinical factors such as the weight and condition of the patient and the routes of administration of the compounds. The compounds can be administered in such oral dosage forms as tablets, capsules, pills, powders, or granules. They may also be administered intravascularly, intraperitoneally, subcutaneously, or intramuscularly, using forms known to the pharmaceutical art. An effective but non-toxic quantity of the compound is employed in treatment. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention may be in the range of about 1.0 mg/kg to 500 mg/kg, preferably in the range of about 10 to 100 mg/kg orally or about 1.0 to 20 mg/kg intravenously.

For infections of the eye or other external tissues, e.g., mouth and skin, the formulations are preferably applied as a topical ointment or cream containing the active ingredient (s) in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiviral active ingredients are preferably present in such formulations in a concentration of 0.5 to 20%, advantageously 0.5 to 10% and particularly about 1.5% w/w.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like. Sweetening and flavoring agents and preservatives can also be included where appropriate.

Although this invention has been described with respect to specific embodiments, the details of these embodiments are not to be construed as limitations.

What is claimed is:

1. A method of treating DNA viral infection in a subject, said method comprising treating said subject with an effective amount of a compound of Formula I $$R^2-(CR^3R^4)_p-S(O)_m-(CR^5R^6)_n-R^1 \qquad I$$

wherein $R^1$ is selected from $C_1$–$C_{10}$ alkoxy, $C_1$–$C_{10}$ alkoxycarbonyl, $C_1$–$C_{20}$ dialkylamino, aryl, substituted aryl, heteroaryl and substituted heteroaryl, wherein the substituted aryl and substituted heteroaryl radicals are substituted with one or more radicals selected from $C_1$–$C_{10}$-alkoxy, amino-$C_1$–$C_{10}$-alkoxy, amino-$C_1$–$C_{10}$-alkoxy substituted on the nitrogen atom with $C_1$–$C_{20}$ alkyl, $C_3$–$C_{10}$-cycloalkyl, and aryl-$C_1$–$C_{20}$-alkyl, hydroxyl, cyano, nitro, $C_1$–$C_{20}$-alkyl, halo, $C_1$–$C_{20}$-haloalkyl, $C_1$–$C_{20}$-haloalkoxy, $C_1$–$C_{20}$-alkanoyl, $C_3$–$C_{10}$-cycloalkyl-$C_1$–$C_{10}$-alkoxy, carboxyl, acyl, aminocarbonyl, $C_1$–$C_{20}$-alkylaminocarbonyl, aryl-$C_1$–$C_{10}$-alkoxy, $C_2$–$C_{10}$-alkenyloxy, $C_2$–$C_{10}$-alkynyloxy, aminosulfonyl, $C_1$–$C_{20}$-alkylaminosulfonyl, $C_1$–$C_{20}$-alkylsulfonylamino, heterocyclo, aryl-$C_1$–$C_{20}$-alkyl, heteroaryl-$C_1$–$C_{20}$-alkyl, $C_1$–$C_{10}$-alkoxycarbonyl, heteroaryl, $C_1$–$C_{20}$-alkylthio, $C_1$–$C_{20}$-alkylsulfinyl, $C_1$–$C_{20}$-alkylsulfonyl, $C_2$–$C_{20}$-alkenylthio, arylthio, aryl-$C_1$–$C_{20}$-alkylthio, $C_3$–$C_{10}$-cycloalkylthio, amino and amino substituted with a radical selected from $C_1$–$C_{20}$-alkyl, aryl-$C_1$–$C_{20}$-alkyl, aryl, $C_2$–$C_{20}$-alkenyl, $C_2$–$C_{20}$-alkynyl, $C_3$–$C_{10}$-cycloalkyl, $C_3$–$C_{10}$-cycloalkenyl, $C_1$–$C_{20}$-hydroxyalkyl, $C_1$–$C_{20}$-alkylcarbonyl, $C_1$–$C_{10}$-alkoxycarbonyl, $C_1$–$C_{20}$alkoxyalkyl, arylcarbonyl and arylcarbonyl wherein the aryl ring is substituted with one or more radicals selected from $C_1$–$C_{20}$-alkyl, halo, $C_1$–$C_{10}$-alkoxy, aminocarbonyl and hydrazidylcarbonyl;

wherein $R^2$ is heteroaryl or heteroaryl substituted with one or more radicals selected from $C_1$–$C_{10}$-alkoxy, amino, cyano, nitro, hydroxyl, $C_1$–$C_{20}$-alkyl, $C_3$–$C_{10}$-cycloalkyl, halo, $C_1$–$C_{20}$-haloalkyl, $C_1$–$C_{10}$-haloalkoxy, carboxyl, $C_1$–$C_{20}$-alkanoyl, acyl, $C_1$–$C_{20}$-alkylamino, arylamino, aryl-$C_1$–$C_{20}$-alkylamino, $C_1$–$C_{20}$-alkanoylamino, $C_1$–$C_{20}$-alkylamino-$C_1$–$C_{20}$-alkyl, aminocarbonyl, aminocarbonyloxy, $C_1$–$C_{20}$-alkylaminocarbonyl, $C_1$–$C_{10}$-alkoxycarbonyl, aryloxycarbonyl, aryl-$C_1$–$C_{10}$-alkoxycarbonyl, $C_1$–$C_{20}$-alkylcarbonyl, $C_3$–$C_{10}$-cycloalkylcarbonyl, $C_1$–$C_{20}$-alkylcarbonyl-$C_1$–$C_{20}$-alkyl, $C_1$–$C_{10}$-alkoxycarbonyl-$C_1$–$C_{20}$-alkyl, $C_1$–$C_{20}$-alkylcarbonylamino, aryloxy, aryl-$C_1$–$C_{10}$-alkoxy, $C_2$–$C_{20}$-alkenyloxy, $C_2$–$C_{20}$-alkynyloxy, acyloxy, $C_3$–$C_{10}$-cycloalkyl-$C_1$–$C_{10}$-alkoxy, aryl-$C_1$–$C_{20}$-alkyl, aryl, aroyl, $C_1$–$C_{20}$-alkoxyalkyl, $C_1$–$C_{20}$-hydroxyalkyl, heterocyclo, heteroaryl-$C_1$–$C_{20}$-alkyl, $C_1$–$C_{20}$-alkylthio, $C_1$–$C_{20}$-alkylsulfinyl, $C_1$–$C_{20}$-alkylsulfonyl, arylthio, arylsulfinyl, aminosulfonyl, $C_1$–$C_{20}$-alkylsulfonylamino, and $C_1$–$C_{20}$-alkylaminosulfonyl;

wherein each of $R^3$, $R^4$, $R^5$ and $R^6$ is independently selected from hydrido, $C_1$–$C_{20}$-alkyl, aryl and aryl-$C_1$–$C_{20}$-alkyl; or wherein $R^3$ and $R^4$, or $R^5$ and $R^6$ together form $C_3$–$C_{10}$-cycloalkyl; and wherein each of m, n and p is a number independently selected from 0, 1 and 2;

provided that when $R^1$ is phenyl, $R^2$ is not pyridyl or 1-(β-D-ribofuranosyl)benzimidazole when m is 0 or 2;

or a pharmaceutically acceptable salt thereof.

2. Method according to claim 1, wherein $R^1$ is selected from $C_1$–$C_6$-alkoxy, $C_1$–$C_6$-alkoxycarbonyl, $C_1$–$C_{10}$-dialkylamino, aryl selected from phenyl and naphthyl, substituted aryl selected from phenyl and naphthyl, substituted heteroaryl selected from thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidinyl, thienopyridinyl, dihydrothienopyridinyl, carbostyryl, pyrimidyl and pyrazinyl, and heteroaryl selected from thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidinyl, thienopyridinyl, dihydrothienopyridinyl, carbostyryl, pyrimidyl and pyrazinyl, wherein the substituted aryl and substituted heteroaryl radicals are substituted with one or more radicals selected from $C_1$–$C_6$-alkoxy, $C_1$–C6-aminoalkoxy optionally substituted on the nitrogen atom with $C_1$–$C_{10}$-alkyl, $C_3$–$C_6$-cycloalkyl and aryl-$C_1$–$C_{10}$-alkyl, cyano, nitro, hydroxyl, $C_1$–$C_{10}$-alkyl, halo, $C_1$–$C_{10}$-haloalkyl, $C_1$–$C_6$-haloalkoxy, $C_3$–$C_6$-cycloalkyl-$C_1$–$C_6$-alkoxy, carboxyl, acyl, $C_1$–$C_{10}$-alkanoyl, aminocarbonyl, $C_1$–$C_{10}$-alkylaminocarbonyl, aryl-$C_1$–$C_6$-alkoxy, $C_2$–$C_{10}$-alkenyloxy, $C_2$–$C_{10}$-alkynyloxy, aminosulfonyl, $C_1$–$C_{10}$-alkylsulfonylamino, $C_1$–$C_{10}$-alkylaminosulfonyl, 5 to 20 membered heterocyclo, aryl-$C_1$–$C_{10}$-alkyl, heteroaryl-$C_1$–$C_{10}$-alkyl, $C_1$–$C_6$-alkoxycarbonyl, 5 to 8 membered heteroaryl, $C_1$–$C_{10}$-alkylthio, $C_1$–$C_{10}$-alkylsulfinyl, $C_1$–$C_{10}$-alkylsulfonyl, $C_2$–$C_{10}$-alkenylthio, $C_6$–$C_{10}$-arylthio, aryl-$C_1$–$C_{10}$-alkylthio, $C_3$–$C_6$-cycloalkylthio, amino and amino substituted with a radical selected from $C_1$–$C_{10}$-alkyl, aryl-$C_1$–$C_{10}$-alkyl, phenyl, $C_2$–$C_{10}$-alkenyl, $C_2$–$C_{10}$-alkynyl, $C_3$–$C_6$-cycloalkyl, acyl, $C_3$–$C_6$-cycloalkenyl, $C_1$–$C_{10}$-hydroxyalkyl, $C_1$–$C_{10}$-alkylcarbonyl, $C_1$–$C_6$-alkoxycarbonyl, $C_1$–$C_{10}$-alkoxyalkyl, phenylcarbonyl and phenylcarbonyl wherein the phenyl ring is substituted with one oromore radicals selected from $C_1$–$C_{10}$-alkyl, halo, $C_1$–$C_6$-alkoxy, aminocarbonyl and hydrazidylcarbonyl; wherein $R^2$ is selected from nitrogen-containing heteroaryl and nitrogen-containing heteroaryl substituted with one or more radicals selected from $C_1$–$C_6$-alkoxy, amino, cyano, nitro, hydroxyl, $C_1$–$C_{10}$-alkyl, $C_3$–$C_6$-cycloalkyl, halo, $C_1$–$C_{10}$-haloalkyl, $C_1$–$C_6$-haloalkoxy, carboxyl, $C_1$–$C_{10}$-alkanoyl, acyl, $C_1$–$C_{10}$-alkylamino, lower arylamino, $C_1$–$C_{10}$-alkylarylamino, $C_1$–$C_{10}$-alkanoylamino, $C_1$–$C_{10}$-alkylamino-$C_1$–$C_{10}$-alkyl, aminocarbonyl, $C_1$–$C_{10}$-alkylaminocarbonyl, $C_1$–C6-alkoxycarbonyl, lower aryloxycarbonyl, aryl-$C_1$–$C_6$-alkoxycarbonyl, $C_1$–$C_{10}$-alkylcarbonyl, $C_3$–$C_6$-cycloalkylcarbonyl, $C_1$–$C_{10}$- alkylcarbonyl-$C_1$–$C_{10}$-alkyl, $C_1$–$C_6$-alkoxycarbonyl-$C_1$–$C_{10}$-alkyl, $C_1$–$C_{10}$-alkylcarbonylamino, aminocarbonyloxy, phenyloxy, aryl-$C_1$–$C_6$-alkoxy, $C_2$–$C_{10}$-alkenyloxy, $C_2$–$C_{10}$-alkynyloxy, acyloxy, $C_3$–$C_6$-cycloalkyl-$C_1$–$C_6$-alkoxy, aryl-$C_1$–$C_{10}$-alkyl, phenyl, lower aroyl, $C_1$–$C_6$-alkoxyalkyl, $C_1$–$C_{10}$-hydroxyalkyl, 5 to 20 membered heterocyclo, heteroaryl-$C_1$–$C_{10}$-alkyl, $C_1$–$C_{10}$-alkylthio, $C_1$–$C_{10}$-alkylsulfinyl, $C_1$–$C_{10}$-alkylsulfonyl, lower arylthio, lower arylsulfinyl, lower arylsulfonyl, $C_1$–$C_{10}$-alkylsulfonylamino, aminosulfonyl and $C_1$–$C_{10}$-alkylaminosulfonyl; and wherein each of $R^3$, $R^4$, $R^5$ and $R^6$ is independently selected from hydrido, $C_1$–$C_{10}$-alkyl, phenyl, naphthyl and aryl-$C_1$–$C_{10}$-alkyl; or wherein $R^3$ and $R^4$, or $R^5$ and $R^6$ together form $C_3$–$C_6$-cycloalkyl; or a pharmaceutically acceptable salt thereof.

3. Method according to claim 2 wherein $R^1$ is a unsubstituted or substituted radical selected from phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidinyl, thienopyridinyl, dihydrothienopyridinyl, carbostyryl, pyrimidyl and pyrazinyl, wherein the substituted radicals in $R^1$ are substituted with one or more radicals selected from methoxy, ethoxy, propoxy, butoxy, isopropoxy, tert-butoxy, aminoethoxy, aminoethoxy substituted on the nitrogen atom with methyl, ethyl, propyl, butyl, pentyl, isopropyl, isobutyl, tert-butyl, cyclohexyl, cyclopropyl and benzyl, hydroxyl, amino, amino substituted with a radical selected from methyl, ethyl, propyl, butyl, pentyl, isopropyl, isobutyl, tert-butyl, benzyl, phenethyl, phenyl, butene, pentene, isopropylene, isobutylene, propargyl, cyclopropyl, cyclobutyl, cyclopentyl, cyclohexyl, formyl, acetyl, cyclobutenyl, cyclopentenyl, cyclohexenyl, hydroxymethyl, methylcarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methoxymethyl, phenylcarbonyl and phenylcarbonyl wherein the phenyl ring is substituted with one or more radicals selected from methyl, chloro, methoxy, aminocarbonyl and hydrazidylcarbonyl, cyano, nitro, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, cyclohexylmethoxy, carboxyl, formyl, acetyl, propionyl, aminocarbonyl, methylaminocarbonyl, dimethylaminocarbonyl, benzyloxy, aminosulfonyl, dimethylaminosulfonyl, methylsulfonylamino, morpholinyl, pyrrolidinyl, phthalimidyl, piperazinyl, piperidyl, benzyl, methoxycarbonyl, ethoxycarbonyl, pyridyl, methylthio, methylsulfinyl, methylsulfonyl, phenylthio, benzylthio, and cyclohexylthio; wherein $R^2$ is a unsubstituted or substituted radical selected from pyridyl, indolyl, imidazolyl, benzimidazolyl, napthoimidazolyl, 1,3-dioxolobenximidazolyl, imidazopyridyl, imidazoquinolinyl, dihydroimidazoquinolinyl, cycloheptoimidazolyl, cyclooxaundecanobenzimidazolyl, benzoxazolyl, benzothiazolyl, indolyl, thienoimidazolyl, pyridopyrazinyl, quinolinyl, quinoxalinyl, quinazolinyl, quinazolinonyl, triazolyl, tetrazolyl, oxazolyl, purinyl, indenoimidazolyl, thiadiazolyl, thiazolylpyridyl, pyridyl, pyrimidinyl, pyranobenzimidazolyl, thiopyranbenzimidazolyl, indolbenzimidazole, tetrahydroimidazoquinolinyl, wherein $R^2$ is substituted with one or more radicals selected from methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, cyclohexyl, cyclopropyl, cyclobutyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, trifluoroethoxy, carboxyl, formyl, acetyl, propionyl, butyryl, N-methylamino, N-ethylamino, N-propylamino, N-butylamino, N-tert-butylamino, N-pentylamino, N-hexylamino, N,N-dimethylamino, phenylamino, N-methyl-N-phenylamino, methylaminomethyl, aminocarbonyl, N-methylaminocarbonyl, N,N-dimethylaminocarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, phenoxycarbonyl, benzyloxycarbonyl, methylcarbonyl, cyclohexylcarbonyl, methylcarbonylmethyl, methoxycarbonylmethyl, methylcarbonylamino, aminocarbonyloxy, phenoxy, benzoxy, benzyl, phenethyl, phenyl, benzoyl, methoxymethyl, hydroxymethyl, morpholinyl, pyrrolidinyl, piperazinyl, piperidyl, methylthio, ethylthio, methylsulfinyl, ethylsulfinyl, methylsulfonyl, phenylthio, phenylsulfinyl, phenylsulfonyl, aminosulfonyl, methylsulfonylamino, methylaminosulfonyl and N,N-dimethylaminosulfonyl; wherein each of $R^3$, $R^4$, $R^5$ and $R^6$ is independently selected from hydrido, methyl, ethyl, propyl, butyl, pentyl, isopropyl, isobutyl, tert-butyl, phenyl and benzyl; or wherein $R^3$ and $R^4$, or $R^5$ and $R^6$ together form cyclopropyl, cyclobutyl or cyclopentyl; wherein m and n are 1; and wherein p is 0; or a pharmaceutically acceptable salt thereof.

4. Method of claim 3 selected from the group consisting of compounds, and their pharmaceutically acceptable salts, of the group selected from:

2-[(4,6-dimethyl-5-methoxy-2-phthalimidylphenyl) methylsulfonyl]-5-methoxy-1H-benzimidazole;

2-[[(5-chloro-1H-benzimidazol-2-yl)sulfinyl]methyl]-3,5-dimethyl-4-methoxybenzenamine;

(+)-2-[[(5-methoxy-1H-benzimidazol-2-yl)sulfinyl] methyl]-3,5-dimethyl-4-methoxybenzenamine;

(−)-2-[[(5-methoxy-1H-benzimidazol-2-yl)sulfinyl] methyl]-3,5-dimethyl-4-methoxybenzenamine;

N-[2-[[(6-methoxy-1H-benzimidazol-2-yl)sulfinyl] methyl]-3,5-dimethyl-4-methoxyphenyl]acetamide;

2-[(4,6-dimethyl-5-methoxy-2-phthalimidylphenyl) methylsulfinyl]-6-chloro-1-isopropyl-1H-benzimidazole;

2-[(4,6-dimethyl-5-methoxy-2-phthalimidylphenyl) methylsulfinyl]-5-chloro-1-isopropyl-1H-benzimidazole;

2-[[(1-methyl-1H-imidazol-2-yl)sulfinyl]methyl]-3,5-dimethyl-4-methoxybenzenamine;

2-[[(1H-imidazol-2-yl)sulfinyl]methyl]-3,5-dimethyl-4-methoxybenzenamine;

2-[(4,6-dimethyl-5-methoxy-2-phthalimidylphenyl) methylsulfinyl]-5-chloro-1-ethyl-1H-benzimidazole;

2-[(4,6-dimethyl-5-methoxy-2-phthalimidylphenyl) methylsulfinyl]-6-chloro-1-ethyl-1H-benzimidazole;

2-[[[2-[[(6-chloro-1-ethyl-1H-benzimidazol-2-yl) sulfinyl]methyl]-3,5-dimethyl-4-methoxyphenyl] amino]carbonyl]benzenecarboxylic acid hydrazide;

2-[[[2-[[(5-chloro-1-ethyl-1H-benzimidazol-2-yl) sulfinyl]methyl]-3,5-dimethyl-4-methoxyphenyl] amino]carbonyl]benzenecarboxylic acid hydrazide;

3-[[(1H-benzimidazol-2-yl)sulfinyl]methyl]-benzenamine;

4-methoxy-3,5-dimethyl-2-[(2-pyridinyl)sulfinylmethyl] benzenamine;

[2-[(2-N-isobutyl-N-methylamino)-benzyl]sulfinyl]-1H-benzimidazole;

2-[[3-methylpyridin-2-ylmethyl]sulfinyl]-1H-benzimidazole;

2-[(imidazo[1,2-a]pyridin-3-yl)methylsulfinyl]-1H-benzimidazole;

2-[(imidazo[1,2-a]pyridin-3-yl)methylsulfinyl]-1H-benzimidazole;

2-[(imidazo[1,2-a]pyridin-3-yl)methylsulfinyl]-5-methyl-1H-benzimidazole;

2-[(imidazo[1,2-a]pyridin-3-yl)methylsulfinyl]-5-methoxy-1H-benzimidazole;

5-chloro-2-[(imidazo[1,2-a]pyridin-3-yl-methyl)sulfinyl]-1H-benzimidazole;

2-[(imidazo[1,2-a]pyridin-3-yl)methylsulfinyl]-5-trifluoromethyl-1H-benzimidazole;

2-[(imidazo[1,2-a]pyridin-8-yl)methylsulfinyl]-1H-benzimidazole;

2-[(imidazo[1,2-a]pyridin-8-yl)methylsulfinyl]-1H-benzimidazole;

2-[(imidazo[1,2-a]pyridin-8-yl)methylsulfinyl]-5-methoxy-1H-benzimidazole;

5-ethoxy-2-[(imidazo[1,2-a]pyridin-8-yl-methyl)sulfinyl]-1H-benzimidazole;

2-[(imidazo[1,2-a]pyridin-8-yl)methylsulfinyl]-4-methyl-1H-benzimidazole;

2-[(imidazo[1,2-a]pyridin-8-yl)methylsulfinyl]-5-methyl-1H-benzimidazole;

2-[(imidazo[1,2-a]pyridin-8-yl)methylsulfinyl]-5,6-dimethyl-1H-benzimidazole;

2-[(imidazo[1,2-a]pyridin-8-yl)methylsulfinyl]-5,6-dimethoxy-1H-benzimidazole;

5-chloro-2-[(imidazo[1,2-a]pyridin-8-yl-methyl)sulfinyl]-1H-benzimidazole;

2-[(imidazo[1,2-a]pyridin-8-yl)methylsulfinyl]-5-trifluoromethyl-1H-benzimidazole;

2-[[(2,3-dimethylimidazo[1,2-a]pyridin-8-yl)methyl]sulfinyl]-1H-benzimidazole;

2-[[(3-methylimidazo[1,2-a]pyridin-8-yl)methyl]sulfinyl]-1H-benzimidazole;

2-[[(2-phenylimidazo[1,2-a]pyridin-8-yl)methyl]sulfinyl]-1H-benzimidazole;

2-[[(3-phenylimidazo[1,2-a]pyridin-8-yl)methyl]sulfinyl]-1H-benzimidazole;

2-[[(3-(4-nitrophenyl)imidazo[1,2-a]pyridin-8-yl)methyl]sulfinyl]-1H-benzimidazole;

2-[[[3-[3-(trifluoromethyl)phenyl]imidazo[1,2-a]pyridin-8-yl]methyl]sulfinyl]-1H-benzimidazole;

5-methyl-2-[[[3-[3-(trifluoromethyl)phenyl]imidazo[1,2-a]pyridin-8-yl]methyl]sulfinyl]-1H-benzimidazole;

5-chloro-2-[[[3-[3-(trifluoromethyl)phenyl]imidazo[1,2-a]pyridin-8-yl]methyl]sulfinyl]-1H-benzimidazole;

2-[[[3-[4-(trifluoromethyl)phenyl]imidazo[1,2-a]pyridin-8-yl]methyl]sulfinyl]-1H-benzimidazole;

5-chloro-2-[[[3-[4-(trifluoromethyl)phenyl]imidazo[1,2-a]pyridin-8-yl]methyl]sulfinyl]-1H-benzimidazole;

4-[8-[((1H-benzimidazol-2-yl)sulfinyl)methyl]imidazo[1,2-a]pyridin-3-yl]benzoate;

2-[[[3-(4-chlorophenyl)imidazo[1,2-a]pyridin-8-yl]methyl]sulfinyl]-1H-benzimidazole;

2-[[[3-(4-methylphenyl)imidazo[1,2-a]pyridin-8-yl]methyl]sulfinyl]-1H-benzimidazole;

2-[(imidazo[1,2-a]pyridin-5-yl)methylsulfinyl]-1H-benzimidazole;

2-((n-butoxycarbonylmethyl)sulfinyl)thiazolo(5,4-b)pyridine;

5-chloro-2-((2-ethoxyethyl)sulfinyl)benzothiazole;

4,6-dimethyl-2-(((imidazo(1,2-a)pyridin-2-yl)methyl)thio)-1H-benzimidazole;

2-[3-methyl-4-(2-(N-benzyl-N-cyclohexylamino)-ethoxy)pyridyl]methylthio-1H-benzimidazole;

ethyl 2-[(1H-benzimidazol-2-yl)thiomethyl]-4-methyl-amino-5-pyrimidine carboxylate;

9-(benzimidazol-2-yl)sulfinyl-4-methoxy-2,3-cycloheptenopyridine;

2-(5-fluoro-2-(4-methoxy-2-pyridyl)-phenylsulfinyl)-1H-benzimidazole;

5-difluoromethoxy-2-(((3,4-dimethoxy-2-pyridinyl)methyl)sulfinyl)-1H-benzimidazole;

2-(((4-difluoromethoxy-3-methyl-2-pyridyl)methylsulfinyl)benzimidazole;

2-[4(3-methoxypropoxy)-3-methylpyridine-2-yl]methylsulfinyl-1H-imidazole;

2-((6-azachroman-5-yl)methylsulfinyl)-benzimidazole;

5-carbomethoxy-6-methyl-2-(((3,4-dimethoxy-2-pyridinyl)-methyl)sulfinyl-1H-benzimidazole;

5-carbomethoxy-6-methyl-2-(((3,4-dimethoxy-2-pyridinyl)-methyl)sulfinyl)-1H-benzimidazol-1-yl-methylethylcarbonate;

2-((3-methyl-4-(2,2,2-trifluoroethoxy)-2-pyridyl)methylsulfinyl)benzimidazole;

4-fluoro-2-(((4-methoxy-2-pyridinyl)methyl)sulfinyl-1H-benzimidazol-1-yl-methyl-ethylcarbonate;

2-[3-methyl-4-(1-benzyl-4-piperidyl)oxy-2-pyridyl]methylthio-1H-benzimidazole;

2-(3-methyl-4-(2-(N-methyl-N-(4-methyl-benzyl)amino)ethoxy)-2-pyridyl)methylsulfonyl-1H-benzimidazole;

2-(4-methoxy-6-methyl-2-pyrimidinyl)methylthio-1H-benzimidazole;

2-[2-[N-4-(3-fluorophenyl)-butyl-N-methyl]aminoethyl]thio-(1H)-benzimidazole;

5-chloro-2-(3,4-dimethoxy-2-pyridylmethylsulfinyl)-1H-benzimidazole;

5-fluoro-2-(4-cyclopropylmethoxy-2-pyridylmethyl-sulfinyl)-1H-benzimidazole;

4-fluoro-2-(4-methoxy-2-pyridylmethylsulfinyl)-1H-benzimidazole;

2-(((4-methoxy-3,5-dimethyl-2-pyridinyl)-methyl)-sulfinyl)-5-methoxy-1H-benzimidazole;

5-hydroxymethyl-2-((3,5-dimethyl-4-methoxy-2-pyridyl)methylthio-1H-benzimidazole;

2-(4-ethylthio-3-methylpyridin-2-yl-methyl)sulfinyl-benzimidazole;

2-(((4-(2-benzyloxyethoxy)-3-methyl-2-pyridyl) methylthio)benzimidazole;
2-[[2-[N-(2-hydroxyethyl)-N-methylamino]-5-methoxy] benzylsulfinyl]benzimidazole;
2-[2-(3,5-dimethyl-4-ethoxy)pyridylmethylsulfinyl]-5-methoxy-imidazo(4,5-b)pyridine;
2-(5-benzyl-4-chloro-6-methyl-2-pyrimidinyl) methylthio-1H-benzimidazole;
2,2-difluoro-6-((5-benzyloxy-4-methoxy-2-pyridyl) methylthio)-5H-(1,3)-dioxolo(4,5-f)benzimidazole;
5-carboethoxy-6-methyl-2-(((3-methyl-2-pyridyl)methyl) sulfinyl)-1H-benzimidazole;
5-(2-benzimidazolylsulfinylmethyl)-3,4-dihydro-4-methyl-2H-1,4-benzoxazine;
2-(3-methyl-4-(2-(N-benzyl-N-methylamino)ethoxy-2-pyridyl)methylsulfinyl-1H-benzimidazole;
2-(3-methyl-4-(2-(1,2,3,4-tetrahydroisoquinolin-2-yl)-ethoxy)-2-pyridyl)methylsulfinyl-1H-benzimidazole;
2-[1-(3,5-dimethylpyrazolyl)]methylthiobenzimidazole;
2-(3-chloro-4-methoxy-2-picolylthio)-5-methoxy-1H-benzimidazole;
2-(4-(2-ethoxyethoxy)-3-methyl-2-pyridyl) methylsulfinyl-1H-benzimidazole;
2-(3-methylthieno(2,3-c)pyridin-7-yl)methylsulfinyl)-benzimidazole;
2-(2-dimethylamino-5-methoxybenzylsulfinyl)-5-methoxy-benzimidazole;
2-(2-dimethylamino-5-methylbenzylsulfinyl)-5-methoxybenzimidazole;
2-[4-(2,3,5-trimethyl)pyridylthio]-5-methoxybenzimidazole;
2[(2-(4-chlorophenyl)-5-methylimidazol-4-yl) methylthio]-\benzimidazole;
2-(5-hydroxy-1H-benzimidazol-2-ylsulfinylmethyl)-N,N-dimethylbenzenamine;
2-((6-methoxyisoquinolin-1-yl)methylsulfinyl) benzimidazole;
3-(5-methoxy-1H-benzimidazol-2-yl) thiomethylcarbostyril;
5-methoxy-2-(4-dimethylamino-S-fluoro-2-pyridylmethylsulfinyl)-1H-benzimidazole;
2-(2-dimethylaminobenzyl-sulfinyl)-5-cyclopropylmethoxy)benzimidazole;
2-(3,5-dimethyl-2-pyridylmethylsulfinyl)-5-cyclopropylmethoxy-benzimidazole;
2-[2-(N-cyclohexyl-N-methylamino)benzylsulfonyl] benzimidazole;
8-(5-fluoro-6-methoxy-2-benzimidazolyl)sulfinylmethyl-1-ethyl-4-(N-methyl-N-allyl)amino-1,2,3,4-tetrahydroquinoline;
2-(2-benzyloxycarbonylaminobenzylthio)benzimidazole;
2-(2-benzimidazolylmethylthio)pyrimidine;
2-(2-dimethylaminobenzylsulfinyl)imidazo[4,5-b]-pyridine;
2-(2-pyridylmethylsulfinyl)quinoxaline;
2-methyl-3-(2-pyridylmethylsulfinyl)pyrido[2,3-b] pyrazine;
5-acetyl-2-((2-dimethylaminobenzyl)sulfinyl) benzimidazole;
2-((3,5-dimethyl-4-methoxy-2-pyridyl)methylsulfinyl)-5-fluoro-1H-benzimidazole;
2-(3-pyridylmethylthio)-5-methoxybenzimidazole;
2-(2-methylaminobenzylsulfinyl)benzimidazole;
5-methoxy-2-(2-dimethylaminobenzylsulfinyl)-1H-benzimidazole;
2-(3,4-dimethoxypyrid-2-ylmethylsulfinyl)-5-trifluoromethyl-benzimidazole;
5-methoxy-2-(4-piperidino-2-pyrimidinylmethylsulfinyl)-(1H)-benzimidazole;
2-[2-(4-benzyloxy)-pyridylmethylsulfinyl] benzimidazole;
4-allyloxy-8-(2-benzimidazolyl)thio-3-methyl-5,6,7,8-tetrahydroquinoline;
2-[2-(4-methoxy-5-n-pentyl)-pyridylmethylthio] benzimidazole;
2-(5-bromo-4-piperidino-2-pyridylmethylsulfinyl)-5-methoxy-(1H)-benzimidazole;
2-((3,5-dimethyl-4-morpholinopyrid-2-yl) methylsulfinyl)benzimidazole;
2-((2-pyridinylmethyl)sulfinyl)-1H-benzimidazole-1-methanol;
2-((3,4-dihydro-2H-thieno(3,2-c)pyridinylmethyl)thio)-1H-benzimidazole-1-methanol;
2-(4-isopropoxy-2-pyridyl)methylsulfinylbenzimidazole;
2-((4-fluorobenzyloxy-3-methyl-2-pyridyl) methylsulfinyl)benzimidazole;
2-(2-aminobenzylsulfinyl)-benzimidazole;
N,N-dimethyl-2-(1H-benzimidazol-2-yl-sulfinylmethyl) benzenamine;
2-[(4,5-dimethoxy-2-pyridyl)methylsulfinyl]-5-trifluoromethoxy-1H-benzimidazole;
2,2-difluoro-6-[(4,5-dimethoxy-2-pyridyl)methylthio]-5H-1,3-dioxolo-(4,5-f)benzimidazole;
2-((4-morpholinyl-3-ethylpyridin-2-yl)methylsulfinyl)-5-trifluoromethylbenzimidazole;
2-((4-methoxy-2-pyridyl)methylsulfinyl)-5-trifluoromethoxy-1H-benzimidazole;
5-cyclopropylcarbonyl-2-((4-methoxy-2-pyridyl) methylsulfinyl)-1H-benzimidazole;
2-[2-(3,5-dimethyl-4-methoxy)-pyridylmethylsulfinyl]-(5-chloro)-benzimidazole;
2-[2-(4,5-dimethyl)-pyridylmethylsulfinyl]-(5-acetyl-6-methyl)-benzimidazole;
1-(p-chlorobenzoyl) -2-(β-morpholinylmethyl-sulfinyl) benzimidazole;
2,3-dihydro-2-(2-pyridyl)thiazolo[3,2-a]benzimidazole-1-oxide;
2-[(2-pyridylmethyl)thio]-1H-naphth[2,3-d]imidazole;
1,5,6,7-tetrahydro-2-(5-methyl-2-pyridyl-methyl)-thio) indeno(5,6-d)imidazole;
4-methyl-2-(5-methyl-2-pyridyl-methylthio)-1H-naphtho (2,3-d)imidazole ;
2,2-difluoro-6-(4-methoxy-2-pyridylmethylsulfinyl)-5H-1,3-dioxolo[4,5-f]benzimidazole;
2-benzylthio-(4H)-imidazo(4,5,1-ij)quinoline;
2-(2-chlorophenylmethylthio)-5,6-dihydro-(4H)-imidazo (4,5,1-ij)quinoline;
5,6-dihydro-2-(2-pyridylmethylthio)-4H-imidazo(4,5,1-ij)quinoline;
5,6-dihydro-2-(2-(3,5-dimethylpyridyl)methylsulfinyl)-4H-imidazo;
5,7-dihydro-2-(((4-methoxy-3-methyl-2-pyridyl)methyl) sulfinyl)-5,5,7,7-tetramethylindeno(5,6-d)imidazol-6 (1H)-one;

2-(2-pyridylmethylthio)-6-isopropyl-cycloheptoimidazole;
2-[2-(3,5-dimethyl)pyridylmethylsulfinyl]5-fluoro-benzoxazole;
3-[(4-dimethylamino-2-pyridyl)methylthio]indole;
5-methyl-2-(2-pyridylmethylthio-3H-thieno(2,3-d)imidazole;
2-(2-(3,5-dimethyl-4-methoxy)pyridylmethylsulfinyl)-7-imidazo(4,5-b)pyridine;
2-(2-pyridylmethylsulfinyl)quinoxaline;
2-[(2-pyridyl)methylsulfinyl]thieno[3,4-d]-imidazole;
2-(((3,5-dimethyl-4-methoxy-2-pyridyl)methyl)thio)-4,5-diphenyloxazole;
3,5-dimethyl-4-methoxy-6-(((5-phenyl-1,2,4-triazol-3-yl)-thio)methyl)pyridine;
2-(((3,5-dimethyl-4-methoxy-2-pyridyl)methyl)sulfinyl)-4,5-diphenylimidazole;
5-(((4,5-diphenyl-2-oxazolyl)sulfinyl)methyl)-2,2-dimethyl-8-methyl-4H-1,3-dioxino(4,5-c)pyridine;
5-(((3,5-dimethyl-4-methoxy-2-pyridyl)methyl)sulfinyl)-1-methyltetrazole;
6-benzoylamino-7-chloro-2-(((3,5-dimethyl-4-methoxy-2-pyridyl)-methyl)thio)benzothiazole;
2-[[(3,5-dimethyl-4-methoxy-2-pyridyl)-methyl]thio]quinoline;
2-[2-(3,5-dimethyl)pyridylmethylsulfinyl]-5-methoxy-imidazo[4,5-b]pyridine;
5-(4,5-dihydro-2-oxazolyl)-2-((3,5-dimethyl-4-methoxy-2-pyridyl)methylthio)-1H-benzimidazole;
2-(2-dimethylaminobenzylsulfinyl)-5-methoxyimidazo[4,5-b]-pyridine;
3-phenyl-2-(2-pyridylmethylsulfinyl)-4(3H)-quinazolinone;
4-amino-2-(2-pyridylmethylthio)quinazoline;
2-(4-morpholinyl-2-pyrimidinylmethylthio)thieno(3,4-d)imidazole;
8-[2'-(N,N-dimethylanily)methylthio]purine;
2-[2'-(N,N-dimethylanily)methylthio]thieno-(3,4-d)-imidazole;
2-(4-methoxy-2-picolinylthio)-1H-thieno[3,4-d]imidazole;
2-(2-pyridylmethyl)thio-8H-indeno(1,2-d)imidazole;
2-(4-methoxy-5-chloro-2-picolythio)-1H-thieno(3,4-d)imidazole;
2-[2-(1-pyrrolidinyl)benzylthio]cycloheptoimidazole;
2-(2-acetylaminophenyl)methylthiocycloheptoimidazole;
2-amino-5-(2-(2-pyridyl)ethylthio)-1,3,4-thiadiazole;
2-gernaylthio-benzimidazole;
2-(2-chlorobenzylthio)-8,8-dimethyl-6-oxo-5,6,7,8-tetrahydro-3H-imidazo[4,5-g]quinoline;
8-(2-pyrimidinyl-sulfinyl)quinoline;
2-((3-methyl-2-pyridyl)methylsulfinyl)pyrano(2,3-f)benzimidazole;
2-[(2-isobutylamino)benzylsufinyl]imidazole;
ethyl 2-((1H-benzimidazol-2-yl)-sulfinylmethyl)-4-dimethylamino-5-pyrimidinecarboxylate;
2-((2-ethoxyethyl)sulfinyl)-4-(3-pyridyl)thiazole;
2-[2-(2-propynylamino)benzylsulfinyl]imidazole;
2-(2-(2-methoxyethylamino)benzylsulfinyl)imidazole;
1-(2-pyridyl)-2-(3-dimethylamino)benzylsulfinyl)imidazole;
2-(2-methylaminobenzylthio)-4,5,6,7-tetrahydro-1H-benzimidazole;
4,5-diphenyl-2-(2-pyridylmethyl)-thioimidazole;
4-phenyl-2-(2-pyridylmethyl)thioimidazole;
4,5-bis(4-methoxyphenyl)-2-(2-thienylthio)imidazole;
2-(3-chloro-2-pyridinylthiomethyl)-4,5-dihydro-1H-imidazole;
1-methyl-2-(2-pyrimidinylthiomethyl)-5-nitro-imidazole;
1-methyl-2-(2-pyridylsulfonylmethyl)-5-nitroimidazole;
1-methyl-2-(5-bromo-2-pyridylthiomethyl)-5-nitro-imidazole;
2-[(1H-benzimidazol-2-yl)sulfinylmethyl]benzenamine;
2-[(1H-benzimidazol-2-yl)sulfinylmethyl]N,N-dimethylbenzenamine;
N-[2-[(1H-benzimidazol-2-yl)sulfinylmethyl]phenyl]acetamide;
2-[[(4-methyl-1H-benzimidazol-2-yl)sulfinyl]methyl]benzenamine;
2-[[(5,6-dimethyl-1H-benzimidazol-2-yl)sulfinyl]methyl]benzenamine;
2-[[(5-methoxy-1H-benzimidazol-2-yl)sulfinyl]methyl]benzenamine;
methyl 2-[[(2-aminophenyl)methyl]sulfinyl]-5-methoxy-1Hbenzimidazole-6-carboxylate;
2-[(1H-benzimidazol-2-yl)sulfinylmethyl]-4-chlorobenzenamine;
2-[(1H-benzimidazol-2-yl)sulfinylmethyl]-5-chlorobenzenamine;
2-[(1H-benzimidazol-2-yl)sulfinylmethyl]-4-methoxybenzenamine;
2-[(1H-benzimidazol-2-yl)sulfinylmethyl]-6-methoxybenzenamine;
2-[(1H-benzimidazol-2-yl)sulfinylmethyl]-3-methylbenzenamine;
2-[(1H-benzimidazol-2-yl)sulfinylmethyl]-4-methylbenzenamine;
2-[(1H-benzimidazol-2-yl)sulfinylmethyl]-6-methylbenzenamine;
2-[(1H-benzimidazol-2-yl)sulfinylmethyl]-4,6-dimethylbenzenamine;
2-[(1H-benzimidazol-2-yl)sulfinylmethyl]-N-methylbenzenamine;
2-[[(5-methoxy-1H-benzimidazol-2-yl)sulfinyl]methyl]-4-methylbenzenamine;
2-[[(5-methoxy-1H-benzimidazol-2-yl)sulfinyl]methyl]-6-methylbenzenamine;
2-[(1H-benzimidazol-2-yl)sulfinylmethyl]-4-ethylbenzenamine;
2-[(1H-benzimidazol-2-yl)sulfinylmethyl]-6-ethylbenzenamine;
2-[(1H-benzimidazol-2-yl)sulfinylmethyl]-4-methoxy-3,5-dimethylbenzenamine;
2-[[(5-methyl-1H-benzimidazol-2-yl)sulfinyl]-methyl]benzenamine;
2-[[(5-chloro-1H-benzimidazol-2-yl)sulfinyl]-methyl]benzenamine;
2-[[(5-ethoxy-1H-benzimidazol-2-yl)sulfinyl]-methyl]benzenamine;
2-[[[(5-(trifluoromethyl)-1H-benzimidazol-2-yl]sulfinyl]methyl]benzenamine;
2-[(1H-benzimidazol-2-yl)sulfinylmethyl]-4-(trifluoromethyl)benzenamine;

2-[(1H-benzimidazol-2-yl)sulfinylmethyl]-4-butylbenzenamine;

2-[(1H-benzimidazol-2-yl)sulfinylmethyl]-5,6-dimethylbenzenamine;

2-[(1H-benzimidazol-2-yl)sulfinylmethyl]-3,6-dimethylbenzenamine;

2-[(1H-benzimidazol-2-yl)sulfinylmethyl]-4-chloro-6-methylbenzenamine;

2-[(1H-benzimidazol-2-ylsulfinylmethyl]-4-chloro-6-methoxy-3-methylbenzenamine;

2-[[(5-ethoxy-1H-benzimidazol-2-yl)sulfinyl]-methyl]-4-methylbenzenamine;

2-[[(5-methyl-1H-benzimidazol-2-yl)sulfinyl]-methyl]-5,6-dimethylbenzenamine;

2-[[[(5-(trifluoromethy)1-1H-benzimidazol-2-yl]sulfinyl]-3,6-dimethylbenzenamine;

2-([[[(5-(trifluoromethyl)1-1H-benzimidazol-2-yl]sulfinyl]methyl]-6-methoxybenzenamine;

methyl 2-amino-3-[(1H-benzimidazol-2-yl)sulfinyl)methyl]benzoate;

ethyl 4-amino-3-[(1H-benzimidazol-2-yl)sulfinyl)methyl]benzoate;

ethyl 4-amino-3-[[(5-methoxy-1H-benzimidazol-2-yl)sulfinyl]methyl]benzoate;

2-[[5,6-dimethoxy-1H-benzimidazol-2-yl)sulfinyl]methyl]-4-methylbenzenamine;

2-[(1H-benzimidazol-2-yl)sulfinylmethyl]-4-fluorobenzenamine;

2-[(1H-benzimidazol-2-yl)sulfinylmethyl]-3,4,5-trimethylbenzenamine;

2-[[(5-methoxy-1H-benzimidazol-2-yl)sulfinyl]methyl]-4-methoxy-3,5-dimethylbenzenamine;

3-[(1H-benzimidazol-2-yl)sulfinylmethyl]benzenamine;

3-[(1H-benzimidazol-2-yl)sulfinylmethyl]-2-pyridinamine;

3-[(1H-benzimidazol-2-yl)sulfinylmethyl]-N,N-dimethyl-2-pyridinamine;

6-[(1H-benzimidazol-2-yl)sulfinylmethyl]-2-pyridinamine;

6-[[(4-methyl-1H-benzimidazol-2-yl)-sulfinyl]methyl]-2-pyridinamine;

6-[[(5-methyl-1H-benzimidazol-2-yl)-sulfinyl]methyl]-2-pyridinamine;

6-[[(5-methoxy-1H-benzimidazol-2-yl)sulfinyl]-methyl]-2-pyridinamine;

6-[[(5-chloro-1H-benzimidazol-2-yl)-sulfinyl]methyl]-2-pyridinamine;

6-[[[5-(trifluoromethyl)-1H-benzimidazol-2-yl]sulfinyl]methyl]-2-pyridinamine;

6-[[(5-ethoxy-1H-benzimidazol-2-yl)-sulfinyl]methyl]-2-pyridinamine;

6-[[(5,6-dimethoxy-1H-benzimidazol-2-yl)-sulfinyl]methyl]-2-pyridinamine;

6-[[(5,6-dimethyl-1H-benzimidazol-2-yl)-sulfinyl]methyl]-2-pyridinamine;

6-[[(4,6-dimethyl-1H-benzimidazol-2-yl)-sulfinyl]methyl]-2-pyridinamine;

6-[[[5-(hydroxymethyl)-1H-benzimidazol-2-yl]sulfinyl]methyl]-2-pyridinamine;

6-[(1H-benzimidazol-2-yl)sulfinylmethyl]-N-(2,2-dimethylpropyl)-2-pyridinamine;

6-[(1H-benzimidazol-2-yl)sulfinylmethyl]-N-ethyl-2-pyridinamine; and

5-[(1H-benzimidazol-2-yl)sulfinylmethyl]-2-pyridinamine.

5. The method according to claim 1 wherein the subject is infected with a herpesvirus.

6. A method of treating viral infection in a subject, said method comprising treating said subject with an effective amount of a compound of Formula II

II wherein X is selected from CH or N;

wherein Y is selected from $CH_2$, $NR^8$, O and S;

wherein Z is selected from $-S(O)_m-$, $-(CR^3R^4)_pS(O)_m-$ and $-S(O)_m(CR^5R^6)_n-$;

wherein each of m, n and p is a number independently selected from 0, 1 and 2;

wherein $R^1$ is an unsubstituted or substituted radical selected from aryl and heteroaryl, wherein the substituted radical in $R^1$ is substituted with one or more radicals selected from $C_1$–$C_{10}$-alkoxy, amino-$C_1$–$C_{10}$-alkoxy, amino-$C_1$–$C_{10}$-alkoxy substituted on the nitrogen atom with $C_1$–$C_{20}$-alkyl, $C_3$–$C_{10}$-cycloalkyl and aryl-$C_1$–$C_{20}$-alkyl, cyano, nitro, hydroxyl, $C_1$–$C_{20}$-alkyl, halo, $C_1$–$C_{20}$-haloalkyl, $C_1$–$C_{10}$-haloalkoxy, $C_3$–$C_{10}$-cycloalkyl-$C_1$–$C_{10}$-alkoxy, carboxyl, acyl, $C_1$–$C_{20}$-alkanoyl, aminocarbonyl, $C_1$–$C_{20}$-alkylaminocarbonyl, aryl-$C_1$–$C_{10}$-alkoxy, $C_2$–$C_{20}$-alkenyloxy, $C_2$–$C_{20}$-alkynyloxy, aminosulfonyl, $C_1$–$C_{20}$-alkylaminosulfonyl, $C_1$–$C_{20}$-alkylsulfonylamino, heterocyclo, aryl-$C_1$–$C_{20}$-alkyl, heteroaryl-$C_1$–$C_{20}$-alkyl, $C_1$–$C_{10}$-alkoxycarbonyl, heteroaryl, $C_1$–$C_{20}$-alkylthio, $C_1$–$C_{20}$-alkylsulfinyl, $C_1$–$C_{20}$-alkylsulfonyl, $C_2$–$C_{20}$-alkenylthio, arylthio, aryl-$C_1$–$C_{20}$-alkylthio, $C_3$–$C_{10}$-cycloalkylthio, amino and amino substituted with a radical selected from $C_1$–$C_{20}$-alkyl, aryl-$C_1$–$C_{20}$-alkyl, aryl, $C_2$–$C_{20}$-alkenyl, $C_2$–$C_{20}$-alkynyl, $C_3$–$C_{10}$-cycloalkyl, acyl, $C_3$–$C_{10}$-cycloalkenyl, $C_1$–$C_{20}$-hydroxyalkyl, $C_1$–$C_{20}$-alkylcarbonyl, $C_1$–$C_{10}$-alkoxycarbonyl, $C_1$–$C_{20}$-alkoxyalkyl, arylcarbonyl and arylcarbonyl wherein the aryl ring is substituted with one or more radicals selected from $C_1$–$C_{20}$-alkyl, halo, $C_1$–$C_{10}$-alkoxy, aminocarbonyl and hydrazidylcarbonyl;

wherein each of $R^3$, $R^4$, $R^5$ and $R^6$ is independently selected from hydrido, $C_1$–$C_{20}$-alkyl, aryl and aryl-$C_1$–$C_{20}$-alkyl; or wherein $R^3$ and $R^4$, or $R^5$ and $R^6$ together form $C_3$–$C_{10}$-cycloalkyl;

wherein $R^7$ is one or more radicals selected from $C_1$–$C_{10}$-alkoxy, amino, cyano, nitro, hydroxyl, $C_1$–$C_{20}$-alkyl, $C_3$–$C_{10}$-cycloalkyl, halo, $C_1$–$C_{20}$-haloalkyl, $C_1$–$C_{10}$-haloalkoxy, carboxyl, $C_1$–$C_{20}$-alkanoyl, acyl, $C_1$–$C_{20}$-alkylamino, arylamino, $C_1$–$C_{20}$-alkylarylamino, $C_1$–$C_{20}$-alkanoylamino, $C_1$–$C_{20}$-alkylaminoalkyl, aminocarbonyl, $C_1$–$C_{20}$-alkylaminocarbonyl, $C_1$–$C_{10}$-alkoxycarbonyl, aryloxycarbonyl, aryl-$C_1$–$C_{10}$-alkoxycarbonyl, $C_1$–$C_{20}$-alkylcarbonyl, $C_3$–$C_{10}$-cycloalkylcarbonyl, $C_1$–$C_{20}$-alkylcarbonylalkyl, $C_1$–$C_{10}$-alkoxycarbonyl-$C_1$–$C_{20}$-alkyl, $C_1$–$C_{20}$-alkylcarbonylamino, aminocarbonyloxy, aryloxy, aryl-

91

$C_1$–$C_{10}$-alkoxy, $C_2$–$C_{20}$-alkenyloxy, $C_2$–$C_{20}$-alkynyloxy, acyloxy, $C_3$–$C_{10}$-cycloalkyl-$C_1$–$C_{10}$-alkoxy, aryl-$C_1$–$C_{20}$-alkyl, aryl, aroyl, $C_1$–$C_{20}$-alkoxyalkyl, $C_1$–$C_{20}$-hydroxyalkyl, heterocyclo, heteroaryl-$C_1$–$C_{20}$-alkyl, $C_1$–$C_{20}$-alkylthio, $C_1$–$C_{20}$-alkylsulfinyl, $C_1$–$C_{20}$-alkylsulfonyl, arylthio, arylsulfinyl, $C_1$–$C_{20}$-alkylsulfonylamino, aminosulfonyl and $C_1$–$C_{20}$-alkylaminosulfonyl; or wherein $R^5$ and $R^8$ taken together form a ring; and wherein $R^8$ is selected from hydrido, $C_1$–$C_{20}$-alkyl, $C_2$–$C_{20}$-alkenyl, $C_1$–$C_{20}$-hydroxyalkyl, acyl, $C_1$–$C_{20}$-alkoxyalkyl, $C_3$–$C_{10}$-cycloalkyl, aryl, aryloxy-$C_1$–$C_{10}$-alkyl, $C_1$–$C_{20}$-alkylthioalkyl, aryl-$C_1$–$C_{20}$-alkyl, $C_1$–$C_{10}$-alkoxycarbonyl, aminocarbonyl, $C_1$–$C_{20}$-alkanoyl, $C_1$–$C_{20}$-alkylaminocarbonyl and $C_1$–$C_{20}$-alkylsulfonyl; provided that when m is 0, $R^8$ is not 1-(β-D-ribofuranosyl)benzimidazole;

or a pharmaceutically acceptable salt thereof.

7. Method according to claim 6 wherein $R^1$ is an unsubstituted or substituted radical selected from phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidyl, thienopyridinyl, dihydrothienopyridinyl, carbostyryl, pyrimidyl and pyrazinyl, wherein the substituted radicals in $R^1$ is substituted with one or more radicals selected from $C_1$–$C_6$-alkoxy, $C_1$–$C_6$-aminoalkoxy, $C_1$–$C_6$-aminoalkoxy substituted on the nitrogen atom with $C_1$–$C_{10}$-alkyl, $C_3$–$C_6$-cycloalkyl and aryl-$C_1$–$C_{10}$-alkyl, cyano, nitro, hydroxyl, $C_1$–$C_{10}$-alkyl, halo, $C_1$–$C_{10}$-haloalkyl, $C_1$–$C_6$-haloalkoxy, $C_3$–$C_6$-cycloalkyl-$C_1$–$C_6$-alkoxy, carboxyl, acyl, $C_1$–$C_{10}$-alkanoyl, aminocarbonyl, $C_1$–$C_{10}$-alkylaminocarbonyl, aryl-$C_1$–$C_6$-alkoxy, $C_2$–$C_{10}$-alkenyloxy, $C_2$–$C_{10}$-alkynyloxy, aminosulfonyl, $C_1$–$C_{10}$-alkylaminosulfonyl, $C_1$–$C_{10}$-alkylsulfonylamino, 5 to 20 membered heterocyclo, aryl-$C_1$–$C_{10}$-alkyl, heteroaryl-$C_1$–$C_{10}$-alkyl, $C_1$–$C_6$-alkoxycarbonyl, 5 to 8 membered heteroaryl, $C_1$–$C_{10}$-alkylthio, $C_1$–$C_{10}$-alkylsulfinyl, $C_1$–$C_{10}$-alkylsulfonyl, $C_2$–$C_{10}$-alkenylthio, lower arylthio, aryl-$C_1$–$C_{10}$-alkylthio, $C_3$–$C_{10}$-cycloalkylthio, amino and amino substituted with a radical selected from $C_1$–$C_{10}$-alkyl, aryl-$C_1$–$C_{10}$-alkyl, phenyl, $C_2$–$C_{10}$-alkenyl, $C_2$–$C_{10}$-alkynyl, $C_3$–$C_6$-cycloalkyl, acyl, $C_3$–$C_6$-cycloalkenyl, $C_1$–$C_{10}$-hydroxyalkyl, $C_1$–$C_{10}$-alkylcarbonyl, $C_1$–$C_6$-alkoxycarbonyl, $C_1$–$C_{10}$-alkoxyalkyl, phenylcarbonyl and phenylcarbonyl wherein the phenyl ring is substituted with one or more radicals selected from $C_1$–$C_{10}$-alkyl, halo, $C_1$–$C_6$-alkoxy, aminocarbonyl and hydrazidylcarbonyl; wherein each of $R^3$, $R^4$, $R^5$ and $R^6$ is independently selected from hydrido, $C_1$–$C_{10}$-alkyl, phenyl, naphthyl and aryl-$C_1$–$C_{10}$-alkyl; or wherein $R^3$ and $R^4$, or $R^5$ and $R^6$ together form $C_3$–$C_6$-cycloalkyl; wherein $R^7$ is one or more radicals selected from $C_1$–$C_6$-alkoxy, amino, cyano, nitro, hydroxyl, $C_1$–$C_{10}$-alkyl, $C_3$–$C_6$-cycloalkyl, halo, $C_1$–$C_{10}$-haloalkyl, $C_1$–$C_6$-haloalkoxy, carboxyl, $C_1$–$C_{10}$-alkanoyl, acyl, $C_1$–$C_{10}$-alkylamino, lower arylamino, $C_1$–$C_{10}$-alkylarylamino, $C_1$–$C_{10}$-alkanoylamino, $C_1$–$C_{10}$-alkylaminoalkyl, aminocarbonyl, $C_1$–$C_{10}$-alkylaminocarbonyl, $C_1$–$C_6$-alkoxycarbonyl, lower aryloxycarbonyl, aryl-$C_1$–$C_6$-alkoxycarbonyl, $C_1$–$C_{10}$-alkylcarbonyl, $C_3$–$C_6$-cycloalkylcarbonyl, $C_1$–$C_{10}$-alkylcarbonylalkyl, $C_1$–$C_6$-alkoxycarbonyl-$C_1$–$C_{10}$-alkyl,

92

$C_1$–$C_{10}$-alkylaminocarbonyl, aminocarbonyloxy, phenoxy, aryl-$C_1$–$C_6$-alkoxy, $C_2$–$C_{10}$-alkenyloxy, $C_2$–$C_{10}$-alkynyloxy, acyloxy, $C_3$–$C_6$-cycloalkyl-$C_1$–$C_6$-alkoxy, aryl-$C_1$–$C_{10}$-alkyl, optionally substituted lower aryl, lower aroyl, $C_1$–$C_{10}$-alkoxyalkyl, $C_1$–$C_{10}$-hydroxyalkyl, 5 to 20 membered heterocyclo, heteroaryl-$C_1$–$C_{10}$-alkyl, $C_1$–$C_{10}$-alkylthio, $C_1$–$C_{10}$-alkylsulfinyl, $C_1$–$C_{10}$-alkylsulfonyl, lower arylthio, lower arylsulfinyl, lower arylsulfonyl, $C_1$–$C_{10}$-alkylsulfonylamino, aminosulfonyl and $C_1$–$C_{10}$-alkylaminosulfonyl; or wherein $R^5$ and $R^8$ taken together form a ring; and wherein $R^8$ is selected from hydrido, $C_1$–$C_{10}$-alkyl, $C_2$–$C_{10}$-alkenyl, $C_1$–$C_{10}$-hydroxyalkyl, acyl, $C_1$–$C_{10}$-alkoxyalkyl, phenyl, naphthyl, aryloxy-$C_1$–$C_{10}$-alkyl, $C_1$–$C_{10}$-alkylthioalkyl, aryl-$C_1$–$C_{10}$-alkyl, $C_1$–$C_6$-alkoxycarbonyl, aminocarbonyl, $C_1$–$C_{10}$-alkanoyl, $C_1$–$C_{10}$-alkylaminocarbonyl and $C_1$–$C_{10}$-alkylsulfonyl; or a pharmaceutically acceptable salt thereof.

8. Method of claim 7 wherein $R^1$ is unsubstituted or substituted with one or more radicals selected from methoxy, ethoxy, propoxy, butoxy, isopropoxy, tert-butoxy, aminoethoxy, aminoethoxy substituted on the nitrogen atom with methyl, ethyl, propyl, butyl, pentyl, isopropyl, isobutyl, tert-butyl, cyclohexyl, cyclopropyl and benzyl, amino, amino substituted with a radical selected from methyl, ethyl, propyl, butyl, pentyl, isopropyl, isobutyl, tert-butyl, benzyl, phenethyl, phenyl, butene, pentene, isopropylene, isobutylene, propargyl, cyclopropyl, cyclobutyl, cyclopentyl, cyclohexyl, formyl, acetyl, cyclobutenyl, cyclopentenyl, cyclohexenyl, hydroxymethyl, methylcarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methoxymethyl, phenylcarbonyl and phenylcarbonyl wherein the phenyl ring is substituted with one or more radicals selected from methyl, chloro, methoxy, aminocarbonyl and hydrazidylcarbonyl, cyano, nitro, hydroxyl, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, cyclohexylmethoxy, carboxyl, formyl, acetyl, propionyl, aminocarbonyl, methylaminocarbonyl, dimethylaminocarbonyl, benzyloxy, aminosulfonyl, dimethylaminosulfonyl, methylsulfonylamino, morpholinyl, pyrrolidinyl, piperazinyl, piperidyl, phthalimidyl, benzyl, methoxycarbonyl, ethoxycarbonyl, pyridyl, methylthio, methylsulfinyl, methylsulfonyl, phenylthio, benzylthio, and cyclohexylthio; wherein each of $R^3$, $R^4$, $R^5$ and $R^6$ is independently selected from hydrido, methyl, ethyl, propyl, butyl, pentyl, isopropyl, isobutyl, tert-butyl, phenyl and benzyl; or wherein $R^3$ and $R^4$, or $R^5$ and $R^6$ together form cyclopropyl, cyclobutyl or cyclopentyl; wherein $R^7$ is one or more radicals selected from methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, cyclohexyl, cyclopropyl, cyclobutyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, trifluoroethoxy, carboxyl, formyl, acetyl, propionyl, butyryl, N-methylamino, N-ethylamino, N-propylamino, N-butylamino, N-tert-butylamino, N-pentylamino, N-hexylamino, N,N-dimethylamino, phenylamino, N-methy-N-phenylamino, methylaminomethyl, aminocarbonyl, N-methylaminocarbonyl, N,N-dimethylaminocarbonyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, phenoxycarbonyl, benzyloxycarbonyl, methylcarbonyl, cyclohexylcarbonyl, methylcarbonylmethyl, methoxycarbonylmethyl, N,N-dimethylaminocarbonyl, aminocarbonyloxy, phenoxy, benzoxy, benzyl, phenethyl, phenyl, benzoyl, methoxymethyl, hydroxymethyl, morpholinyl, pyrrolidinyl, piperazinyl, piperidyl, methylthio, ethylthio, methylsulfinyl, ethylsulfinyl, methylsulfonyl, phenylthio, phenylsulfinyl, phenylsulfonyl, aminosulfonyl, methylsulfonylamino, methylaminosulfonyl and N,N-dimethylaminosulfonyl; or wherein $R^5$ and $R^8$ taken together form a ring; and wherein $R^8$ is selected from hydrido, methyl, ethyl, propyl, butyl, pentyl, isopropyl, isobutyl, tert-butyl, butene, pentene, isopropylene, isobutylene, hydroxymethyl, phenyl, naphthyl, phenoxymethyl, methylthiomethyl, benzyl, phenethyl, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methoxymethyl, aminocarbonyl, formyl, acetyl, propionyl, butyryl, methylaminocarbonyl and methylsulfonyl; or a pharmaceutically acceptable salt thereof.

9. Method of claim 8 selected from the group consisting of compounds, and their pharmaceutically acceptable salts, of the group selected from:

2-[(4,6-dimethyl-5-methoxy-2-phthalimidylphenyl) methylsulfonyl]-5-methoxy-1H-benzimidazole;

2-[[(5-chloro-1H-benzimidazol-2-yl)sulfinyl]methyl]-3,5-dimethyl-4-methoxybenzenamine;

(+)-2-[[(5-methoxy-1H-benzimidazol-2-yl)sulfinyl]methyl]-3,5-dimethyl-4-methoxybenzenamine;

(−)-2-[[(5-methoxy-1H-benzimidazol-2-yl)sulfinyl]methyl]-3,5-dimethyl-4-methoxybenzenamine;

N-[2-[[(6-methoxy-1H-benzimidazol-2-yl)sulfinyl]methyl]-3,5-dimethyl-4-methoxyphenyl]acetamide;

2-[(4,6-dimethyl-5-methoxy-2-phthalimidylphenyl)methylsulfinyl]-6-chloro-1-isopropyl-1H-benzimidazole;

2-[(4,6-dimethyl-5-methoxy-2-phthalimidylphenyl)methylsulfinyl]-5-chloro-1-isopropyl-1H-benzimidazole;

2-[(4,6-dimethyl-5-methoxy-2-phthalimidylphenyl)methylsulfinyl]-5-chloro-1-ethyl-1H-benzimidazole;

2-[(4,6-dimethyl-5-methoxy-2-phthalimidylphenyl)methylsulfinyl]-6-chloro-1-ethyl-1H-benzimidazole;

2-[[[2-[[(6-chloro-1-ethyl-1H-benzimidazol-2-yl)sulfinyl]methyl]-3,5-dimethyl-4-methoxyphenyl]amino]carbonyl]benzenecarboxylic acid hydrazide;

2-[[[2-[[(5-chloro-1-ethyl-1H-benzimidazol-2-yl)sulfinyl]methyl]-3,5-dimethyl-4-methoxyphenyl]amino]carbonyl]benzenecarboxylic acid hydrazide;

3-[[(1H-benzimidazol-2-yl)sulfinyl]methyl]benzenamine;

2-[[3-methylpyridin-2-ylmethyl]sulfinyl]-1H-benzimidazole;

2-[(imidazo[1,2-a]pyridin-3-yl)methylsulfinyl]-1H-benzimidazole;

2-[(imidazo[1,2-a]pyridin-3-yl)methylsulfinyl]-1H-benzimidazole;

2-[(imidazo[1,2-a]pyridin-3-yl)methylsulfinyl]-5-methyl-1H-benzimidazole;

2-[(imidazo[1,2-a]pyridin-3-yl)methylsulfinyl]-5-methoxy-1H-benzimidazole;

5-chloro-2-[(imidazo[1,2-a]pyridin-3-yl)methylsulfinyl]-1H-benzimidazole;

2-[(imidazo[1,2-a]pyridin-3-yl)methylsulfinyl]-5-trifluoromethyl-1H-benzimidazole;

2-[(imidazo[1,2-a]pyridin-8-yl)methylsulfinyl]-1H-benzimidazole;

2-[(imidazo[1,2-a]pyridin-8-yl)methylsulfinyl]-1H-benzimidazole;

2-[(imidazo[1,2-a]pyridin-8-yl)methylsulfinyl]-5-methoxy-1H-benzimidazole;

5-ethoxy-2-[(imidazo[1,2-a]pyridin-8-yl)methylsulfinyl]-1H-benzimidazole;

2-[(imidazo[1,2-a]pyridin-8-yl)methylsulfinyl]-4-methyl-1H-benzimidazole;

2-[(imidazo[1,2-a]pyridin-8-yl)methylsulfinyl]-5-methyl-1H-benzimidazole;

2-[(imidazo[1,2-a]pyridin-8-yl)methylsulfinyl]-5,6-dimethyl-1H-benzimidazole;

2-[(imidazo[1,2-a]pyridin-8-yl)methylsulfinyl]-5,6-dimethoxy-1H-benzimidazole;

5-chloro-2-[(imidazo[1,2-a]pyridin-8-ylmethyl)sulfinyl]-1H-benzimidazole;

2-[(imidazo[1,2-a]pyridin-8-yl)methylsulfinyl]-5-trifluoromethyl-1H-benzimidazole;

2-[[(2,3-dimethylimidazo[1,2-a]pyridin-8-yl)methyl]sulfinyl]-1H-benzimidazole;

2-[[(3-methylimidazo[1,2-a]pyridin-8-yl)methyl]sulfinyl]-1H-benzimidazole;

2-[[(2-phenylimidazo[1,2-a]pyridin-8-yl)methyl]sulfinyl]-1H-benzimidazole;

2-[[(3-phenylimidazo[1,2-a]pyridin-8-yl)methyl]sulfinyl]-1H-benzimidazole;

2-[[(3-(4-nitrophenyl)imidazo[1,2-a]pyridin-8-yl)methyl]sulfinyl]-1H-benzimidazole;

2-[[[3-[3-(trifluoromethyl)phenyl]imidazo[1,2-a]pyridin-8-yl]methyl]sulfinyl]-1H-benzimidazole;

5-methyl-2-[[[3-[3-(trifluoromethyl)phenyl]imidazo[1,2-a]pyridin-8-yl]methyl]sulfinyl]-1H-benzimidazole;

5-chloro-2-[[[3-[3-(trifluoromethyl)phenyl]imidazo[1,2-a]pyridin-8-yl]methyl]sulfinyl]-1H-benzimidazole;

2-[[[3-[4-(trifluoromethyl)phenyl]imidazo[1,2-a]pyridin-8-yl]methyl]sulfinyl]-1H-benzimidazole;

5-chloro-2-[[[3-[4-(trifluoromethyl)phenyl]imidazo[1,2-a]pyridin-8-yl]methyl]sulfinyl]-1H-benzimidazole;

4-[8-[(1H-benzimidazol-2-yl)sulfinylmethyl]imidazo[1,2-a]pyridin-3-yl]benzoate;

2-[[[3-(4-chlorophenyl)imidazo[1,2-a]pyridin-8-yl]methyl]sulfinyl]-1H-benzimidazole;

2-[[[3-(4-methylphenyl)imidazo[1,2-a]pyridin-8-yl]methyl]sulfinyl]-1H-benzimidazole;

2-[(imidazo[1,2-a]pyridin-5-yl)methylsulfinyl]-1H-benzimidazole;

4,6-dimethyl-2-(((imidazo(1,2-a)pyridin-2-yl)methyl)thio)-1H-benzimidazole;

2-[3-methyl-4-(2-(N-benzyl-N-cyclohexylamino)-ethoxy)pyridyl]methylthio-1H-benzimidazole;

ethyl 2-[(1H-benzimidazol-2-yl)thiomethyl]-4-methyl-amino-5-pyrimidine carboxylate;

2-(5-fluoro-2-(4-methoxy-2-pyridyl)-phenylsulfinyl)-1H-benzimidazole;

5-difluoromethoxy-2-(((3,4-dimethoxy-2-pyridinyl) methyl)sulfinyl)-1H-benzimidazole;

2-(((4-difluoromethoxy-3-methyl-2-pyridyl) methylsulfinyl)benzimidazole;

2-((6-azachroman-5-yl)methylsulfinyl)-benzimidazole;

5-carbomethoxy-6-methyl-2-(((3,4-dimethoxy-2-pyridinyl)methyl)sulfinyl-1H-benzimidazole;

5-carbomethoxy-6-methyl-2-(((3,4-dimethoxy-2-pyridinyl)methyl)sulfinyl)-1H-benzimidazol-1-yl-methyl ethyl carbonate;

2-((3-methyl-4-(2,2,2-trifluoroethoxy)-2-pyridyl) methylsulfinyl)benzimidazole;

4-fluoro-2-(((4-methoxy-2-pyridinyl)methyl)sulfiinyl-1H-benzimidazol-1-yl-methyl-ethylcarbonate;

2-[3-methyl-4-(1-benzyl-4-piperidyl)oxy-2-pyridyl] methylthio-1H-benzimidazole;

2-(3-methyl-4-(2-(N-methyl-N-(4-methyl-benzyl)amino) ethoxy)-2-pyridyl)methylsulfonyl-1H-benzimidazole;

2-(4-methoxy-6-methyl-2-pyrimidinyl)methylthio-1H-benzimidazole;

5-chloro-2-(3,4-dimethoxy-2-pyridylmethylsulfinyl)-1H-benzimidazole;

5-fluoro-2-(4-cyclopropylmethoxy-2-pyridylmethyl-sulfinyl)-1H-benzimidazole;

4-fluoro-2-(4-methoxy-2-pyridylmethylsulfinyl)-1H-benzimidazole;

2-(((4-methoxy-3,5-dimethyl-2-pyridyl)-methyl)-sulfinyl)-5-methoxy-1H-benzimidazole;

5-hydroxymethyl-2-((3,5-dimethyl-4-methoxy-2-pyridyl) methylthio-1H-benzimidazole;

2-(4-ethylthio-3-methylpyrid-2-yl-methyl)sulfinyl-benzimidazole;

2-(((4-(2-benzyloxyethoxy)-3-methyl-2-pyridyl) methylthio)benzimidazole;

2-[[2-[N-(2-hydroxyethyl)-N-methylamino]-5-methoxy] benzylsulfinyl]benzimidazole;

2-(5-benzyl-4-chloro-6-methyl-2-pyrimidinyl) methylthio-1H-benzimidazole;

5-carboethoxy-6-methyl-2-(((3-methyl-2-pyridyl)methyl) sulfinyl)-1H-benzimidazole;

5-(2-benzimidazolylsulfinylmethyl)-3,4-dihydro-4-methyl-2H-1,4-benzoxazine;

2-(3-methyl-4-(2-(N-benzyl-N-methylamino)ethoxy-2-pyridyl)methylsulfinyl-1H-benzimidazole;

2-(3-methyl-4-(2-(1,2,3,4-tetrahydroisoquinolin- 2-yl)-ethoxy)-2-pyridyl)methylsulfinyl-1H-benzimidazole;

2-[1-(3,5-dimethylpyrazolyl)]methylthiobenzimidazole;

2-(3-chloro-4-methoxy-2-picolylthio)-5-methoxy-1H-benzimidazole;

2-(4-(2-ethoxyethoxy)-3-methyl-2-pyridyl) methylsulfinyl-1H-benzimidazole;

2-(3-methylthieno(2,3-c)pyridin-7-yl)methylsulfinyl)-benzimidazole;

2-(2-dimethylamino-5-methoxybenzylsulfinyl)-5-methoxy-benzimidazole;

2-(2-dimethylamino-5-methylbenzylsulfinyl)-5-methoxybenzimidazole;

2-[4-(2,3,5-trimethyl)pyridylthio]-5-methoxybenzimidazole;

2-[(2-(4-chlorophenyl)-5-methylimidazol-4-yl) methylthio]benzimidazole;

2-(5-hydroxy-1H-benzimidazol-2-ylsulfinylmethyl)-N,N-dimethylbenzenamine;

2-((6-methoxyisoquinolin-1-yl)methylsulfinyl) benzimidazole;

3-(5-methoxy-1H-benzimidazol-2-yl)thiomethylcarbo-styril;

5-methoxy-2-(4-dimethylamino-5-fluoro-2-pyridylmethylsulfinyl)-1H-benzimidazole;

2-(2-dimethylaminobenzylsulfinyl)-5-cyclopropylmethoxybenzimidazole;

2-(3,5-dimethyl-2-pyridylmethylsulfinyl)-5-cyclopropylmethoxy-benzimidazole;

2-[2-(N-cyclohexyl-N-methylamino)benzylsulfonyl] benzimidazole;

8-(5-fluoro-6-methoxy-2-benzimidazolyl)sulfinylmethyl-1-ethyl-4-(N-methyl-N-allyl)amino-1,2,3,4-tetrahydroquinoline;

2-(2-benzyloxycarbonylaminobenzylthio)benzimidazole;

2-(2-benzimidazolylmethylthio)pyrimidine;

5-acetyl-2-((2-dimethylaminobenzyl)sulfinyl) benzimidazole;

2-((3,5-dimethyl-4-methoxy-2-pyridyl)methylsulfinyl)-5-fluoro-1H-benzimidazole;

2-(3-pyridylmethylthio)-5-methoxybenzimidazole;

2-(2-methylaminobenzylsulfinyl)benzimidazole;

5-methoxy-2-(2-dimethylaminobenzylsulfinyl)-1H-benzimidazole;

2-(3,4-dimethoxypyrid-2-ylmethylsulfinyl)-5-trifluoromethyl-benzimidazole;

5-methoxy-2-(4-piperidino-2-pyrimidinylmethyl-sulfinyl)-(1H)-benzimidazole;

2-[2-(4-benzyloxy)-pyridylmethylsulfinyl] benzimidazole;

4-allyloxy-8-(2-benzimidazolyl)thio-3-methyl-5,6,7,8-tetrahydroquinoline;

2-[2-(4-methoxy-5-n-pentyl)-pyridylmethylthio] benzimidazole;

2-(5-bromo-4-piperidino-2-pyridylmethylsulfinyl)-5-methoxy-(1H)-benzimidazole;

2-(((3,5-dimethyl-4-morpholinopyrid-2-yl) methylsulfinyl)benzimidazole;

2-((2-pyridinylmethyl)sulfinyl)-1H-benzimidazole-1-methanol;

2-((3,4-dihydro-2H-thieno(3,2-c)pyridinylmethyl)thio)-1H-benzimidazole-1-methanol;

2-(4-isopropoxy-2-pyridyl)methylsulfinylbenzimidazole;

2-((4-fluorobenzyloxy-3-methyl-2-pyridyl) methylsulfinyl)benzimidazole;

2-(2-aminobenzylsulfinyl)-benzimidazole;

N,N-dimethyl-2-(1H-benzimidazol-2-yl-sulfinylmethyl) benzenamine;

2-[(4,5-dimethoxy-2-pyridyl)methylsulfinyl]-5-trifluoromethoxy-1H-benzimidazole;

2-((4-morpholinyl-3-ethylpyridin-2-yl)methylsulfinyl)-5-trifluoromethylbenzimidazole;

2-((4-methoxy-2-pyridyl)methylsulfinyl)-5-trifluoromethoxy-1H-benzimidazole;

5-cyclopropylcarbonyl-2-((4-methoxy-2-pyridyl)methyl-sulfinyl)-1H-benzimidazole;

2-[2-(3,5-dimethyl-4-methoxy)-pyridylmethylsulfinyl]-(5-chloro)-benzimidazole;

2-[2-(4,5-dimethyl)-pyridylmethylsulfinyl]-(5-acetyl-6-methyl)-benzimidazole;
2-[2-(3,5-dimethyl)pyridylmethylsulfinyl]5-fluoro-benzoxazole;
3-[(4-dimethylamino-2-pyridyl)methylthio]indole;
6-benzoylamino-7-chloro-2-(((3,5-dimethyl-4-methoxy-2-pyridyl)-methyl)thio)benzothiazole;
5-(4,5-dihydro-2-oxazolyl)-2-((3,5-dimethyl-4-methoxy-2-pyridyl)methylthio)-1H-benzimidazole;
2-gernaylthio-benzimidazole;
ethyl 2-((1H-benzimidazol-2-yl)-sulfinylmethyl)-4-dimethylamino-5-pyrimidinecarboxylate;
2-[(1H-benzimidazol-2-yl)sulfinylmethyl]benzenamine;
2-[(1H-benzimidazol-2-yl)sulfinylmethyl]N,N-dimethylbenzenamine;
N-[2-[(1H-benzimidazol-2-yl)sulfinylmethyl]phenyl]acetamide;
2-[[(4-methyl-1H-benzimidazol-2-yl)sulfinyl]methyl]benzenamine;
2-[[(5,6-dimethyl-1H-benzimidazol-2-yl)sulfinyl]methyl]benzenamine;
2-[[(5-methoxy-1H-benzimidazol-2-yl)sulfinyl]methyl]benzenamine;
methyl 2-[[(2-aminophenyl)methyl]sulfinyl]-5-methoxy-1H-benzimidazole-6-carboxylate;
2-[(1H-benzimidazol-2-yl)sulfinylmethyl]-4-chlorobenzenamine;
2-[(1H-benzimidazol-2-yl)sulfinylmethyl]-5-chlorobenzenamine;
2-[(1H-benzimidazol-2-yl)sulfinylmethyl]-4-methoxybenzenamine;
2-[(1H-benzimidazol-2-yl)sulfinylmethyl]-6-methoxybenzenamine;
2-[(1H-benzimidazol-2-yl)sulfinylmethyl]-3-methylbenzenamine;
2-[(1H-benzimidazol-2-yl)sulfinylmethyl]-4-methylbenzenamine;
2-[(1H-benzimidazol-2-yl)sulfinylmethyl]-6-methylbenzenamine;
2-[(1H-benzimidazol-2-yl)sulfinylmethyl]-4,6-dimethylbenzenamine;
2-[(1H-benzimidazol-2-yl)sulfinylmethyl]-N-methylbenzenamine;
2-[[(5-methoxy-1H-benzimidazol-2-yl)sulfinyl]methyl]-4-methylbenzenamine;
2-[[(5-methoxy-1H-benzimidazol-2-yl)sulfinyl]methyl]-6-methylbenzenamine;
2-[(1H-benzimidazol-2-yl)sulfinylmethyl]-4-ethylbenzenamine;
2-[(1H-benzimidazol-2-yl)sulfinylmethyl]-6-ethylbenzenamine;
2-[(1H-benzimidazol-2-yl)sulfinylmethyl]-4-methoxy-3,5-dimethylbenzenamine;
2-[[(5-methyl-1H-benzimidazol-2-yl)sulfinyl]-methyl]benzenamine;
2-[[(5-chloro-1H-benzimidazol-2-yl)sulfinyl]-methyl]benzenamine;
2-[[(5-ethoxy-1H-benzimidazol-2-yl)sulfinyl]-methyl]benzenamine;
2-[[[(5-(trifluoromethyl)-1H-benzimidazol-2-yl]sulfinyl]methyl]benzenamine;
2-[(1H-benzimidazol-2-yl)sulfinylmethyl]-4-(trifluoromethyl)benzenamine;
2-[(1H-benzimidazol-2-yl)sulfinylmethyl]-4-butylbenzenamine;
2-[(1H-benzimidazol-2-yl)sulfinylmethyl]-5,6-dimethylbenzenamine;
2-[(1H-benzimidazol-2-yl)sulfinylmethyl]-3,6-dimethylbenzenamine;
2-[(1H-benzimidazol-2-ylsulfinylmethyl]-4-chloro-6-methylbenzenamine;
2-[(1H-benzimidazol-2-ylsulfiny)methyl]-4-chloro-6-methoxy-3-methylbenzenamine;
2-[[(5-ethoxy-1H-benzimidazol-2-yl)sulfinyl]-methyl]-4-methylbenzenamine;
2-[[(5-methyl-1H-benzimidazol-2-yl)sulfinyl]-methyl]-5,6-dimethylbenzenamine;
2-[[[(5-(trifluoromethy)1-1H-benzimidazol-2-yl]sulfinyl]-3,6-dimethylbenzenamine;
2-[[[(5-(trifluoromethyl)1-1H-benzimidazol-2-yl]sulfinyl]methyl]-6-methoxybenzenamine;
methyl 2-amino-3-[(1H-benzimidazol-2-yl)sulfinylmethyl]benzoate;
ethyl 4-amino-3-[(1H-benzimidazol-2-ylsulfinyl)methyl]benzoate;
ethyl 4-amino-3-[[(5-methoxy-1H-benzimidazol-2-yl)sulfinyl]methyl]benzoate;
2-[[5,6-dimethoxy-1H-benzimidazol-2-yl)sulfinyl]methyl]-4-methylbenzenamine;
2-[(1H-benzimidazol-2-yl)sulfinylmethyl]-4-fluorobenzenamine;
2-[(1H-benzimidazol-2-yl)sulfinylmethyl]-3,4,5-trimethylbenzenamine;
2-[[(5-methoxy-1H-benzimidazol-2-yl)sulfinyl]methyl]-4-methoxy-3,5-dimethylbenzenamine;
3-[(1H-benzimidazol-2-yl)sulfinylmethyl]benzenamine;
3-[(1H-benzimidazol-2-yl)sulfinylmethyl]-2-pyridinamine;
3-[(1H-benzimidazol-2-yl)sulfinylmethyl]-N,N-dimethyl-2-pyridinamine;
6-[(1H-benzimidazol-2-yl)sulfinylmethyl]-2-pyridinamine;
6-[[(4-methyl-1H-benzimidazol-2-yl)-sulfinyl]methyl]-2-pyridinamine;
6-[[(5-methyl-1H-benzimidazol-2-yl)-sulfinyl]methyl]-2-pyridinamine;
6-[[(5-methoxy-1H-benzimidazol-2-yl)sulfinyl]-methyl]-2-pyridinamine;
6-[[(5-chloro-1H-benzimidazol-2-yl)-sulfinyl]methyl]-2-pyridinamine;
6-[[[5-(trifluoromethyl)-1H-benzimidazol-2-yl]sulfinyl]methyl]-2-pyridinamine;
6-[[(5-ethoxy-1H-benzimidazol-2-yl)-sulfinyl]methyl]-2-pyridinamine;
6-[[(5,6-dimethoxy-1H-benzimidazol-2-yl)-sulfinyl]methyl]-2-pyridinamine;
6-[[(5,6-dimethyl-1H-benzimidazol-2-yl)-sulfinyl]methyl]-2-pyridinamine;
6-[[(4,6-dimethyl-1H-benzimidazol-2-yl)-sulfinyl]methyl]-2-pyridinamine;
6-[[[5-(hydroxymethyl)-1H-benzimidazol-2-yl]sulfinyl]methyl]-2-pyridinamine;

6-[(1H-benzimidazol-2-yl)sulfinylmethyl]-N-(2,2-dimethylpropyl)-2-pyridinamine;

6-[(1H-benzimidazol-2-yl)sulfinylmethyl]-N-ethyl-2-pyridinamine; and

5-[(1H-benzimidazol-2-yl)sulfinylmethyl]-2-pyridinamine.

10. A method of inhibiting a viral protease, said method comprising treating said subject with an effective amount of a compound of Formula III

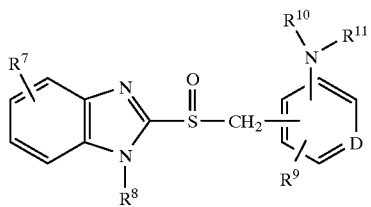

wherein D is N or CH; wherein $R^7$ is one or more radicals selected from hydrido, $C_1$–$C_{10}$-alkoxy, amino, cyano, nitro, hydroxyl, $C_1$–$C_{20}$-alkyl, halo, $C_1$–$C_{20}$-haloalkyl, carboxyl, $C_1$–$C_{20}$-alkanoyl, nitro, amino, $C_1$–$C_{20}$-alkylamino, aminocarbonyl, $C_1$–$C_{20}$-alkylaminocarbonyl, $C_1$–$C_{20}$-alkylcarbonylamino, aminosulfonyl, $C_1$–$C_{20}$-alkylaminosulfonyl, $C_1$–$C_{20}$-alkylsulfonyl amino, $C_1$-$C_{10}$-alkoxycarbonyl, $C_1$–$C_{20}$-alkylthio, $C_1$–$C_{20}$-alkylsulfinyl and $C_1$–$C_{20}$-alkylsulfonyl; wherein $R^8$ is selected from hydrido, $C_1$–$C_{20}$-alkyl and $C_3$–$C_{10}$-cycloalkyl; wherein $R^9$ is one or more radicals selected from hydrido, $C_1$–$C_{10}$-alkoxy, amino, $C_1$–$C_{20}$-alkyl, halo, cyano, nitro, hydroxyl, $C_1$–$C_{20}$-haloalkyl, carboxyl, $C_1$–$C_{20}$-alkanoyl, nitro, $C_1$–$C_{20}$-alkylamino, $C_1$–$C_{20}$-dialkylamino, aminocarbonyl, $C_1$–$C_{20}$-alkylaminocarbonyl, $C_1$–$C_{20}$-alkylcarbonylamino, aminosulfonyl, $C_1$–$C_{20}$-alkylaminosulfonyl, $C_1$–$C_{20}$-alkylsulfonylamino, $C_1$–$C_{10}$-alkoxycarbonyl, $C_1$–$C_{20}$-alkylthio, $C_1$–$C_{20}$-alkylsulfinyl and $C_1$–$C_{20}$-alkylsulfonyl; and wherein $R^{10}$ and $R^{11}$ are independently selected from hydrido, $C_1$–$C_{20}$-alkyl, aryl, $C_1$–$C_{20}$-alkylcarbonyl, arylcarbonyl and arylcarbonyl wherein the aryl ring is substituted with-one or more radicals selected from $C_1$–$C_{20}$-alkyl, halo, $C_1$–$C_{10}$-alkoxy, aminocarbonyl and hydrazidylcarbonyl, or wherein $R^{10}$ and $R^{11}$ together with the nitrogen atom form a heterocyclic ring; or a pharmaceutically acceptable salt thereof.

11. Method of claim 10 wherein $R^7$ is one or more radicals selected from hydrido, $C_1$–$C_6$-alkoxy, amino, cyano, nitro, hydroxyl, $C_1$–$C_{10}$-alkyl, halo, $C_1$–$C_{10}$-haloalkyl, carboxyl, $C_1$–$C_{10}$-alkanoyl, $C_1$–$C_{10}$-alkylamino, aminocarbonyl, $C_1$–$C_{10}$-alkylaminocarbonyl, $C_1$–$C_{10}$-alkylcarbonylamino, aminosulfonyl, $C_1$–$C_{10}$-alkylaminosulfonyl, $C_1$–$C_{10}$-alkylsulfonylamino, $C_1$–$C_6$-alkoxycarbonyl, $C_1$–$C_{10}$-alkylthio, $C_1$–$C_{10}$-alkylsulfinyl and $C_1$–$C_{10}$-alkylsulfonyl; wherein $R^8$ is selected form hydrido, $C_1$–$C_{10}$-alkyl and $C_3$–$C_6$-cycloalkyl; wherein $R^9$ is one or more radicals selected from hydrido, $C_1$–$C_6$-alkoxy, amino, $C_1$–$C_{10}$-alkyl, halo, cyano, nitro, hydroxyl, $C_1$–$C_{10}$-haloalkyl, carboxyl, $C_1$–$C_{10}$-alkanoyl, $C_1$–$C_{10}$-alkylamino, aminocarbonyl, $C_1$–$C_{10}$-alkylaminocarbonyl, $C_1$–$C_{10}$-alkylcarbonylamino, aminosulfonyl, $C_1$–$C_{10}$-alkylaminosulfonyl, $C_1$–$C_{10}$-alkylsulfonylamino, $C_1$–$C_6$-alkoxycarbonyl, $C_1$–$C_{10}$-alkylthio, $C_1$–$C_{10}$-alkylsulfinyl and $C_1$–$C_{10}$-alkylsulfonyl; and wherein $R^{10}$ and $R^{11}$ are independently selected from hydrido, phenyl, $C_1$–$C_{10}$-alkylcarbonyl, $C_1$–$C_{10}$-alkyl, phenylcarbonyl and phenylcarbonyl wherein the phenyl ring is substituted with one or more radicals selected from $C_1$–$C_{10}$-alkyl, halo, $C_1$–$C_6$-alkoxy, aminocarbonyl and hydrazidylcarbonyl, or wherein $R^{10}$ and $R^{11}$ together with the nitrogen atom form a heterocyclic ring; or a pharmaceutically acceptable salt thereof.

12. Method of claim 11 wherein $R^7$ is one or more radicals selected from hydrido, methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxyl, formyl, acetyl, propionyl, N-methylamino, N-ethylamino, N-propylamino, N-butylamino, N-tert-butylamino, N-pentylamino, N-hexylamino, N,N-dimethylamino, aminocarbonyl, N-methylaminocarbonyl, N,N-dimethylaminocarbonyl, methylcarbonylamino, aminosulfonyl, methylaminosulfonyl, methylsulfonylamino, methoxycarbonyl, ethoxycarbonyl, isopropoxycarbonyl, tert-butoxycarbonyl, propoxycarbonyl, n-butycarbonyl, isobutoxycarbonyl, pentoxycarbonyl, methylthio, methylsulfinyl and methylsulfonyl; wherein $R^8$ is selected from hydrido, methyl, ethyl, propyl, butyl, pentyl, isopropyl, isobutyl, tert-butyl, cyclopropyl, cyclobutyl and cyclopentyl; wherein $R^9$ is one or more radicals selected from hydrido, methoxy, ethoxy, propoxy, butoxy, isopropoxy, tert-butoxy, amino, methyl, ethyl, propyl, butyl, pentyl, isopropyl, isobutyl, tert-butyl, fluoro, chloro, bromo, iodo, cyano, nitro, hydroxyl, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxyl, formyl, acetyl, propionyl, N-methylamino, N-ethylamino, N-propylamino, N-butylamino, N-tert-butylamino, N-pentylamino, N-hexylamino, N,N-dimethylamino, aminocarbonyl, N-methylaminocarbonyl, N,N-dimethylaminocarbonyl, aminosulfonyl, methylaminosulfonyl, methylsulfonylamino, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methylthio, methylsulfinyl and methylsulfonyl; and wherein $R^{10}$ and $R^{11}$ are independently selected from hydrido, methyl, ethyl, propyl, butyl, pentyl, isopropyl, isobutyl, tert-butyl, phenyl, methylcarbonyl, phenylcarbonyl and phenylcarbonyl wherein the phenyl ring is substituted with one or more radicals selected from methyl, chloro, methoxy, aminocarbonyl and hydrazidylcarbonyl, or wherein $R^{10}$ and $R^{11}$ together with the nitrogen atom form phthalimidyl, morpholinyl, and piperazinyl; or a pharmaceutically acceptable salt thereof.

13. Method according to claim 12 selected from the group consisting of compounds, and their pharmaceutically acceptable salts, of the group selected from:

2-[[(5-chloro-1H-benzimidazol-2-yl)sulfinyl]methyl]-3,5-dimethyl-4-methoxybenzenamine;

(−)-2-[[(5-methoxy-1H-benzimidazol-2-yl)sulfinyl]methyl]-3,5-dimethyl-4-methoxybenzenamine;

(+)-2-[[(5-methoxy-1H-benzimidazol-2-yl)sulfinyl]methyl]-3,5-dimethyl-4-methoxybenzenamine;

N-[2-[[(6-methoxy-1H-benzimidazol-2-yl)sulfinyl]methyl]-3,5-dimethyl-4-methoxyphenyl]acetamide;

2-[(4,6-dimethyl-5-methoxy-2-phthalimidylphenyl)methylsulfinyl]-6-chloro-1-isopropyl-1H-benzimidazole;

2-[(4,6-dimethyl-5-methoxy-2-phthalimidylphenyl) methylsulfinyl]-5-chloro-1-isopropyl-1H-benzimidazole;

2-[(4,6-dimethyl-5-methoxy-2-phthalimidylphenyl) methylsulfinyl]-5-chloro-1-ethyl-1H-benzimidazole;

2-[(4,6-dimethyl-5-methoxy-2-phthalimidylphenyl) methylsulfinyl]-6-chloro-1-ethyl-1H-benzimidazole;

2-[[[2-[[(6-chloro-1-ethyl-1H-benzimidazol-2-yl) sulfinyl]methyl]-3,5-dimethyl-4-methoxyphenyl] amino]carbonyl]benzenecarboxylic acid hydrazide;

2-[[[2-[[(5-chloro-1-ethyl-1H-benzimidazol-2-yl) sulfinyl]methyl]-3,5-dimethyl-4-methoxyphenyl] amino]carbonyl]benzenecarboxylic acid hydrazide;

3-[[(1H-benzimidazol-2-yl)sulfinyl]methyl] benzenamine;

2-[(1H-benzimidazol-2-yl)sulfinylmethyl]benzenamine;

2-[(1H-benzimidazol-2-yl)sulfinylmethyl]N,N-dimethylbenzenamine;

N-[2-[(1H-benzimidazol-2-yl)sulfinylmethyl]phenyl] acetamide;

2-[[(4-methyl-1H-benzimidazol-2-yl)sulfinyl]methyl] benzenamine;

2-[[(5,6-dimethyl-1H-benzimidazol-2-yl)sulfinyl] methyl]benzenamine;

2-[[(5-methoxy-1H-benzimidazol-2-yl)sulfinyl]methyl] benzenamine;

methyl 2-[[(2-aminophenyl)methyl]sulfinyl]-5-methoxy-1H-benzimidazole-6-carboxylate;

2-[(1H-benzimidazol-2-yl)sulfinylmethyl]-4-chlorobenzenamine;

2-[(1H-benzimidazol-2-yl)sulfinylmethyl]-5-chlorobenzenamine;

2-[(1H-benzimidazol-2-yl)sulfinylmethyl]-4-methoxybenzenamine;

2-[(1H-benzimidazol-2-yl)sulfinylmethyl]-6-methoxybenzenamine;

2-[(1H-benzimidazol-2-yl)sulfinylmethyl]-3-methylbenzenamine;

2-[(1H-benzimidazol-2-yl)sulfinylmethyl]-4-methylbenzenamine;

2-[(1H-benzimidazol-2-yl)sulfinylmethyl]-6-methylbenzenamine;

2-[(1H-benzimidazol-2-yl)sulfinylmethyl]-4,6-dimethylbenzenamine;

2-[(1H-benzimidazol-2-yl)sulfinylmethyl]-N-methylbenzenamine;

2-[[(5-methoxy-1H-benzimidazol-2-yl)sulfinyl]methyl]-4-methylbenzenamine;

2-[[(5-methoxy-1H-benzimidazol-2-yl)sulfinyl]methyl]-6-methylbenzenamine;

2-[(1H-benzimidazol-2-yl)sulfinylmethyl]-4-ethylbenzenamine;

2-[(1H-benzimidazol-2-yl)sulfinylmethyl]-6-ethylbenzenamine;

2-[(1H-benzimidazol-2-yl)sulfinylmethyl]-4-methoxy-3,5-dimethylbenzenamine;

2-[[(5-methyl-1H-benzimidazol-2-yl)sulfinyl]-methyl] benzenamine;

2-[[(5-chloro-1H-benzimidazol-2-yl)sulfinyl]-methyl] benzenamine;

2-[[(5-ethoxy-1H-benzimidazol-2-yl)sulfinyl]-methyl] benzenamine;

2-[[[(5-(trifluoromethyl)-1H-benzimidazol-2-yl]sulfinyl] methyl]benzenamine;

2-[(1H-benzimidazol-2-yl)sulfinylmethyl]-4-(trifluoromethyl)benzenamine;

2-[(1H-benzimidazol-2-yl)sulfinylmethyl]-4-butylbenzenamine;

2-[(1H-benzimidazol-2-yl)sulfinylmethyl]-5,6-dimethylbenzenamine;

2-[(1H-benzimidazol-2-yl)sulfinylmethyl]-3,6-dimethylbenzenamine;

2-[(1H-benzimidazol-2-yl)sulfinylmethyl]-4-chloro-6-methylbenzenamine;

2-[(1H-benzimidazol-2-ylsulfiny)methyl]-4-chloro-6-methoxy-3-methylbenzenamine;

2-[[(5-ethoxy-1H-benzimidazol-2-yl)sulfinyl]-methyl]-4-methylbenzenamine;

2-[[(5-methyl-1H-benzimidazol-2-yl)sulfinyl]-methyl]-5,6-dimethylbenzenamine;

2-[[[(5-(trifluoromethy)1-1H-benzimidazol-2-yl] sulfinyl]-3,6-dimethylbenzenamine;

2-[[[(5-(trifluoromethy)1-1H-benzimidazol-2-yl]sulfinyl] methyl]-6-methoxybenzenamine;

methyl 2-amino-3-[(1H-benzimidazol-2-yl)sulfinyl) methyl]benzoate;

ethyl 4-amino-3-[(1H-benzimidazol-2-yl)sulfinyl) methyl]benzoate;

ethyl 4-amino-3-[[(5-methoxy-1H-benzimidazol-2-yl) sulfinyl]methyl]benzoate;

2-[[5,6-dimethoxy-1H-benzimidazol-2-yl)sulfinyl] methyl]-4-methylbenzenamine;

2-[(1H-benzimidazol-2-yl)sulfinylmethyl]-4-fluorobenzenamine;

2-[(1H-benzimidazol-2-yl)sulfinylmethyl]-3,4,5-trimethylbenzenamine;

2-[[(5-methoxy-1H-benzimidazol-2-yl)sulfinyl]methyl]-4-methoxy-3,5-dimethylbenzenamine;

3-[(1H-benzimidazol-2-yl)sulfinylmethyl]benzenamine;

3-[(1H-benzimidazol-2-yl)sulfinylmethyl]-2-pyridinamine;

3-[(1H-benzimidazol-2-yl)sulfinylmethyl]-N,N-dimethyl-2-pyridinamine;

6-[(1H-benzimidazol-2-yl)sulfinylmethyl]-2-pyridinamine;

6-[[(4-methyl-1H-benzimidazol-2-yl)-sulfinyl]methyl]-2-pyridinamine;

6-[[(5-methyl-1H-benzimidazol-2-yl)-sulfinyl]methyl]-2-pyridinamine;

6-[[(5-methoxy-1H-benzimidazol-2-yl)sulfinyl]-methyl]-2-pyridinamine;

6-[[(5-chloro-1H-benzimidazol-2-yl)-sulfinyl]methyl]-2-pyridinamine;

6-[[[5-(trifluoromethyl)-1H-benzimidazol-2-yl]sulfinyl] methyl]-2-pyridinamine;

6-[[(5-ethoxy-1H-benzimidazol-2-yl)-sulfinyl]methyl]-2-pyridinamine;

6-[[(5,6-dimethoxy-1H-benzimidazol-2-yl)-sulfinyl] methyl]-2-pyridinamine;

6-[[(5,6-dimethyl-1H-benzimidazol-2-yl)-sulfinyl] methyl]-2-pyridinamine;

6-[[(4,6-dimethyl-1H-benzimidazol-2-yl)-sulfinyl] methyl]-2-pyridinamine;

6-[[[5-(hydroxymethyl)-1H-benzimidazol-2-yl]sulfinyl] methyl]-2-pyridinamine;

6-[(1H-benzimidazol-2-yl)sulfinylmethyl]-N-(2,2-dimethylpropyl)-2-pyridinamine;

6-[(1H-benzimidazol-2-yl)sulfinylmethyl]-N-ethyl-2-pyridinamine; and

5-[(1H-benzimidazol-2-yl)sulfinylmethyl]-2-pyridinamine.

14. Method of claim 10 wherein the viral protease is a herpesvirus protease.

15. Method of claim 14 wherein the viral protease is selected from CMV protease, HSV-1 protease, HSV-2 protease, VZV protease and EBF protease.

16. Method of claim 15 wherein the viral protease is a CMV protease, encoded by $U_L 80$.

17. Method of claim 15 wherein the viral protease is a HSV-1 or a HSV-2 protease, encoded by $U_L 26$.

* * * * *